United States Patent
Stand, III et al.

(10) Patent No.: US 12,121,225 B2
(45) Date of Patent: *Oct. 22, 2024

(54) BIOPSY DEVICE

(71) Applicant: Hologic, Inc., Marlborough, MA (US)

(72) Inventors: Joseph A. Stand, III, Holden, MA (US); Kevin M. Thompson, Framingham, MA (US); Christian M. Ulm, Newton, MA (US); Arnold Oyola, Northborough, MA (US); Fareeha Safir, Brighton, MA (US); Daniel Robertson, Denver, CO (US); Thomas Fisk, Newton, MA (US); Peter Wolton, Louisville, CO (US)

(73) Assignee: Hologic, Inc., Marlborough, MA (US)

( * ) Notice: Subject to any disclaimer, the term of this patent is extended or adjusted under 35 U.S.C. 154(b) by 632 days.

This patent is subject to a terminal disclaimer.

(21) Appl. No.: 17/330,008

(22) Filed: May 25, 2021

(65) Prior Publication Data

US 2022/0008046 A1    Jan. 13, 2022

Related U.S. Application Data

(63) Continuation of application No. 16/032,784, filed on Jul. 11, 2018, now Pat. No. 11,045,172, which is a
(Continued)

(51) Int. Cl.
*A61B 10/02* (2006.01)
*F16H 25/20* (2006.01)
*F16H 25/24* (2006.01)

(52) U.S. Cl.
CPC ...... *A61B 10/0266* (2013.01); *A61B 10/0275* (2013.01); *F16H 25/20* (2013.01);
(Continued)

(58) Field of Classification Search
CPC ............ A61B 10/0266; A61B 10/0275; A61B 2010/0208; A61B 10/0283; F16H 25/20;
(Continued)

(56) References Cited

U.S. PATENT DOCUMENTS

| | | |
|---|---|---|
| 4,940,061 A | 7/1990 | Terwilliger et al. |
| 6,086,544 A | 7/2000 | Hibner et al. |

(Continued)

FOREIGN PATENT DOCUMENTS

| | | |
|---|---|---|
| AU | 20153200537 | 9/2015 |
| CA | 2937424 | 1/2017 |

(Continued)

OTHER PUBLICATIONS

European Examination Report from EP Patent Office for EP application No. 15775567.9, dated May 31, 2018, 6 pages.
(Continued)

*Primary Examiner* — Patrick Fernandes
(74) *Attorney, Agent, or Firm* — Merchant & Gould P.C.

(57) ABSTRACT

A biopsy system driver includes a motor having a rotatable output shaft, a support structure, a drive shaft, an elongate lead screw and a biopsy instrument drive member. The drive shaft is rotatably coupled to the support structure and includes or is otherwise operatively connected to the motor output shaft such that activation of the motor rotates the drive shaft. The elongate lead screw is coupled to the drive shaft such that rotation of the drive shaft rotates the lead screw about an axis of the lead screw. The lead screw is axially translatable relative to the drive shaft and to the support structure. The biopsy instrument drive member is threadably coupled to the lead screw such that rotation of the lead screw causes axial translation of one of the lead screw and biopsy instrument drive member relative to the other one and to the support structure.

20 Claims, 53 Drawing Sheets

Related U.S. Application Data continuation of application No. 14/864,432, filed on Sep. 24, 2015, now Pat. No. 10,022,110.

(60) Provisional application No. 62/055,610, filed on Sep. 25, 2014.

(52) U.S. Cl.
CPC .. *F16H 25/2454* (2013.01); *A61B 2010/0208* (2013.01); *F16H 2025/2081* (2013.01); *F16H 2025/2463* (2013.01)

(58) Field of Classification Search
CPC ......... F16H 25/2454; F16H 2025/2081; F16H 2025/2463
See application file for complete search history.

(56) References Cited

U.S. PATENT DOCUMENTS

| | | | |
|---|---|---|---|
| 10,022,110 | B2 | 7/2018 | Stand |
| 11,045,172 | B2 | 6/2021 | Stand |
| 2004/0162505 | A1 | 8/2004 | Kaplan |
| 2008/0195066 | A1 | 8/2008 | Speeg et al. |
| 2009/0131824 | A1 | 5/2009 | Andrisek et al. |
| 2011/0208090 | A1 | 8/2011 | Parihar |
| 2012/0203136 | A1 | 8/2012 | Hibner |
| 2016/0120573 | A1 | 5/2016 | Teufel et al. |

FOREIGN PATENT DOCUMENTS

| | | |
|---|---|---|
| DE | 202009003154 | 6/2009 |
| EP | 497520 | 8/1992 |
| EP | 1815798 | 8/2007 |
| WO | 97/20504 | 6/1997 |
| WO | 2006/020267 | 2/2006 |
| WO | 2009/045891 | 4/2009 |
| WO | 2010/081105 | 7/2010 |

OTHER PUBLICATIONS

European Extended Search Report for EP Patent Appln. No. 19217063.7 dated May 26, 2020, 5 pages.

PCT International Search Report and Written Opinion for International Application No. PCT/US2015/052004, Applicant Hologic, Inc., Forms PCT/ISA/210, 220, and 237, dated Dec. 9, 2015, (11 pages).

PCT International Preliminary Report on Patentability in Application PCT/US2015/052004, mailed Apr. 6, 2017, 7 pages.

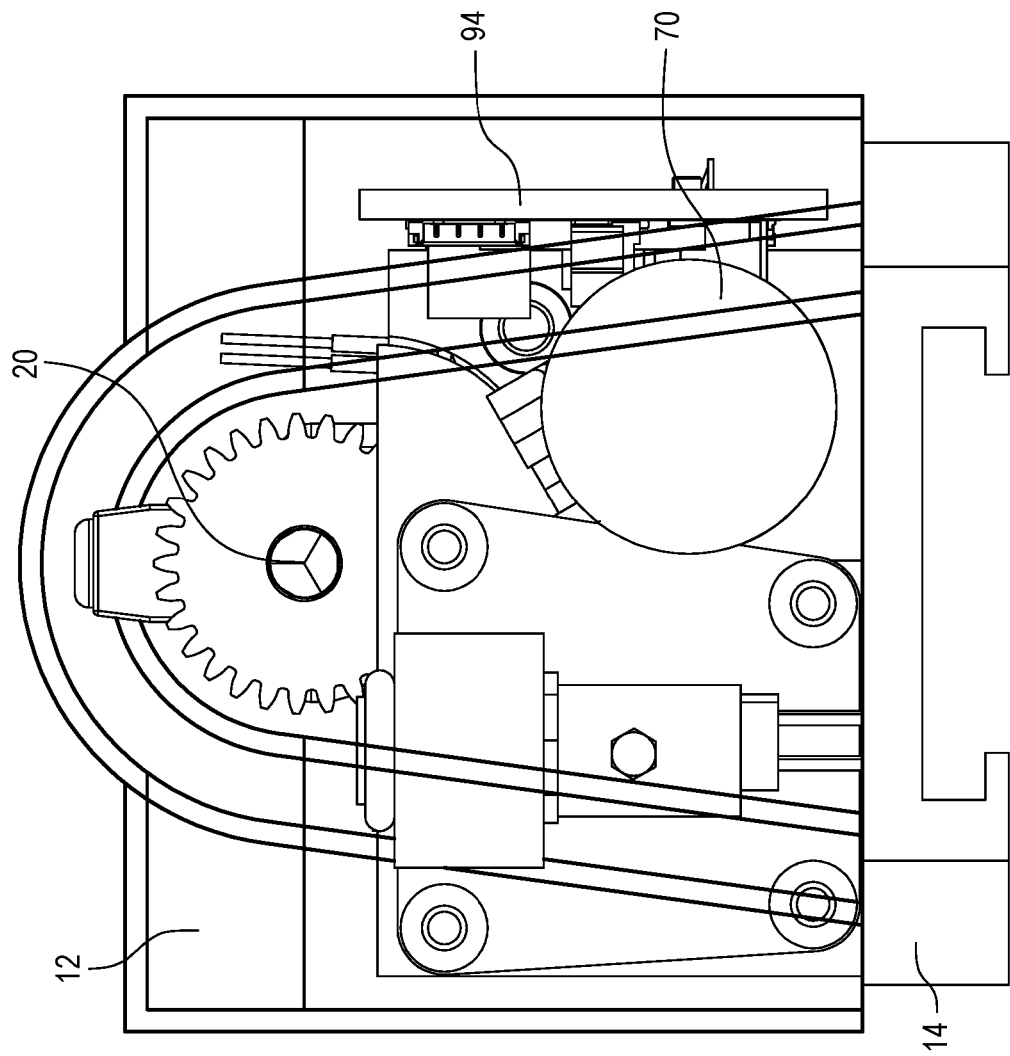

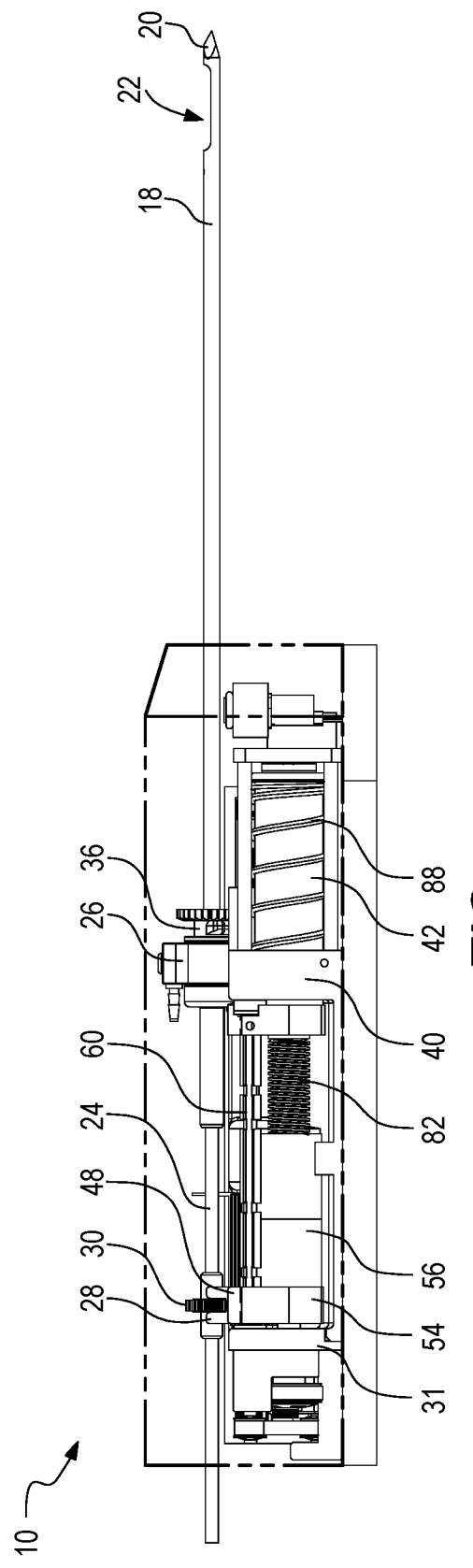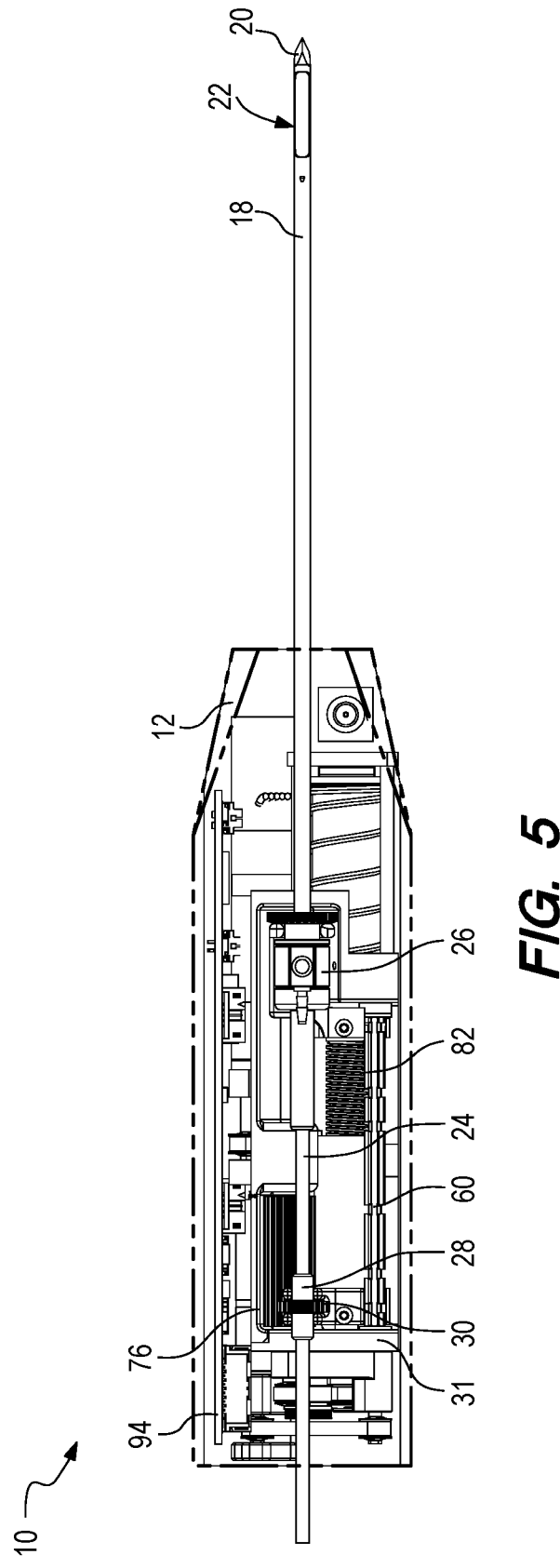

| step no. | step description | OC nut status | OC position | IC nut status | IC position |
|---|---|---|---|---|---|
| | shipping or home position | unlocked | full distal | unlocked | full distal |
| 102a | pre-arming | locked | full distal | unlocked | retracting proximally |
| 102b | pre-armed | locked | full distal | unlocked | full proximal |
| 104a | arming | unlocked | retracting proximally | locked | full proximal |
| 104b | armed | unlocked | full proximal | locked | full proximal |
| 106a | firing | unlocked | firing distally | unlocked | firing distally |
| 106b | fired | unlocked | full distal | unlocked | full distal |
| 108/ 110a | begin cutting stroke | locked | full distal | unlocked | retracting proximally |
| 110b | cutting stroke-IC retracted | locked | full distal | unlocked | full proximal |
| 112 | cutting stroke-IC advancing | locked | full distal | unlocked | advancing distally |
| 114 | cutting stroke-IC advanced/dwell | locked | full distal | unlocked | full distal |
| 116 | cutting stroke-IC retracting | locked | full distal | unlocked | retracting proximally |
| 110a | complete cutting stroke-IC retracted | locked | full distal | unlocked | full proximal |

*FIG. 20*

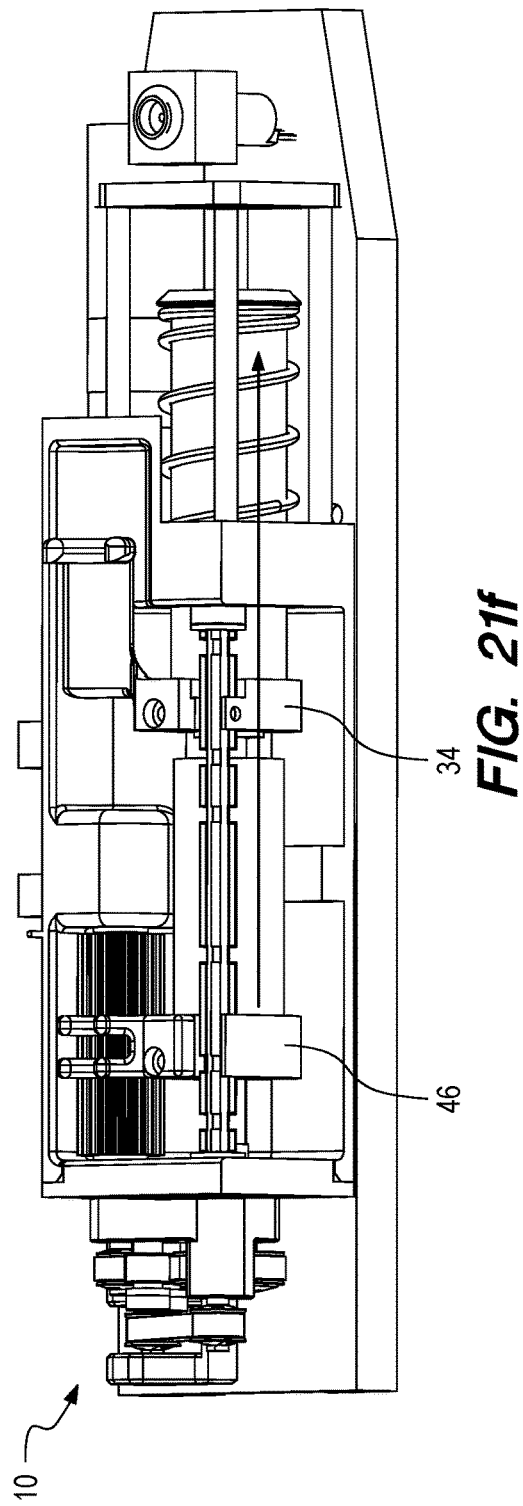
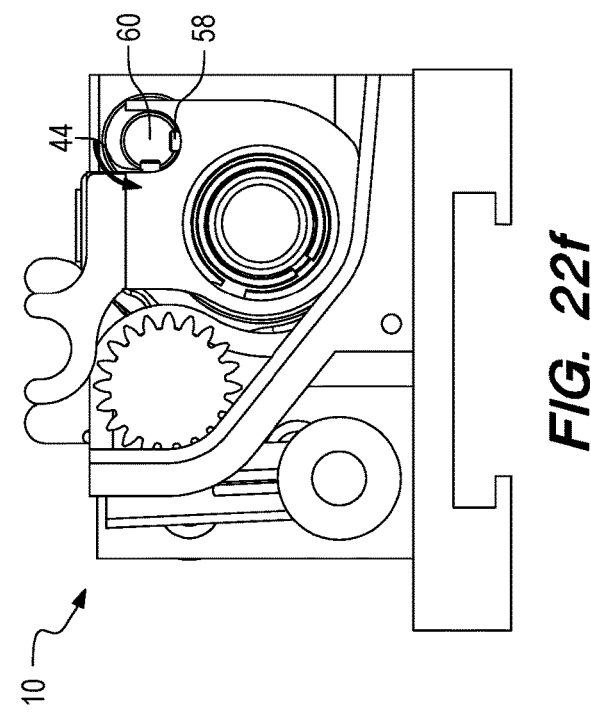

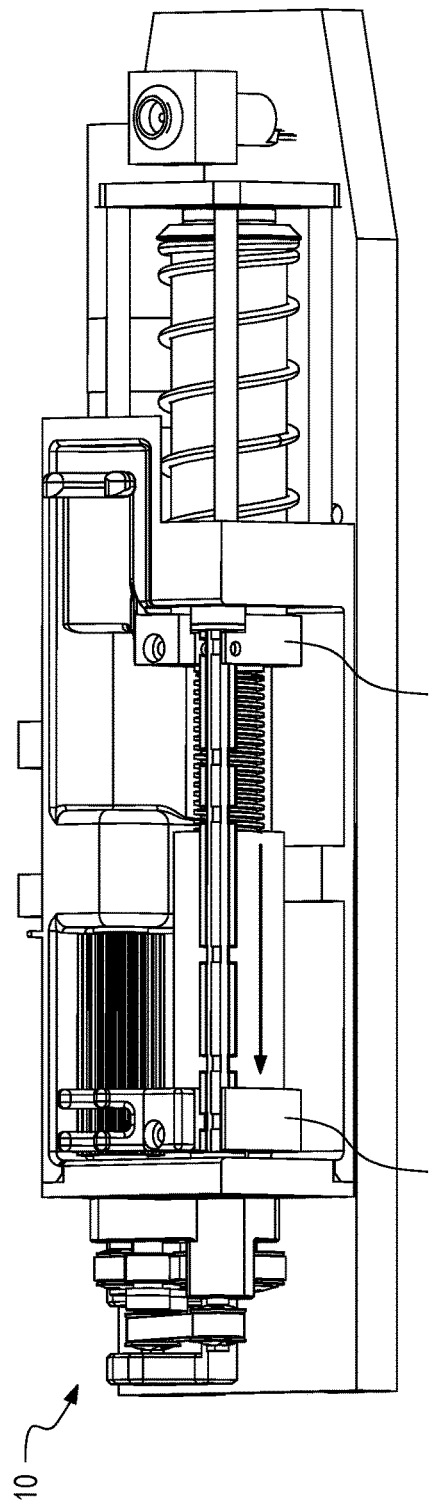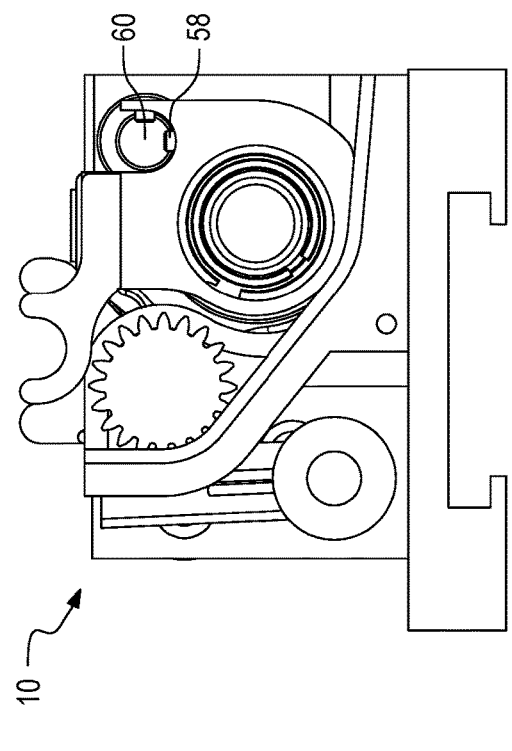

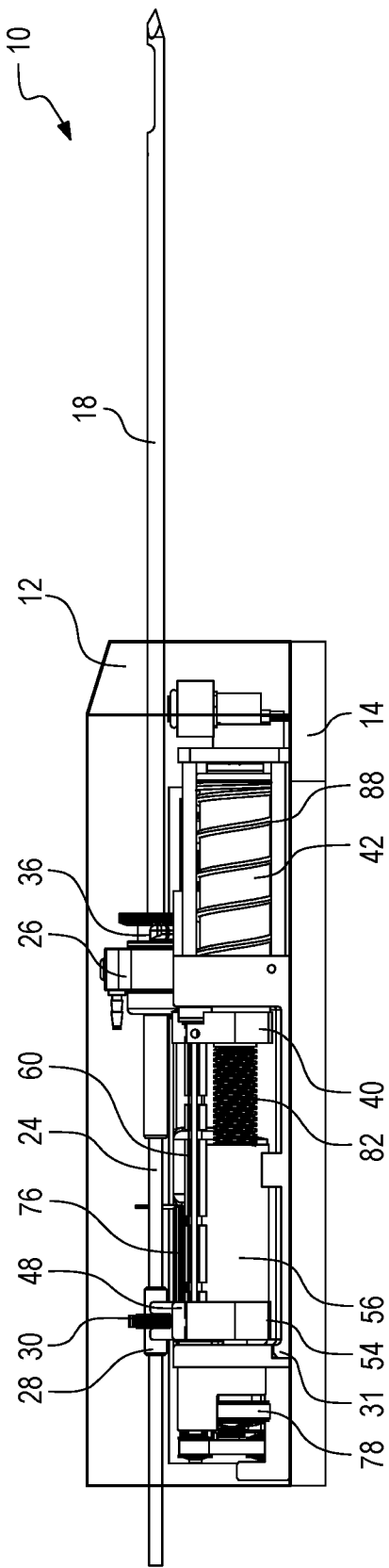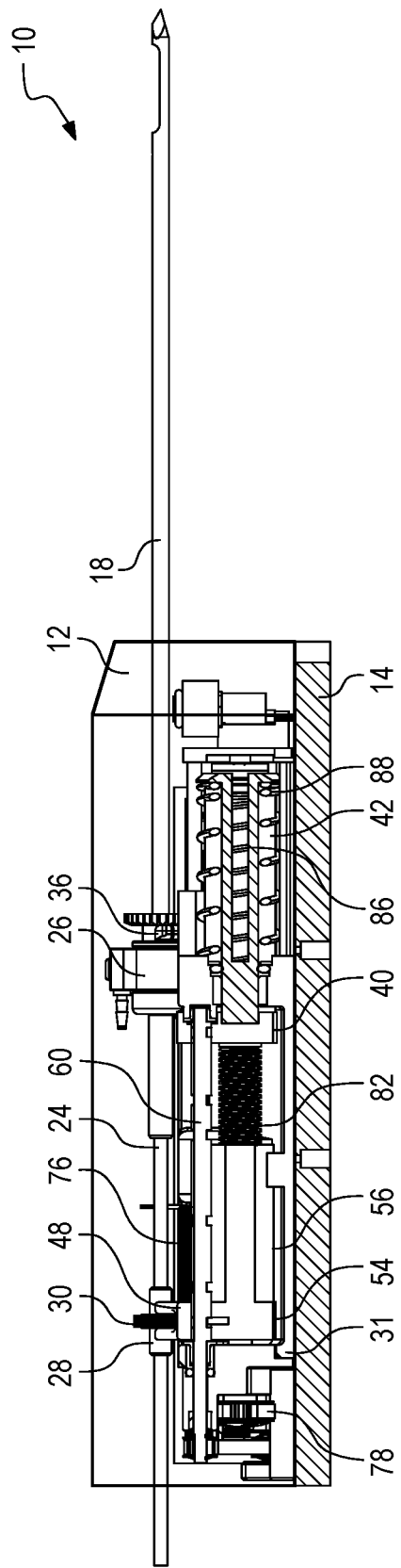

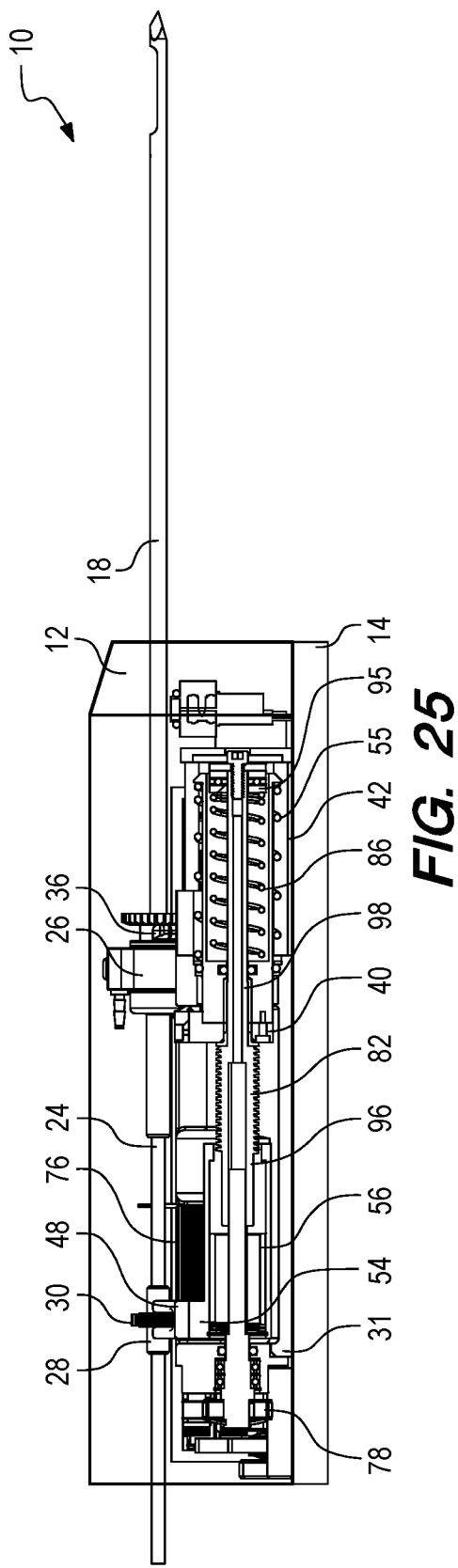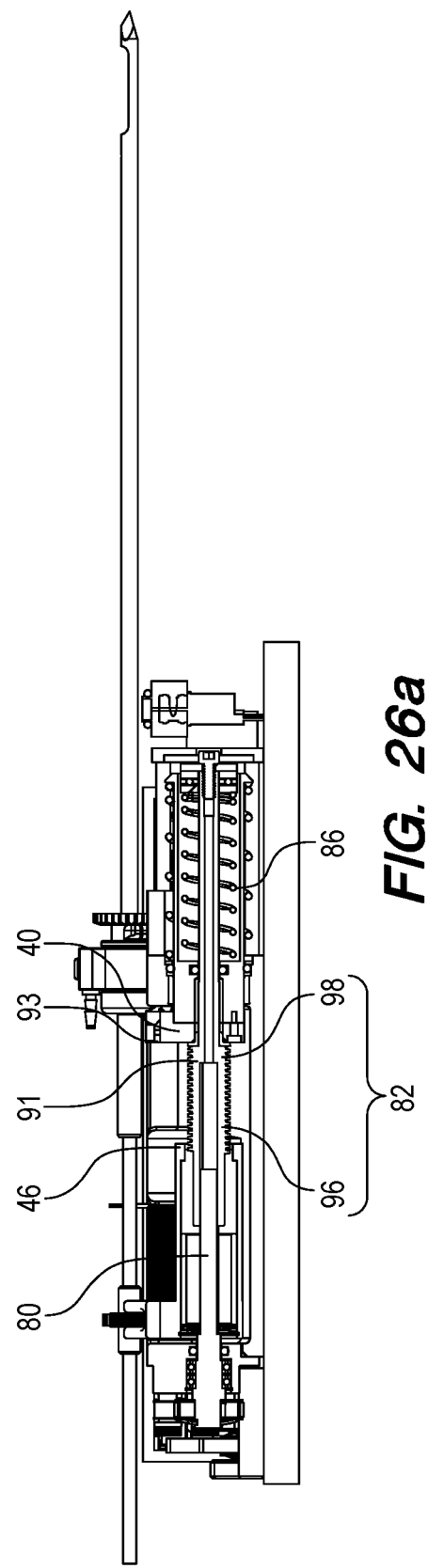

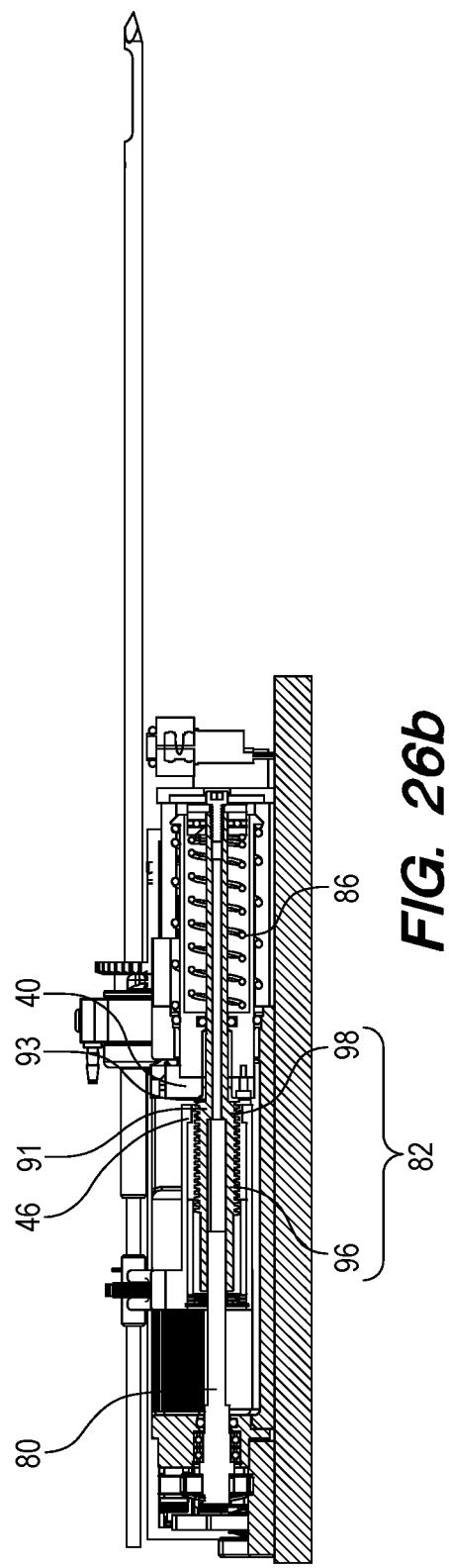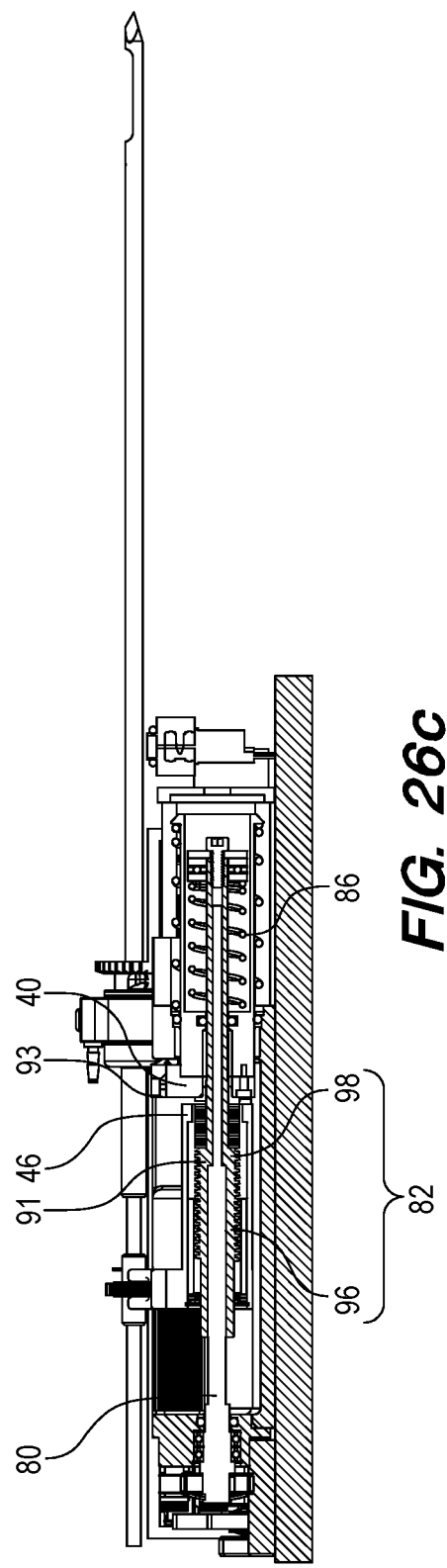

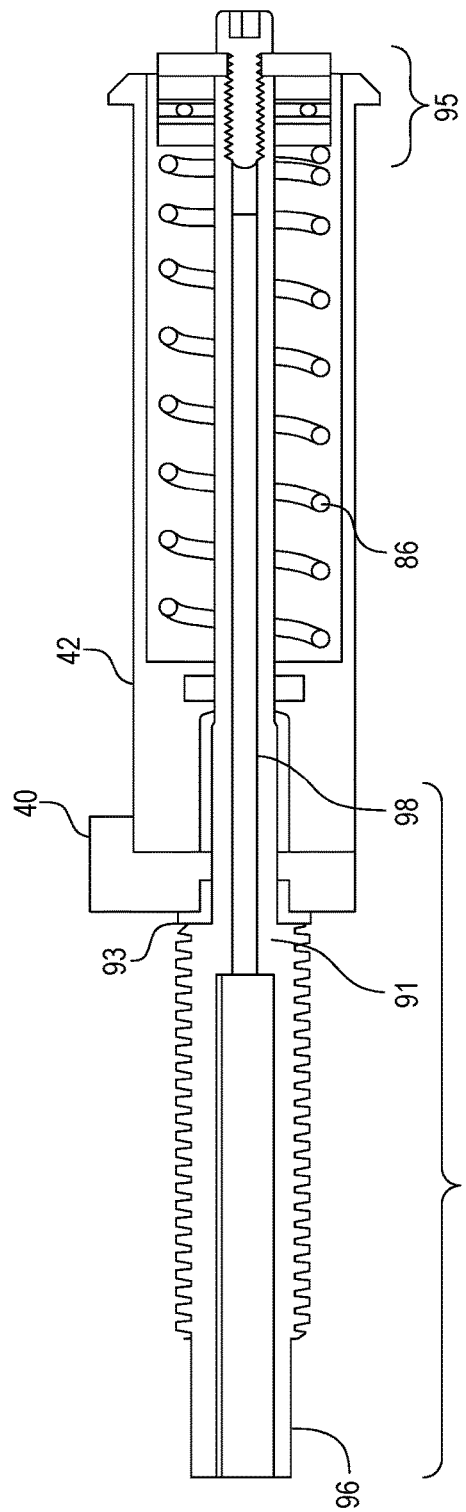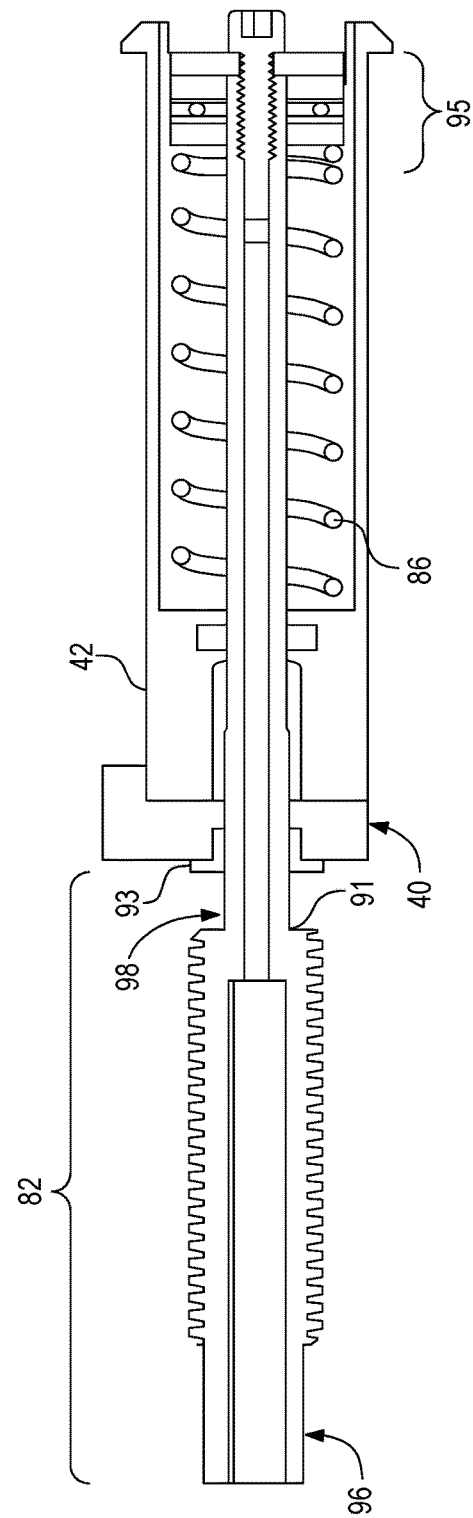

BIOPSY DEVICE

CROSS-REFERENCE TO RELATED APPLICATIONS

The present application is a continuation of U.S. patent application Ser. No. 16/032,784, filed Jul. 11, 2018, now U.S. Pat. No. 11,045,172, which application is a continuation of U.S. patent application Ser. No. 14/864,432, filed Sep. 24, 2015, now U.S. Pat. No. 10,022,110, which claims the benefit under 35 U.S.C. § 119 to U.S. provisional patent application Ser. No. 62/055,610, filed Sep. 25, 2014. The foregoing applications are hereby incorporated by reference into the present application in their entirety.

FIELD

The present disclosure generally relates to the field of tissue sampling and harvesting. More specifically, the disclosure relates to biopsy needle sets and devices.

BACKGROUND

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set. One known needle set includes an outer cannula having a pointed tip and a tissue receiving opening defined near its distal end, and an inner cannula having an open distal end surrounded by an annular cutting blade. The inner cannula is slidably disposed within the outer cannula so that it can close the tissue receiving opening, thereby cutting tissue prolapsing into the lumen of the outer cannula through the tissue receiving opening. Typically, a hub is connected to the proximal end of each needle. Such needle sets are used with or incorporated in various forms of biopsy devices, including motor driven biopsy devices.

Current motor driven biopsy devices present issues involving sterilization of the devices after use, which may lead to shorten device lifespan. Further, current biopsy devices are typically introduced into tissue with the tissue receiving opening in an open state, which increases drag during introduction into tissue.

SUMMARY

In accordance with one embodiment, a biopsy system driver includes a motor having a rotatable output shaft and a support structure. The biopsy system driver also includes a drive shaft rotatably coupled to the support structure. The drive shaft includes or is otherwise operatively connected to the motor output shaft such that activation of the motor rotates the drive shaft. The biopsy system driver further includes an elongate lead screw coupled to the drive shaft such that rotation of the drive shaft rotates the lead screw about an axis of the lead screw. The lead screw is axially translatable relative to the drive shaft and to the support structure. Moreover, the biopsy system driver includes a biopsy instrument drive member threadably coupled to the lead screw such that rotation of the lead screw causes axial translation of one of the lead screw and biopsy instrument drive member relative to the other one and to the support structure.

In one or more embodiments, the motor is coupled to the support structure. The support structure may include or otherwise be coupled to a drive unit housing. The drive shaft may include an adapter operatively coupled to the motor output shaft, the lead screw having a proximal axial inner bore into which a distal portion of the adapter extends, wherein the lead screw may axially translate over the distal portion of the adapter.

In one or more embodiments, the motor is a reversible output direction motor such that activation of the motor in a first motor output direction causes a corresponding rotation of the lead screw in a first rotational direction about the lead screw axis. Also, activation of the motor in a second motor output direction, opposite the first motor output direction, causes a corresponding rotation of the lead screw in a second rotational direction, opposite the first rotational direction, about the lead screw axis. The biopsy system driver may include an elongate cam rotatably coupled to the support structure, wherein the cam is selectively rotatable to engage and thereby prevent axial translation of the biopsy instrument drive member relative to the lead screw and support structure.

In one or more embodiments, the biopsy system driver includes a dwell spring assembly coupled to the lead screw. The dwell spring assembly may include a cylindrical dwell spring holder having a dwell spring seated therein. A reduced diameter distal extension portion of the lead screw may extend through an opening in a proximal end wall of the dwell spring holder, and through a lumen of the dwell spring, respectively, and may be connected to a thrust bearing plate adjacent a distal end of the dwell spring. The dwell spring may be sized and configured such that, when the dwell spring holder is fixed to the support structure, the dwell spring resists compression between the thrust bearing plate and proximal end wall of the dwell spring holder sufficient to thereby maintain the lead screw in a fixed position relative to the respective dwell spring holder and support structure during activation of the motor, so long as the biopsy instrument drive member may move freely relative to the lead screw.

In one or more embodiments, biopsy system driver includes a distal drive member stop that engages and thereby prevents advancement the biopsy instrument drive member in a distal direction relative to the support structure beyond the distal drive member stop. The dwell spring may be sized and configured such that, when the dwell spring holder is fixed to the support structure, and activation of the motor in a given output direction advances the biopsy instrument drive member relative to the lead screw until the biopsy instrument drive member reaches and stops against the distal drive member stop, the dwell spring is compressed by the proximally advancing thrust bearing plate as the lead screw moves proximally relative to the biopsy instrument drive member. The biopsy system driver may also include a controller configured to reverse the output direction of the motor after a predetermined time period following when the biopsy instrument drive member engages the distal drive member stop In one or more embodiments, the biopsy system driver may include an elongate cam rotatably mounted to the support structure. The cam may have a first rotational position in which the cam engages and fixes an axial position of the dwell spring holder relative to the support structure, while allowing the biopsy instrument drive member to axially translate relative to the support structure when the motor is actuated. The cam may be operatively coupled to a motorized cam driver that is processor-controlled to selectively rotate the cam into and out of respective positions in which the cam locks and thereby fixes a position of one, both, or neither of the biopsy instrument drive member and dwell spring holder relative to the support structure. The biopsy instrument drive member may include an inner cutting cannula drive member, and an outer cannula drive member attached to the dwell spring holder. The dwell spring holder may not be fixed to the support structure. The outer cannula drive member may be slidably movable relative to the support structure between a distal fired position and a proximal armed position.

In one or more embodiments, the biopsy system driver includes a firing spring interposed with the outer cannula drive member, where the firing spring is in a substantially fully expanded and unloaded configuration when the outer cannula drive member is in the distal fired position, and in a compressed and loaded configuration when the outer cannula drive member is in the proximal armed position. The dwell spring may be stronger than the firing spring so as to resist compression, thereby maintaining a substantially fixed position relative to the lead screw as the outer cannula drive member is moved from the distal fired position to the proximal armed position.

In one or more embodiments, the respective inner and outer cannula drive members may be armed and fired by: (1) moving the cam to a first rotational position in which the dwell spring holder is locked in position relative to the support structure, while allowing translation of the inner cannula drive member relative to the lead screw; (2) activating the motor in a respective first output direction to move the inner cannula drive member proximally relative to the lead screw until the inner cannula drive member reaches an inner cannula proximal armed position; (3) moving the cam to a second rotational position in which the inner cannula drive member is locked in place at the inner cannula proximal armed position, while allowing translation of the respective lead screw, dwell spring holder and outer cannula drive member relative to the inner cannula drive member; (4) activating the motor in a respective second output direction opposite the respective first output direction to move the respective lead screw, dwell spring holder and outer cannula drive member proximally relative to the inner cannula drive member, until the outer cannula drive member reaches an outer cannula proximal armed position, thereby compressing and loading the firing spring; and (5) moving the cam to a third position in which neither one of the inner cannula and dwell spring holder is locked to the support structure, thereby allowing the firing spring to restore to its substantially uncompressed and unloaded condition.

In one or more embodiments, a biopsy system includes a biopsy system driver and a biopsy needle set removably coupled to the support structure. The biopsy needle set may include an outer cannula and an inner cannula at least partially positioned in an axial lumen of the outer cannula, with a proximal portion of the outer cannula being removably coupled to the outer cannula drive member, and a proximal portion of the inner cannula being removably coupled to the inner cannula drive member. The biopsy system may include a pinion gear operatively coupled to the motor output shaft, where a spur gear disposed circumferentially about a proximal end portion of the inner cannula engages the pinion gear, such that activation of the motor in either output direction rotates the inner cannula.

In one or more embodiments, the biopsy system driver or biopsy system includes a plurality of encoding discs and a plurality of sensors. Each encoding disc of the plurality of encoding discs may be coupled to the elongate cam such that rotation of the elongate cam results in corresponding rotation of each encoding disc of the plurality of encoding discs. Each sensor of the plurality of sensors may be coupled to the support structure and being operatively coupled to a respective encoding disc from the plurality of encoding discs. Each sensor of the plurality of encoding discs is configured to detect a rotational position of a respective encoding disc, to thereby determine a rotational position of the elongate cam.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1 to 7 are various perspective views of a two-part biopsy device, according to one embodiment, with various components shown in phantom for clarity.

FIG. 20 is a table summarizing the positions of various components of a biopsy device during the biopsy procedure depicted in FIG. 19.

FIGS. 21a to 21m and 22a to 22m are schematic views of various components of a biopsy during the biopsy procedure depicted in FIG. 19.

FIGS. 23 to 25 are side and side cross-sectional views of the two-part biopsy device depicted in FIGS. 1 to 7, with various components shown in phantom for clarity.

FIGS. 26a to 26c, 29 and 30 are side cross-sectional view of a two-part biopsy device according to one embodiment during various points in the cutting cycle, with various components shown in phantom for clarity. In FIG. 26a, the biopsy device is in the middle of a cutting cycle (described below), and the lead screw is in an axial translation mode (described below). In FIG. 26b, the biopsy device is in the beginning or end of a dwell period (described below), and the lead screw is in an axial translation mode (described below). In FIG. 26c, the biopsy device is in the middle of a dwell period (described below) and the lead screw is in a dwell mode (described below). In FIG. 29, the lead screw is in an axial translation mode (described below). In FIG. 30, the lead screw is in a dwell mode (described below).

In FIG. 37, the sliding support member is shown in phantom for clarity.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1 to 7 depict various views of a two-part biopsy device 10, with the housing 12 shown in phantom to allow depiction of internal components. The biopsy device 10 also includes a base plate 14 for mounting onto a stabilized surface, such as a stereotactic biopsy table.

Figure 1:
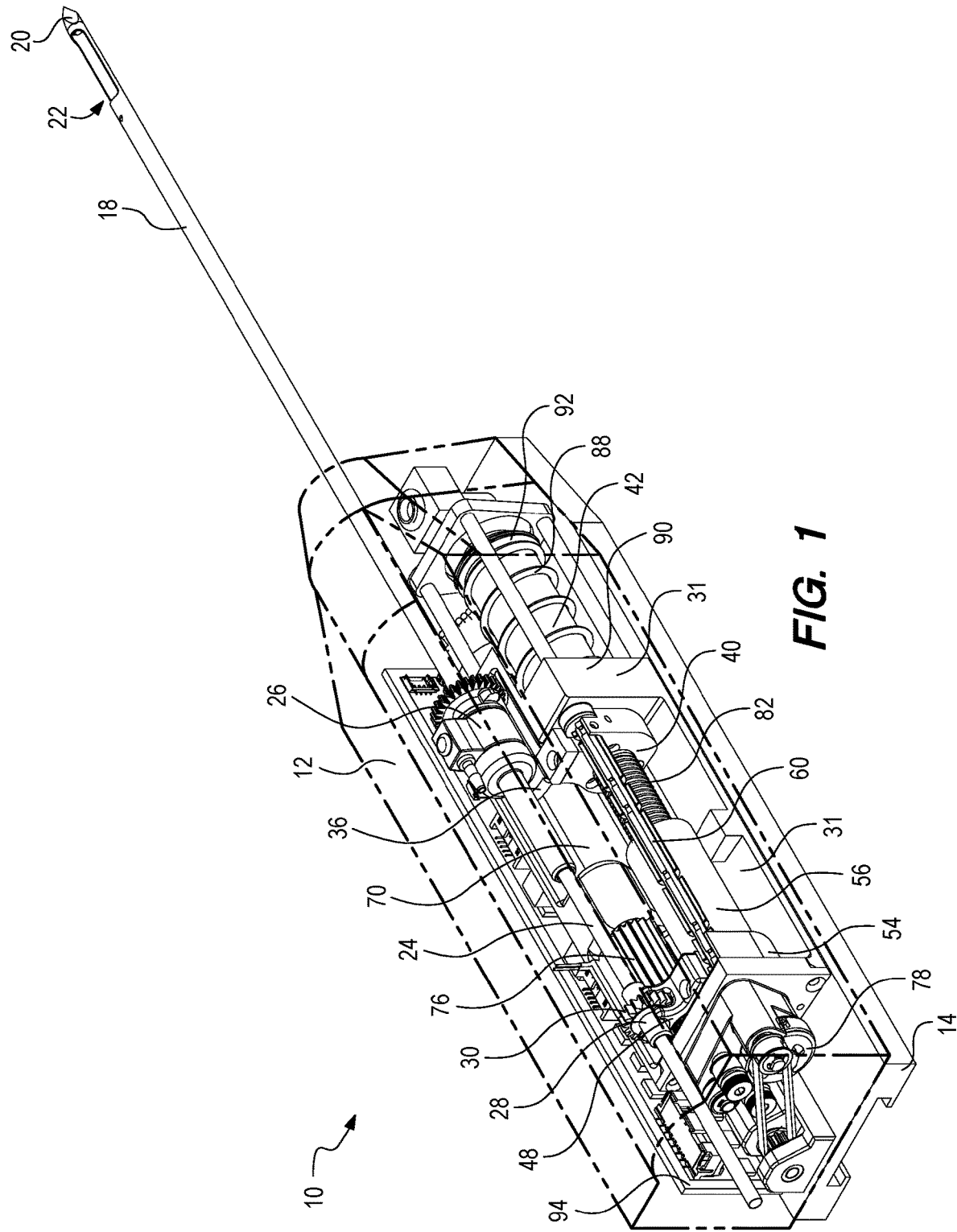
Figure 2:
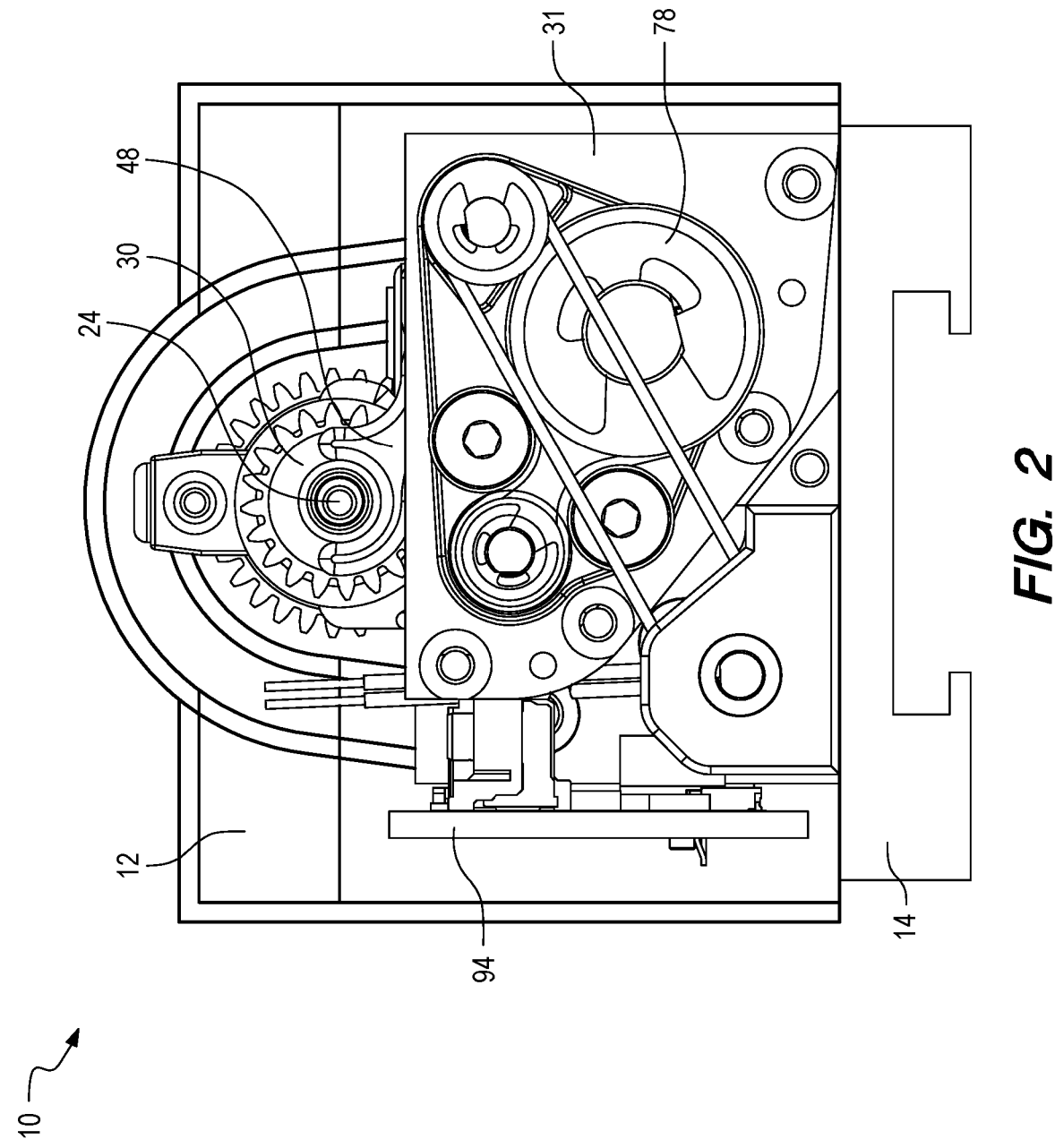
Figure 6:
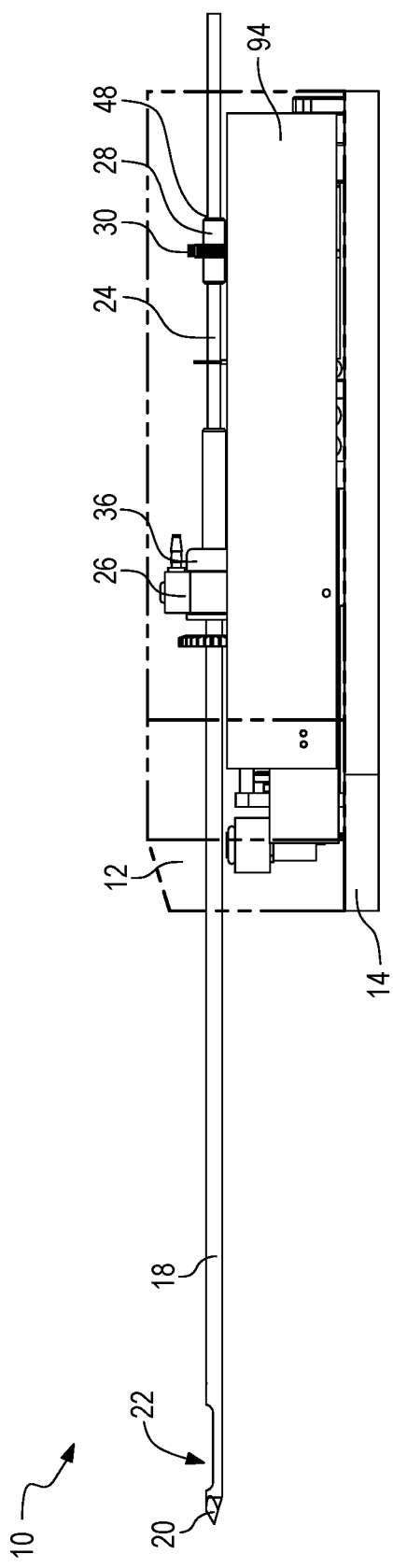
Figure 7:
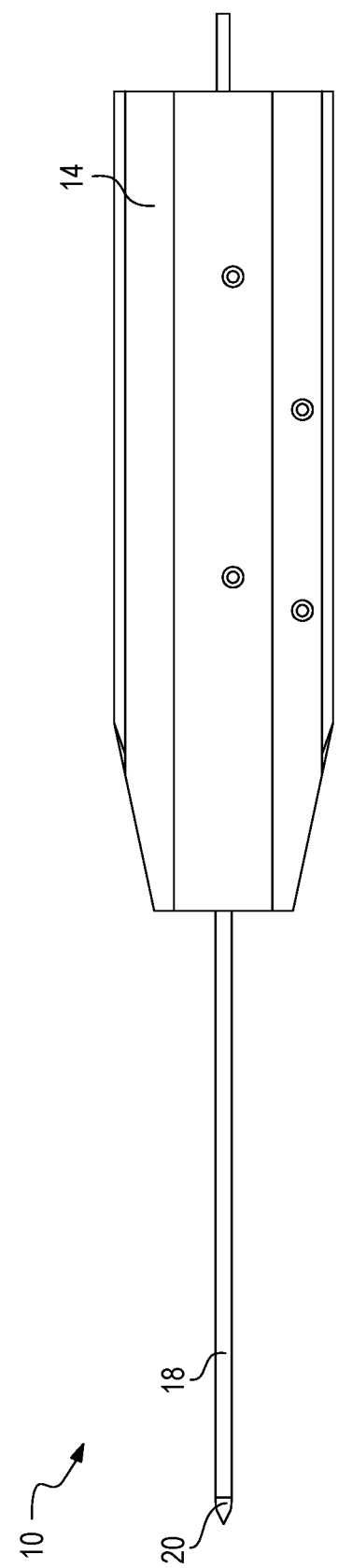
Figure 8:
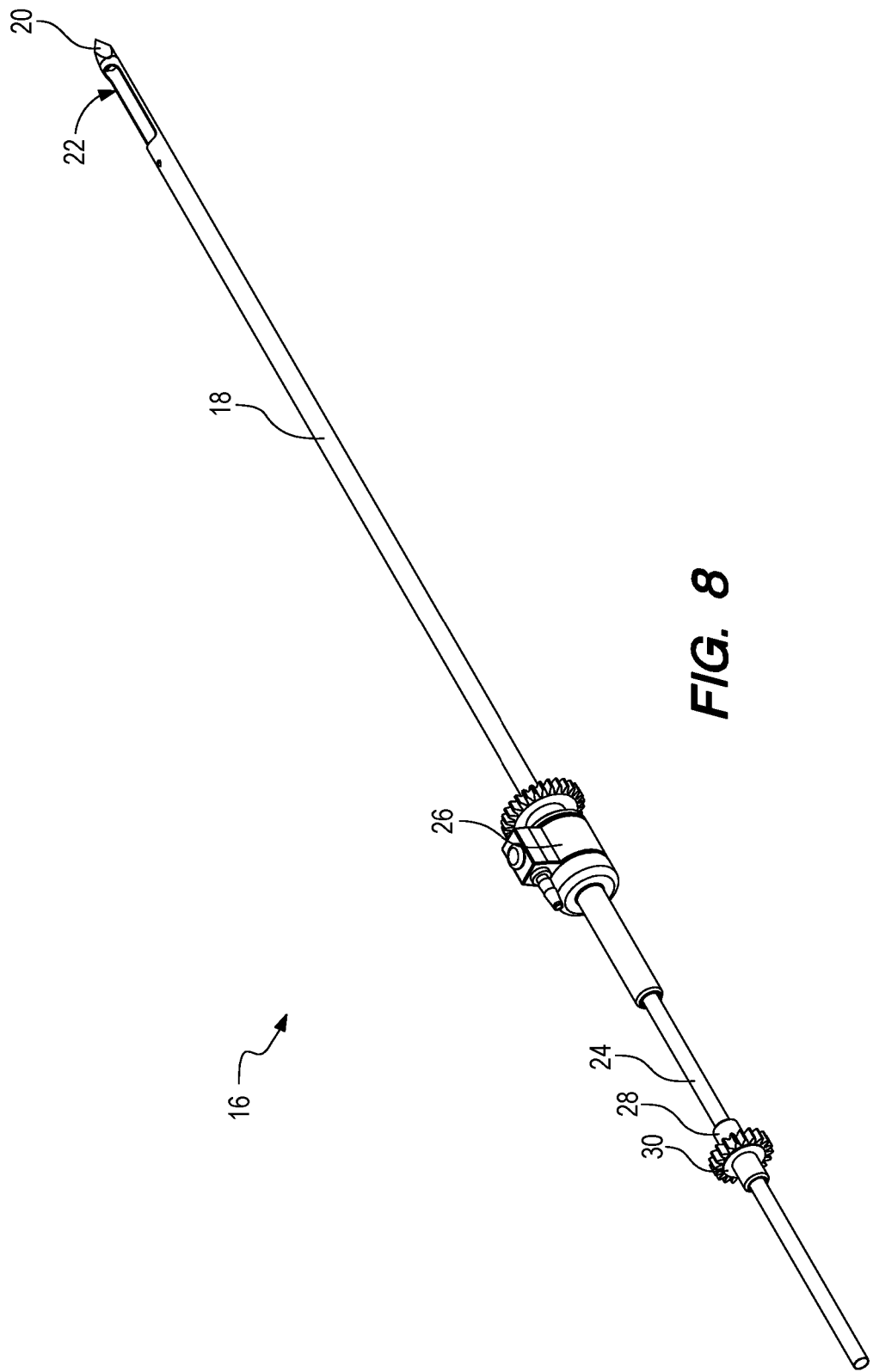
FIG. 8 is a perspective view of the inner and outer needle of the disposable portion of the two-part biopsy device depicted in FIGS. 1 to 7.

The two-part biopsy device 10 has a "disposable portion" 16, a part of which is depicted in FIG. 8. The disposable portion 16 is configured to be discarded after a single use. The disposable portion 16 includes an outer cannula 18 having a distal tissue piercing tip 20 and defining a tissue receiving opening 22 adjacent to the distal tissue piercing tip 20. A cutting board 11 is disposed in the lumen of the outer cannula 18 distal to the tissue receiving opening 22. The outer cannula 18 is rotatable to position the tissue receiving opening 22 adjacent tissue to be biopsied. Rotation of the outer cannula 18 can be driven manually via gears and shafts. Alternatively, rotation of the outer cannula 18 can be driven by a dedicated motor, for instance in non-firing biopsy devices. In another alternative embodiment, rotation of the outer cannula 18 can be driven by lead screw (described below). In yet another alternative embodiment, rotation of the outer cannula 18 can be driven by rotation of the inner cannula 24 (described below). These last two embodiments would result in automatic rotation of the outer cannula 18 that is linked to the cutting cycle.

The disposable portion 16 also includes an inner cannula 24 slidably disposed in the outer cannula 18, and having an open distal end surrounded by an annular cutting blade. When the inner cannula 24 is positioned with its open distal end in contact with the cutting board 11, the inner cannula 24 closes the tissue receiving opening 22 in the outer cannula 18. Further, the disposable portion 16 includes a top part of the housing 12, which snaps together with a bottom part of the housing 12 to temporarily secure the disposable portion 16 to a "reusable portion 32," described below.

Figure 27:
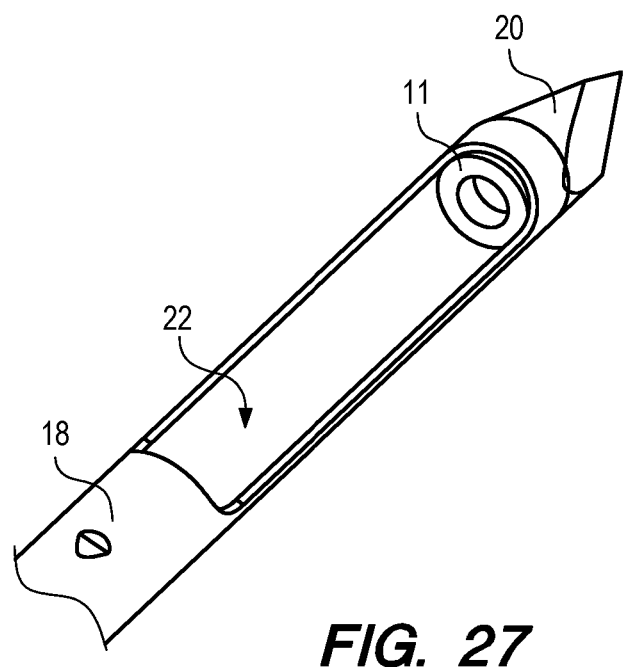
FIGS. 27 and 28 are perspective and side cross-section views of the distal end of an outer cannula according to one embodiment.
Figure 28:
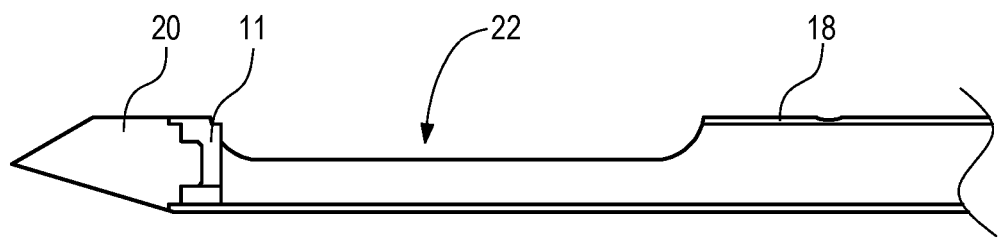

As shown in FIGS. 27 and 28, the cutting board 11 is configured to seal the open distal end of the inner cannula 24 when the inner cannula 24 is in contact with the cutting board 11. This seal prevents fluids introduced into the lumen of the outer cannula 18 from being aspirated through the open distal end and lumen of the inner cannula 24 and bypassing the biopsy site. Instead, the fluids are directed toward the tissue through the tissue receiving opening 22.

The disposable portion 16 also includes an outer cannula hub 26 coupled to the outer cannula 18. Further, the disposable portion 16 includes an inner cannula hub 28 and an inner cannula gear 30, which are each coupled to the inner cannula 24. The outer cannula hub 26, inner cannula hub 28 and inner cannula gear 30 are configured to be operatively coupled to corresponding components of a "reusable portion" 32 of the biopsy device 10, to thereby facilitate movement of the outer and inner cannulas 18, 24. The outer cannula hub 26 also allows for the administration of medication (e.g., anesthetic), saline, and/or air for lavage and aspiration.

In an alternative embodiment, the inner cannula 24 does not contact the cutting board 11 during normal cutting, but is configured to be selectively moved into contact with the cutting board 11 to seal the open distal end of the inner cannula 24. In other alternative embodiments, the open distal end of the inner cannula 24 can be sealed with the following alternative components disposed in the distal end of the outer cannula 18: a tapered plug; a pre-grooved cutting board that creates a tortuous fluid path thereon; a "mushroom top" plug made from soft, deformable material; and a movable cutting board supported by a spring or a compliant material. In yet another alternative embodiment, an O-ring can be disposed in the distal end of the outer cannula 18 to seal the open distal end of the inner cannula 24, which passes therethrough. All of the above-described alternatives to the cutting board 11 prevent dulling of the annular blade at the distal end of the inner cannula 24 while maintaining a substantially fluid tight seal around the distal end of the inner cannula 24.

Figure 31:
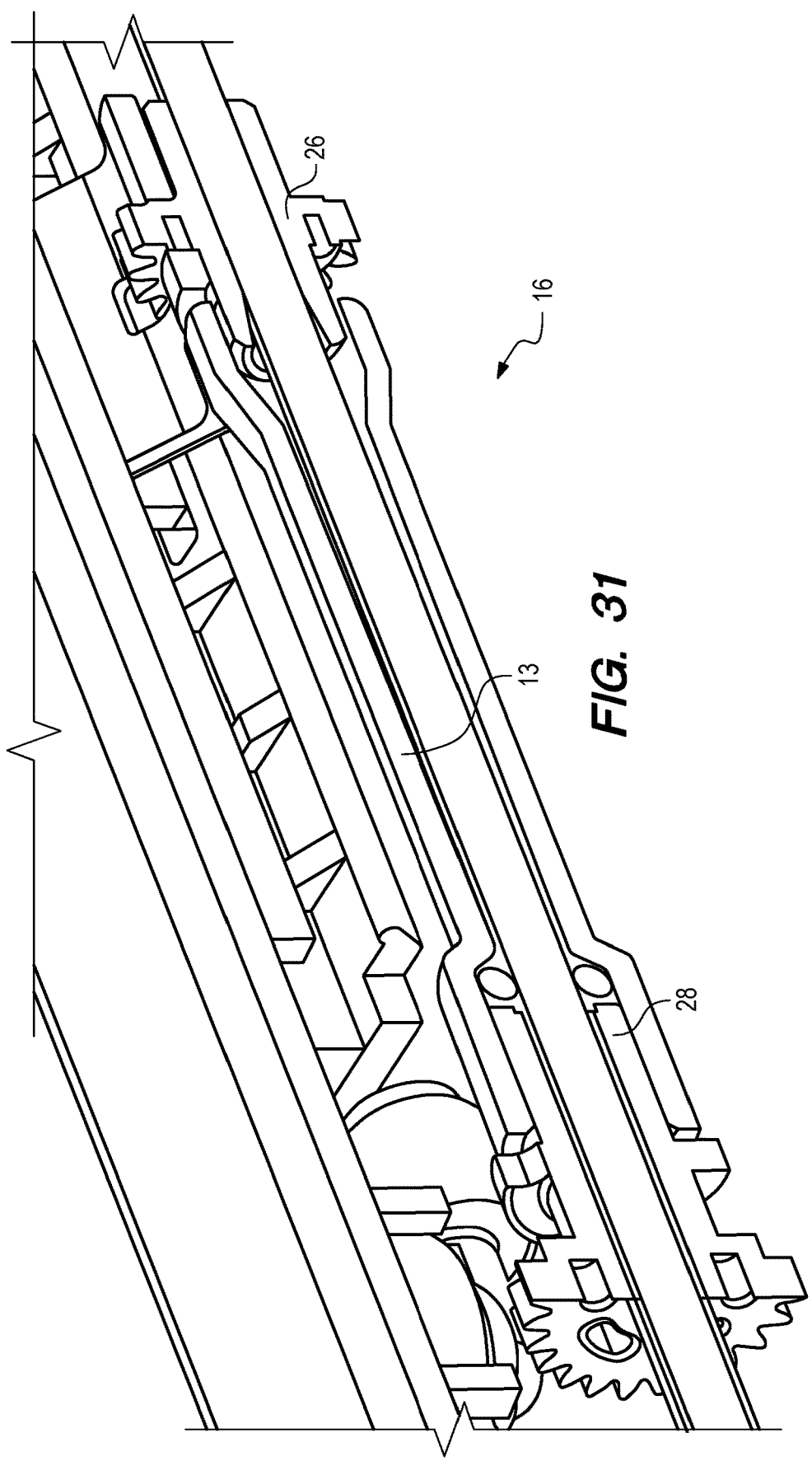
FIG. 31 is a detailed longitudinal cross-sectional view of a disposable portion of the biopsy device depicted in FIGS. 1 to 7, with various components omitted for clarity.

The biopsy device 10 also includes a seal sleeve 13 disposed in the disposable portion 16 between the outer and inner cannula hubs 26, 28 to fix the minimum distance therebetween, as shown in FIG. 31. The seal sleeve 13 is fixed to the outer cannula hub 26 and interferes with the inner cannula hub 28. The seal sleeve 13 also fixes the minimum distance between the respective distal ends of the outer and inner cannulas 18, 24, and therefore the amount of overlap between the distal end of the inner cannula 24 and the cutting board 11. Too much overlap can cause premature dulling of the annular blade around the distal end of the inner cannula 24. Too little and too much overlap can negatively affect biopsy quality. In one embodiment, the acceptable range of overlap is 0.002 inches to 0.025 inches. In an alternative embodiment, a component analogous to the seal sleeve fixes the minimum distance between the outer and inner cannula drive assemblies 34, 46. In another embodiment, there is no seal sleeve, but a resilient material (e.g., UHMWPE) is disposed between the cutting board 11 and the closed distal end of the outer cannula 18. The resilient material allows the cutting board 11 to be displaced distally by the force of the inner cannula 24. The amount of displacement can be chosen to optimize the overlap, which optimizes cutting efficiency while preserving the cutting ability of the annular blade at the distal end of the inner cannula 24.

The disposable portion 16 of the biopsy device 10 can also be manufactured using a fixture which holds the outer and inner cannulas 18, 24 relative to each other at the preferred distance between the distal end of the inner cannula 24 and the cutting board 11 in the outer cannula 18 before attaching one or more gears to the outer and inner cannulas 18, 24. In one embodiment, the acceptable overlap between the distal end of the inner cannula 24 and the cutting board 11 is about 0.002" to about 0.025". Attaching the gears to the outer and inner cannulas 18, 24 fixes the relative positions of the outer and inner cannulas 18, 24 when the disposable portion 16 is attached to the reusable portion 32 and the outer and inner cannula drive assemblies 34, 46 are at their respective distal-most positions. This manufacturing process allows for less tight tolerance on supply materials.

Figure 9:
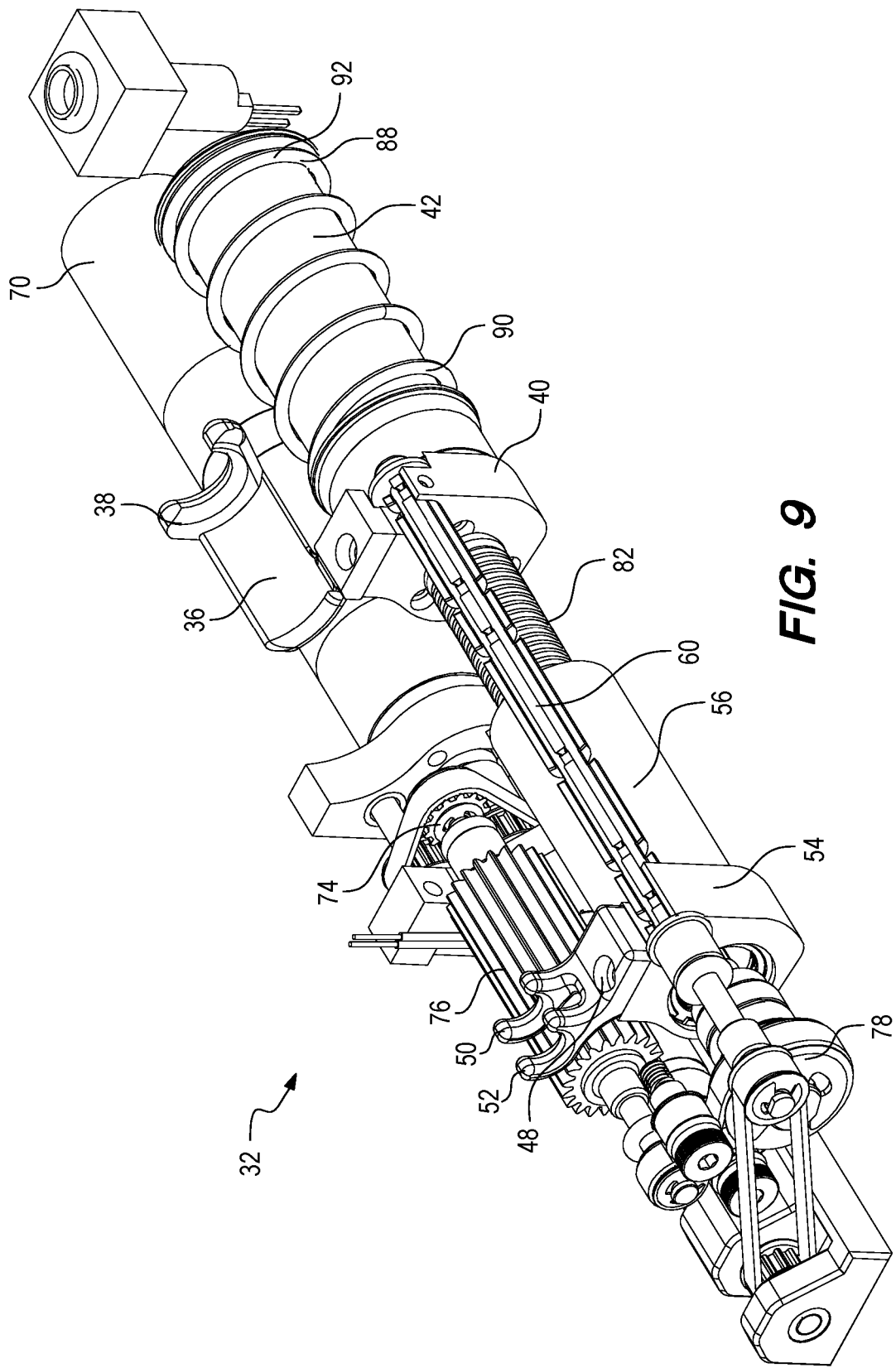
FIG. 9 is a perspective view of the reusable portion of the two-part biopsy device depicted in FIGS. 1 to 7, with various components omitted and other shown in phantom for clarity.

As mentioned above, the biopsy device 10 includes a reusable portion 32, depicted in FIG. 9, which is configured to be reused after a biopsy procedure. During that biopsy procedure, the reusable portion 32 is operatively coupled to the disposable portion 16, and drives axial movement of the outer and inner cannulas 18, 24. The reusable portion 32 also drives rotational movement of the inner cannula 24. The reusable portion 32 includes a bottom part of the housing 12, which snaps together with the top part of the housing 12 to temporarily secure to reusable portion 32 the disposable portion 16. Further, the reusable portion 32 includes a frame 31, which is secured to the housing 12, and to which the other components of the reusable portion 32 are secured, as shown in FIGS. 1, 2, 4 and 5.

Figure 10:
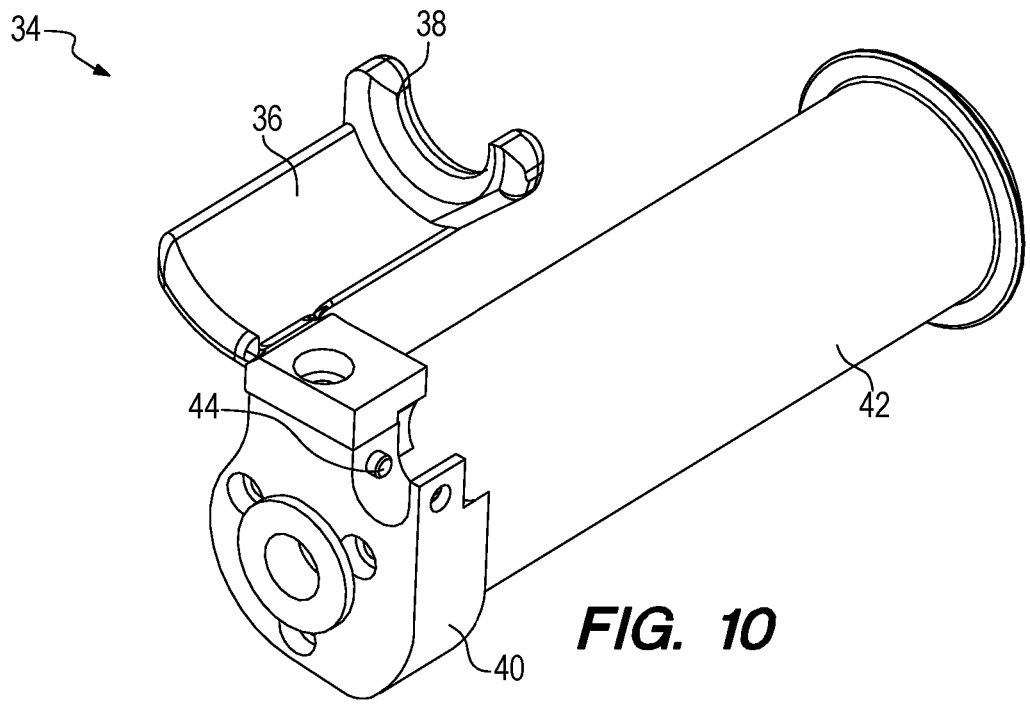
FIG. 10 is a perspective view of the outer cannula drive assembly of the two-part biopsy device depicted in FIGS. 1 to 7.

The reusable portion 32 includes an outer cannula drive assembly 34, depicted in FIG. 10, which is configured to operatively couple to the outer cannula hub 26 and to drive axial movement of the outer cannula 18. The outer cannula drive assembly 34 includes an outer cannula fork 36, which is configured to operatively couple to the outer cannula hub 26. The outer cannula fork 36 includes a distal lip 38 configured to transmit axial force to the outer cannula hub 26 in a proximal direction during arming and in a distal direction during firing (described below).

The outer cannula drive assembly 34 also includes an outer cannula nut 40 configured to couple the outer cannula fork 36 to an outer cannula sleeve 42. The outer cannula nut 40 and the outer cannula sleeve 42 are configured to ride on an axle (described below). The outer cannula drive assembly 34 further includes an outer cannula dowel 44 configured to releasably and operatively couple to a cam to control movement of the outer cannula drive assembly 34 and the outer cannula 18, as described below. Each of the outer and inner cannula drive assemblies 34, 46 may be generally referred to as a biopsy instrument drive member.

The reusable portion 32 can also be used with alternative disposable portions that include alternative outer cannulas with blunt ends. Such outer cannulas are not fired, but rather inserted, into the patient. Accordingly, in such alternative disposable portions, the alternative outer cannula hubs are not configured to mate with the outer cannula drive assembly 34 in the reusable portion 32. Alternatively, such alternative disposable portions can include a mechanical feature that prevents the reusable portion 32 from arming.

Figure 11:
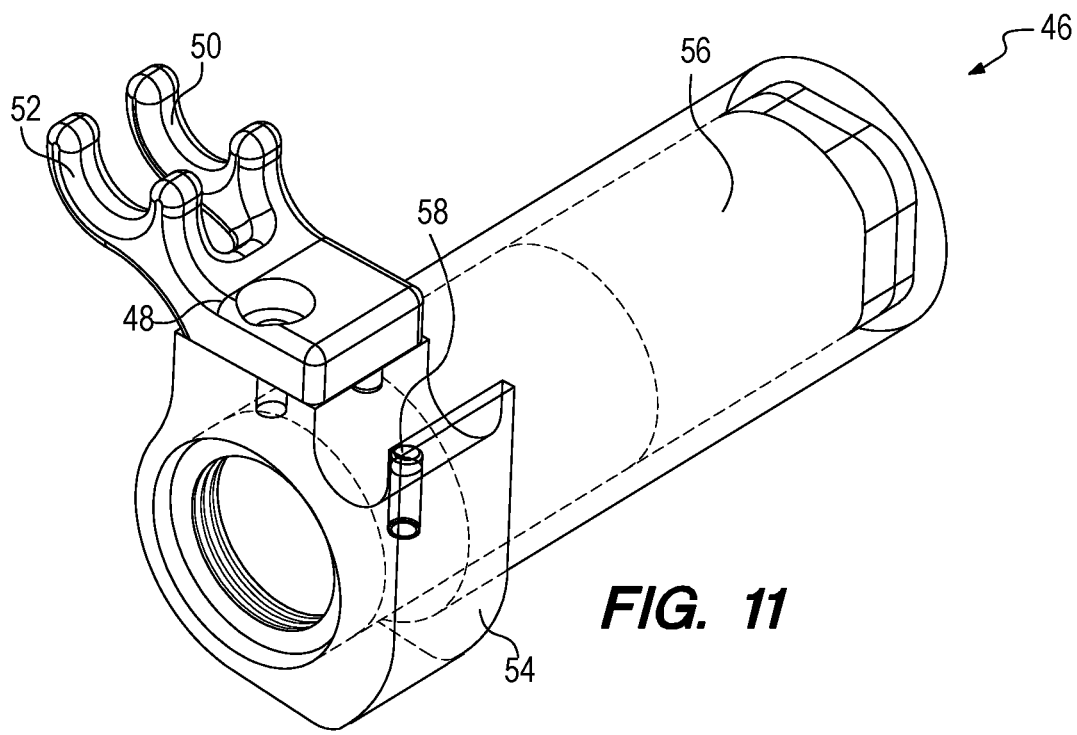
FIG. 11 is a perspective view of the inner cannula drive assembly of the two-part biopsy device depicted in FIGS. 1 to 7, with various components shown in phantom for clarity.

The reusable portion 32 also includes an inner cannula drive assembly 46, depicted in FIG. 11, which is configured to operatively couple to the inner cannula hub 28 and to drive axial movement of the inner cannula 24. The inner cannula drive assembly 46 includes an inner cannula fork 48, which is configured to operatively couple to the inner cannula hub 28. The inner cannula fork 48 includes distal and proximal lips 50, 52 configured to transmit axial force to the inner cannula hub 28 in proximal and distal directions, respectively.

Figure 17:
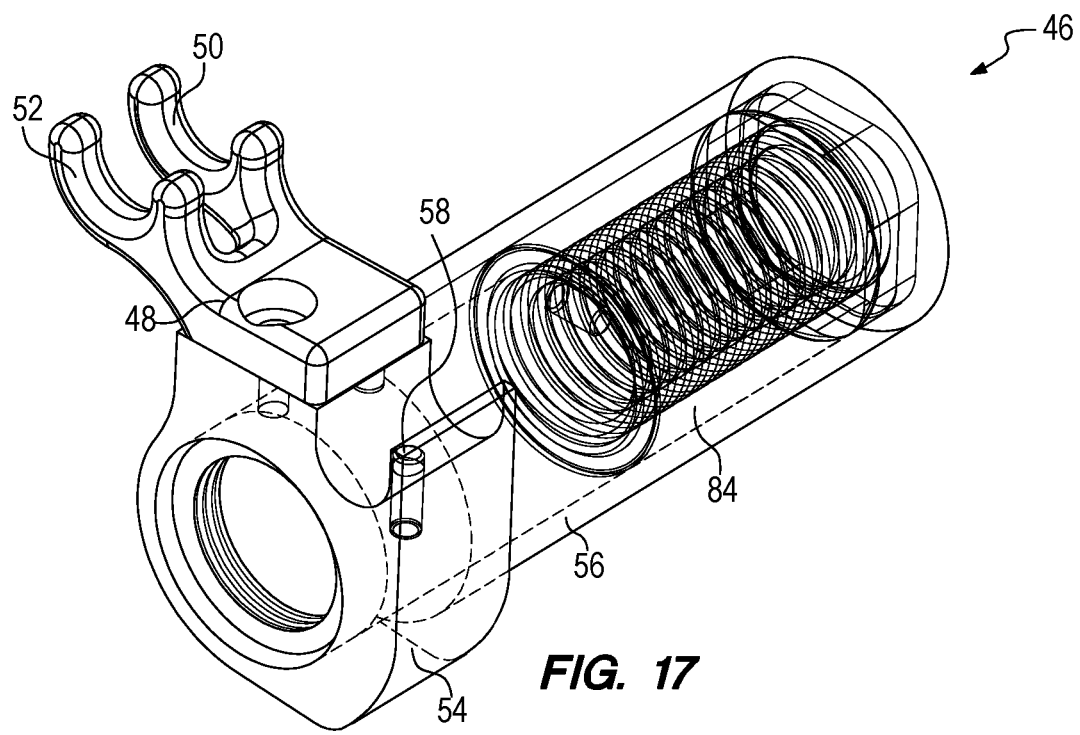
FIG. 17 is a perspective view of the inner cannula drive assembly of the two-part biopsy device depicted in FIGS. 1 to 7, with various components shown in phantom for clarity.

The inner cannula drive assembly 46 also includes an inner cannula nut 54 configured to couple the inner cannula fork 48 to an inner cannula sleeve 56. In the depicted embodiment, the inner cannula sleeve 56, but not the inner cannula nut 54, has threads on an inner surface thereof, as shown in FIG. 17. In an alternative embodiment, the inner cannula nut 54, in addition to or instead of the inner cannula sleeve 56, can have internal threads. The inner cannula nut 54 and the inner cannula sleeve 56 are configured to ride on a lead screw 82 (described below). The inner cannula drive assembly 46 further includes an inner cannula dowel 58 configured to releasably and operatively couple to a cam to control movement of the inner cannula drive assembly 46 and the inner cannula 24, as described below.

Figure 12:
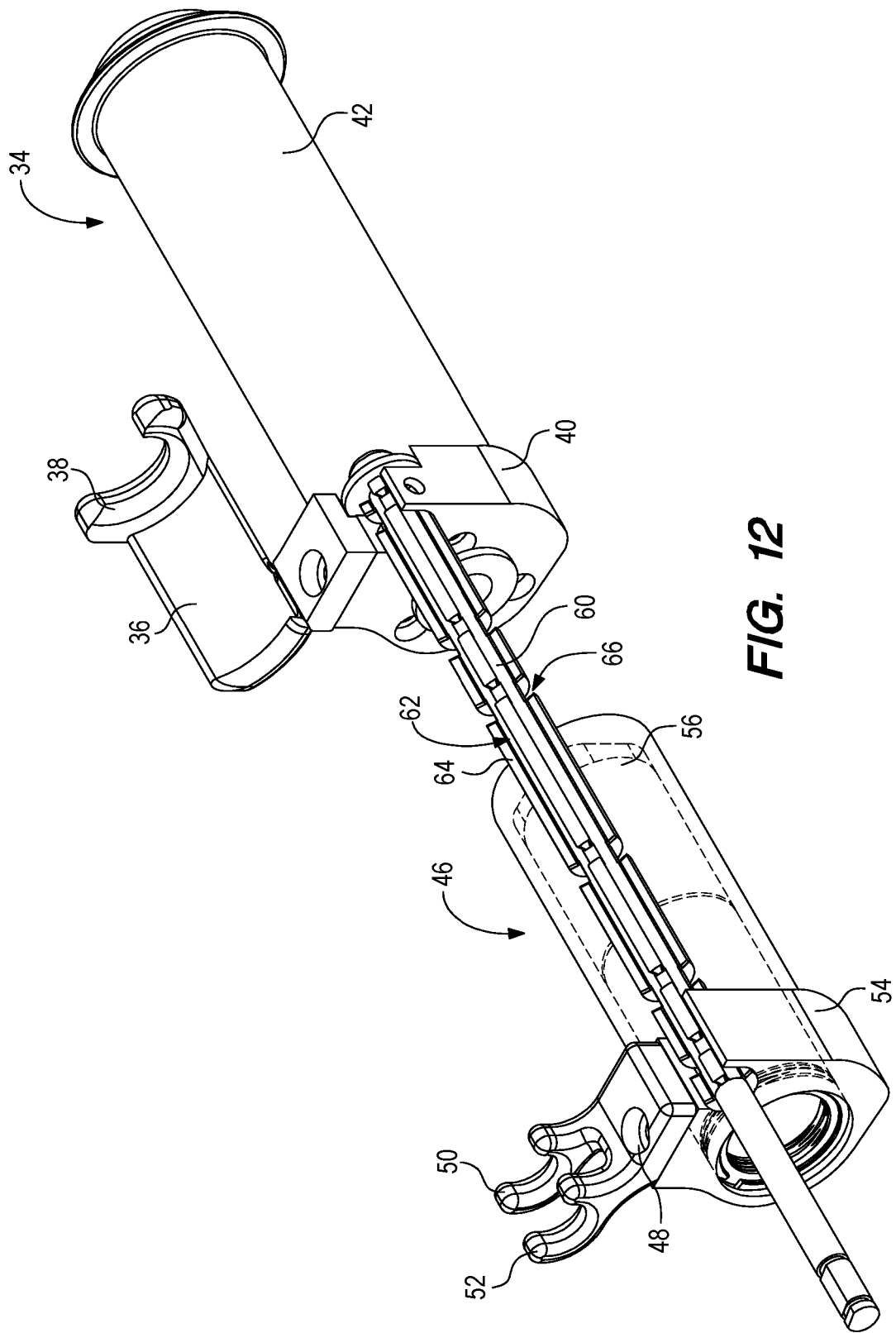
FIGS. 12 and 13 are two perspective views of the outer and inner cannula assemblies and the grooved cam of the two-part biopsy device depicted in FIGS. 1 to 7, with various components shown in phantom for clarity.
Figure 13:
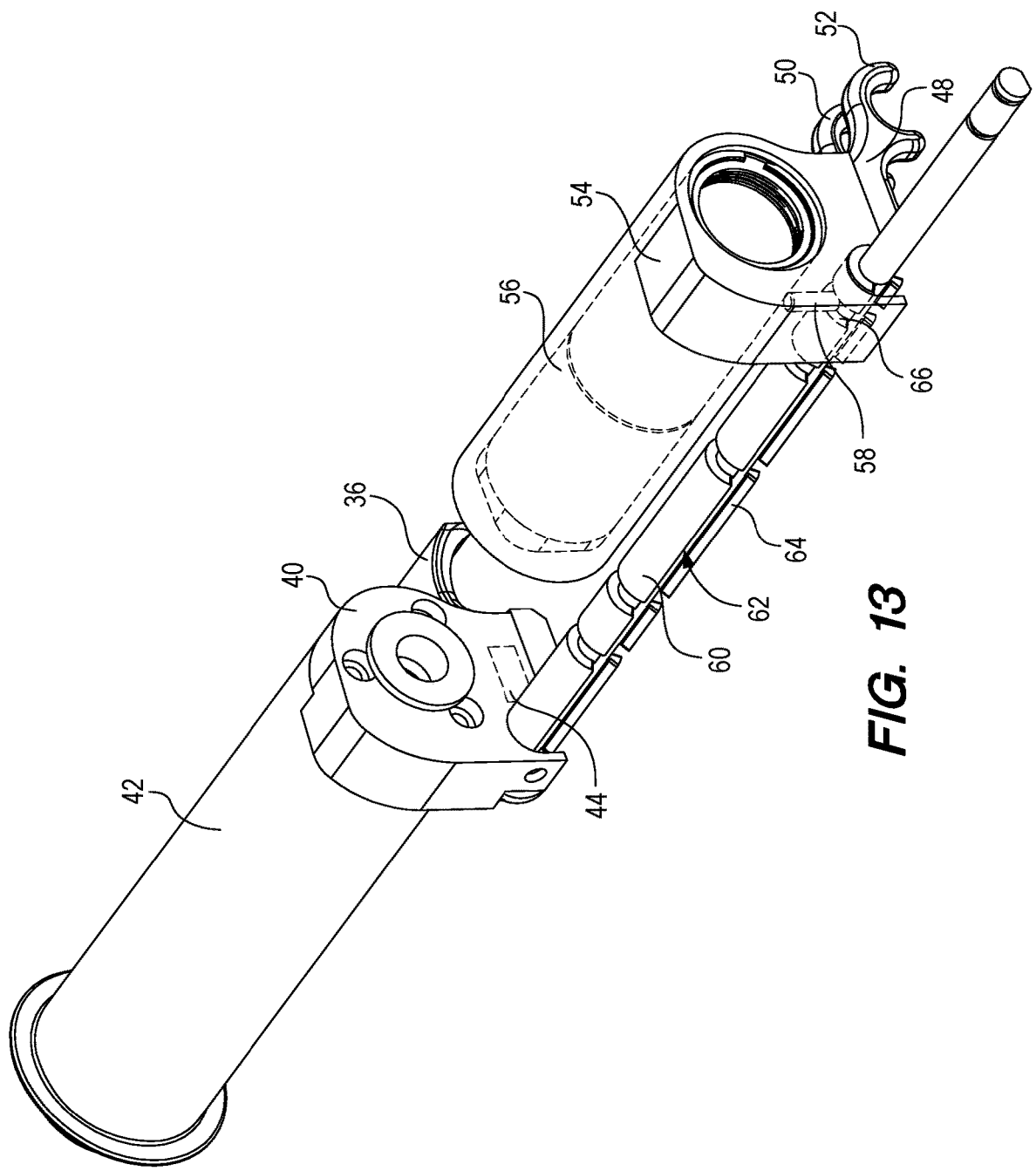

FIGS. 12 and 13 depicts an elongate grooved cam 60 disposed between the outer and inner cannula drive assemblies 34, 46. The cam 60 is configured to releasably and operatively couple to the outer cannula dowel 44 and the inner cannula dowel 58 to control axial movement of the outer and inner cannula drive assemblies 34, 46 and the outer and inner cannulas 18, 24. The cam 60 sits in recesses in the outer cannula nut 40 and the inner cannula nut 54, allowing it to interact with the outer and inner cannula dowels 44, 58. The cam 60 has longitudinal grooves 62 running along a substantial portion of its length. The longitudinal grooves 62 are defined by longitudinal raised portions 64 that also run along a substantial portion of the length of the cam 60. The longitudinal raised portions 64 are interrupted along the length of the cam 60, thereby defining a plurality of circumferential slots 66. The outer and inner cannula dowels 44, 58 can move axially along the longitudinal grooves 62, as long as the outer and inner cannula dowels 44, 58 are each in a longitudinal groove 62 (not shown). When the outer and inner cannula dowels 44, 58 are in a longitudinal groove 62, the outer and inner cannula drive assemblies 34, 46 are respectively "unlocked." When the outer and inner cannula dowels 44, 58 are in a circumferential slot 66, but not in a longitudinal groove 62, (as shown in FIG. 13), outer and inner cannula drive assemblies 34, 46 cannot move axially. When the outer and inner cannula dowels 44, 58 are in a circumferential slot 66, but not in longitudinal groove 62, the outer and inner cannula drive assemblies 34, 46 are respectively "locked."

If either the outer or inner cannula dowel 44, 58 is positioned in one of the circumferential slots 66 (best seen in FIG. 13), axial movement of that dowel 44, 58 relative to the cam 60 is prevented by the raised portions 64 adjacent the slots 66. Consequently, the assembly 34, 46 attached to that dowel 44, 58 is prevented from moving axially relative to the cam 60. When both the outer and inner cannula dowels 44, 58 are positioned in respect of circumferential slots 66, axial movement of those dowels 44, 58, and the respective assemblies 34, 46, relative to the cam 60 and to each other is prevented.

Figure 32:
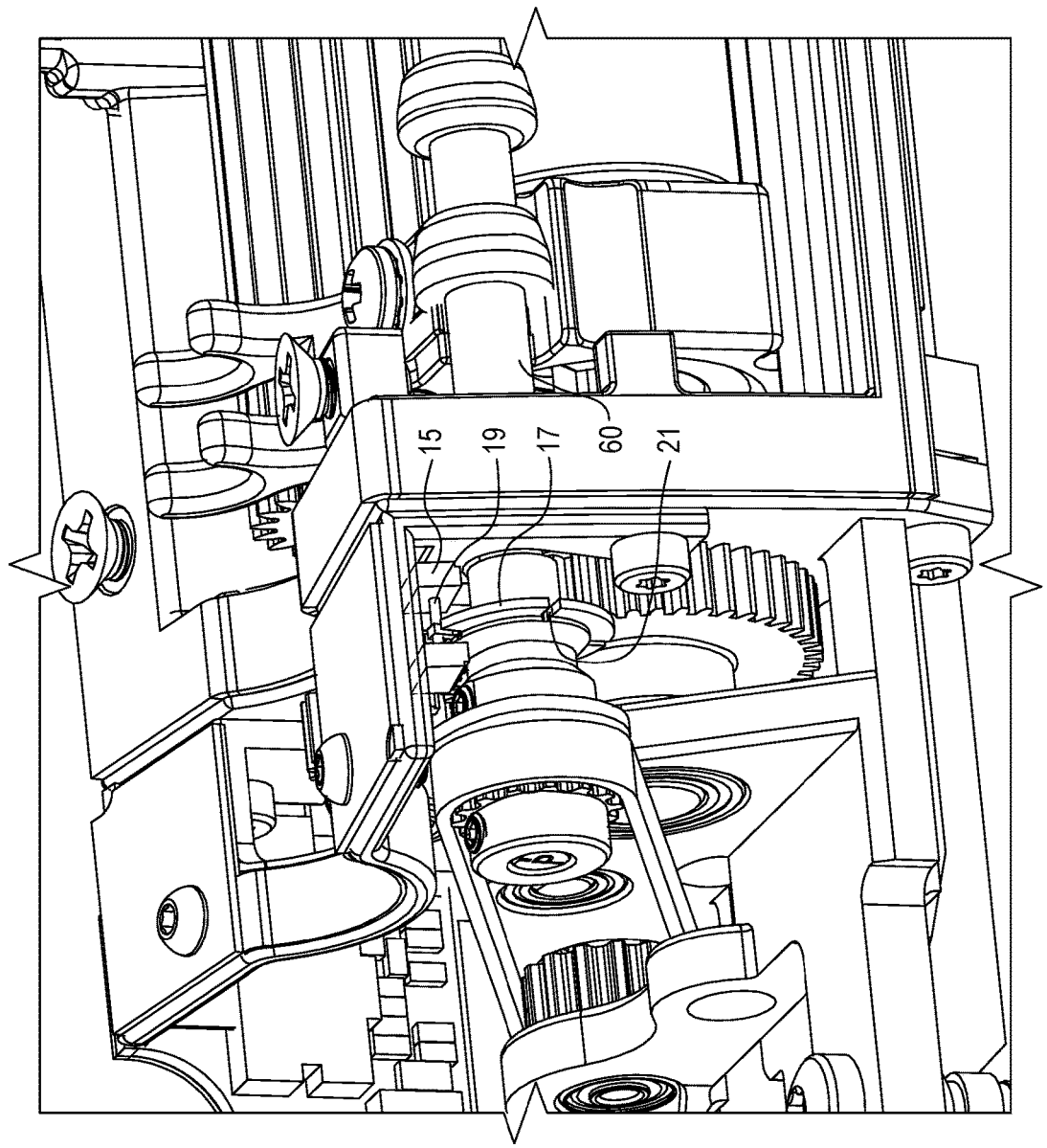
FIG. 32 is a detailed side perspective view of the biopsy device depicted in FIGS. 1 to 7, with various components omitted for clarity.
Figure 33:
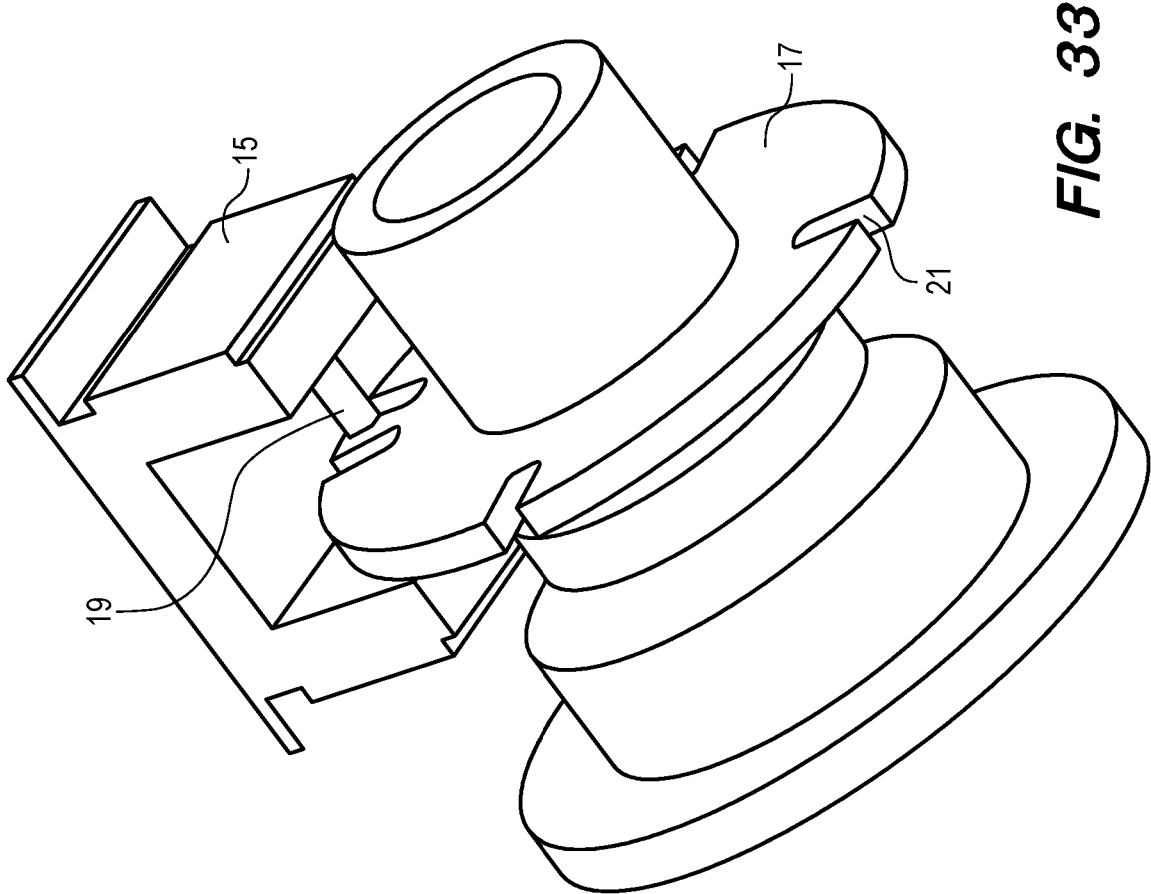
FIG. 33 is a detailed bottom perspective view of a sensor and an encoding disc of the biopsy device depicted in FIGS. 1 to 7.

In this embodiment, the biopsy device 10 also includes a small motor for rotating the cam 60 about its longitudinal axis. In other embodiments, the cam 60 can be rotated with a solenoid, a manual selector or a latch. As shown in FIGS. 32 and 33, the biopsy device 10 also includes a sensor 15 and an encoding disc 17 configured to determine the rotational position of the cam 60. The sensor 15 emits an optical beam 19 (e.g., a laser beam) and detects the optical beam unless something is disposed between the emitter and detector on the sensor. The encoding disc 17 is fixed to the cam 60 such that the disc 17 rotates when the cam 60 does. When the biopsy device 10 is assembled, the disc 17 is disposed partially in the sensor 15 such that in certain rotational positions, the disc 17 breaks the optical beam 19. Further, the encoding disc 15 defines windows 21 through which the optical beam 19 can pass. The sensor 15 sends a signal to the controller to indicate whether it detects the optical beam 19. Accordingly, the controller can interpret the signal from the sensor 15 to at least partially determine the rotational position of the cam 60 to which the disc 15 is fixed. While the depicted encoding disc 17 is associated with only one sensor 15, in other embodiments, the encoding disc 17 is associated with more than one sensor to enable encoding of more than two states. Given "n" sensors, the number of states that can be identified is 2n. Similar sensors 15 can also be used to determine other biopsy variables, such as aperture size.

Figure 14:
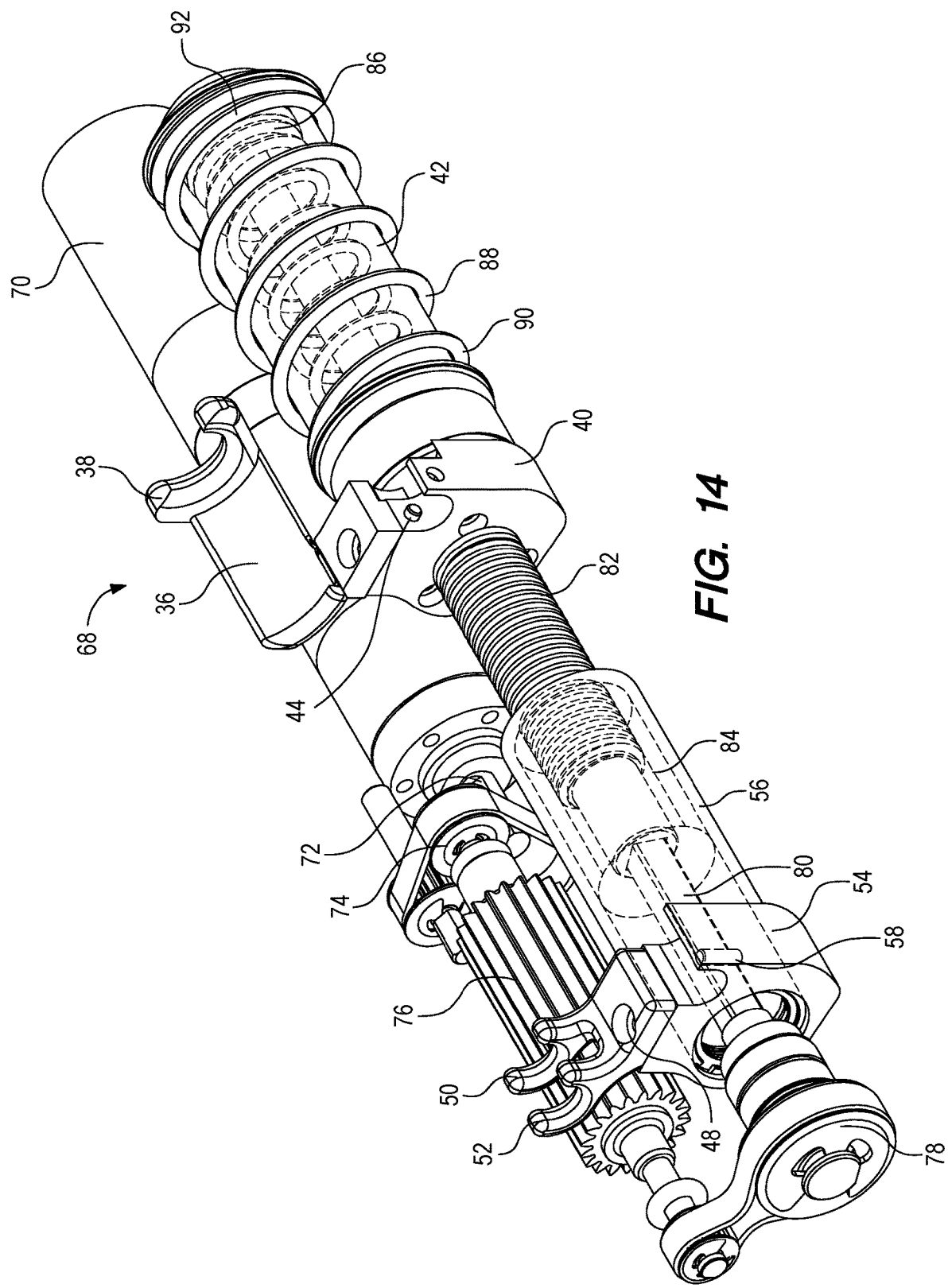
FIG. 14 is a perspective view of the drive system of the two-part biopsy device depicted in FIGS. 1 to 7, with various components shown in phantom for clarity.

The reusable portion 32 also includes a drive assembly 68, depicted in FIG. 14, configured to cause movement of the outer and inner cannulas 18, 24. The drive assembly 68 is powered by a single motor 70 having a reversible output shaft (motor axle) 72, which can be any type of reversible-output rotary motor known in the art (e.g., electric, pneumatic, hydraulic). The motor 70 is different from the small motor for rotating the cam 60. The motor 70 rotates the motor axle 72, which in turn rotates the drive belt of a motor pulley-drive belt assembly 74. The motor pulley-drive belt assembly 74 rotates a spline 76, which is essentially an elongate pinion. The spline 76 is configured to operatively couple to the inner cannula gear 30 to rotate the inner cannula 24 through a wide range of axial positions of the inner cannula gear 32 relative to the spline 76.

Figure 34:
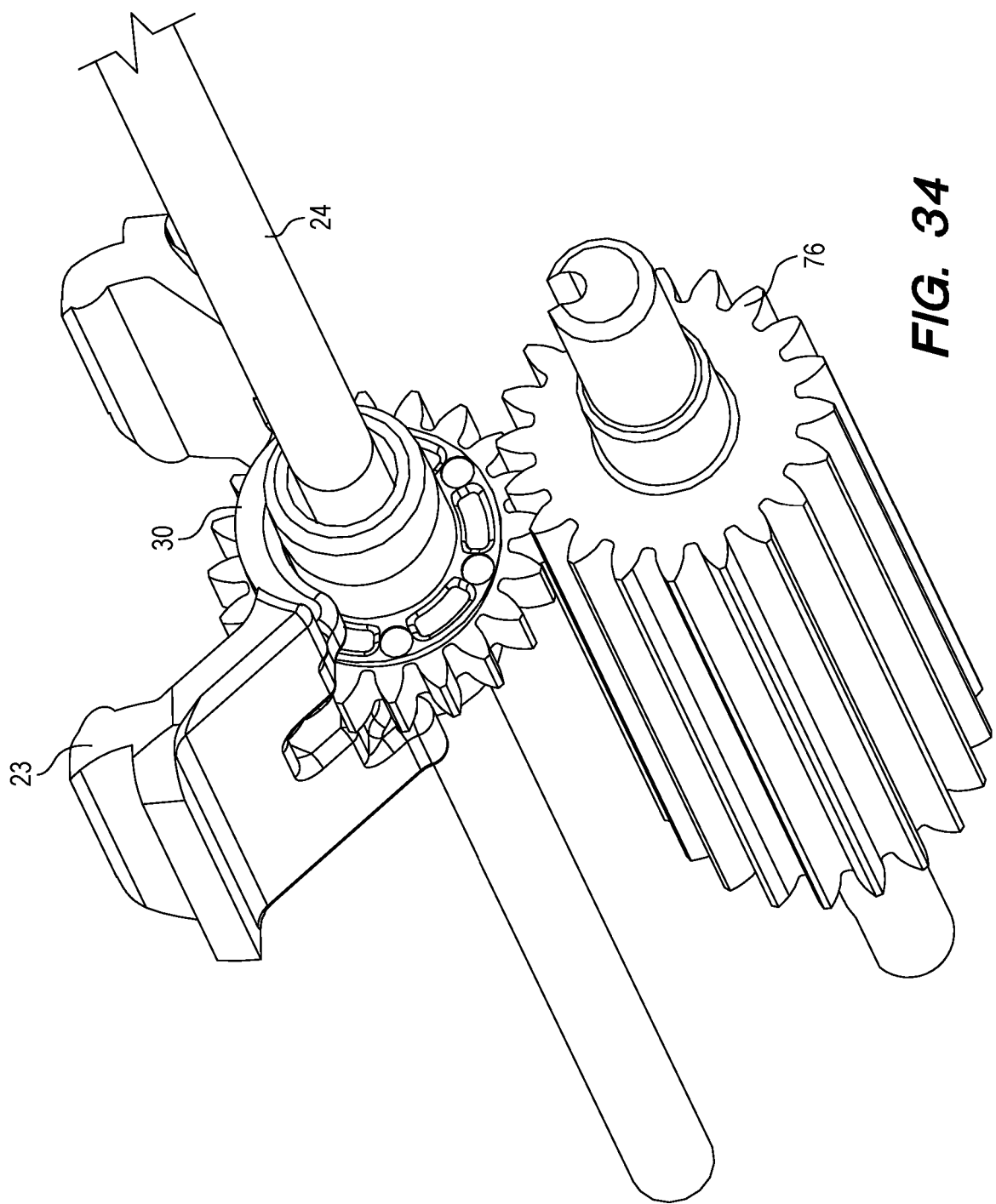
FIGS. 34 and 35 are detailed perspective and side views of an inner cannula and a spline of the biopsy device depicted in FIGS. 1 to 7, including the inner cannula gear and the sliding support member.
Figure 35:
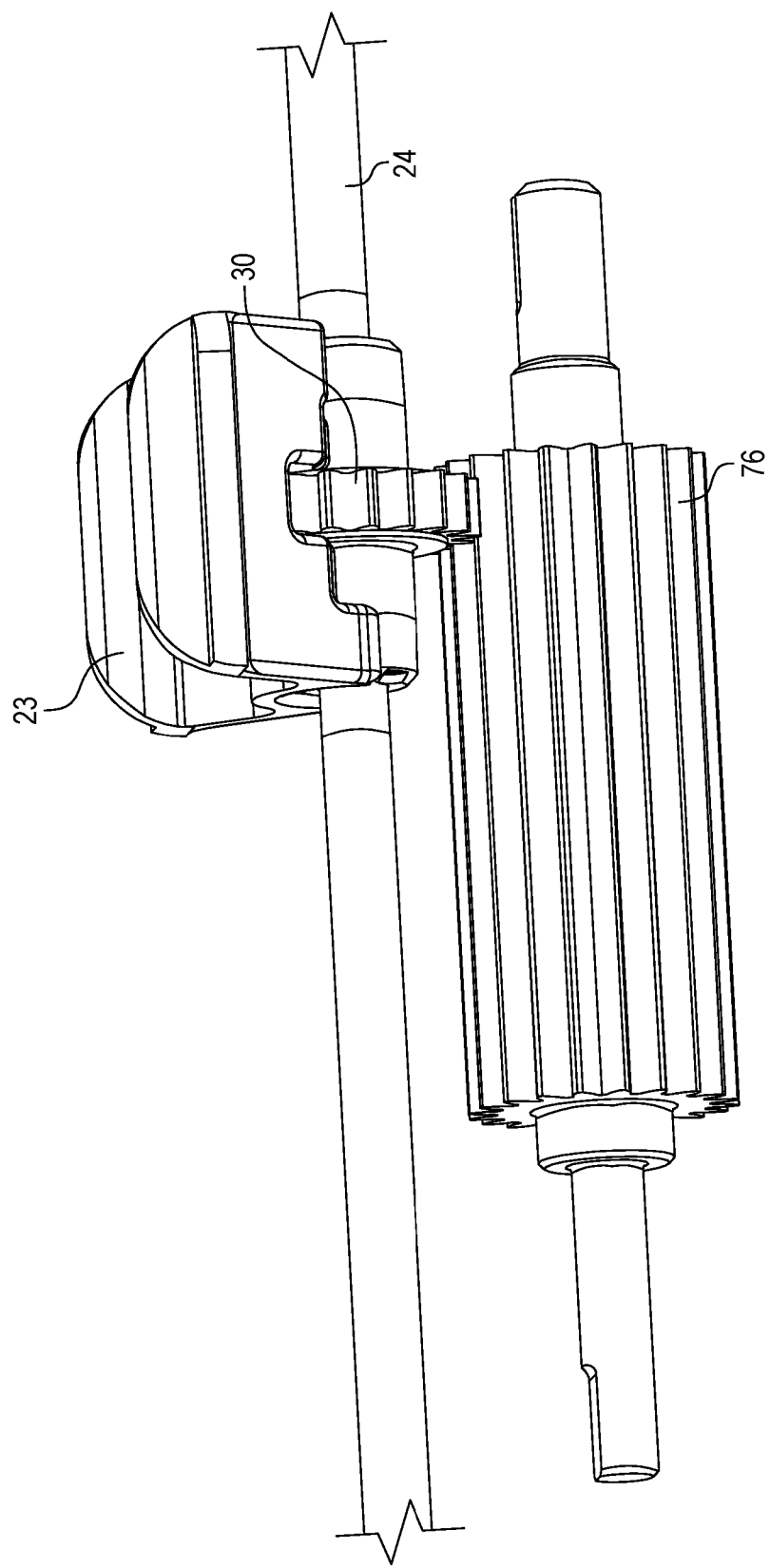

In order to maintain contact between the inner cannula gear 30 and the spline 76, the disposable portion 16 includes a sliding support member 23, as shown in FIGS. 34 and 35. The sliding support member 23 is fixed to the inner cannula 24 on either side of the inner cannula gear 30 and translates axially therewith. The sliding support member 23 is also biased to force the inner cannula 24 and the inner cannula gear 30 downward toward the spline 76 in the reusable portion 32 when the disposable and reusable portions 16, 32 are mated. Accordingly, the sliding support member 23 maintains contact between the inner cannula gear 30 and the spline 76 to ensure rotation of the inner cannula 24 when the motor 70 rotates.

The distal end of the spline 76 is operatively coupled to the motor pulley-drive belt assembly 74, and the proximal end of the spline 76 is operatively coupled to the spline pulley-drive belt assembly 78. Therefore, when the spline 76 rotates, it rotates the drive belt of the spline pulley-drive belt assembly 78. The spline pulley-drive belt assembly 78 is operatively coupled to the lead screw adapter 80, therefore, when the drive belt of the spline pulley-drive belt assembly 78 rotates, it rotates the lead screw adapter 80. While the depicted drive assembly 68 includes pulley-drive belt assemblies 74, 78, in other embodiments the drive belts are replaced by gears.

Figure 15:
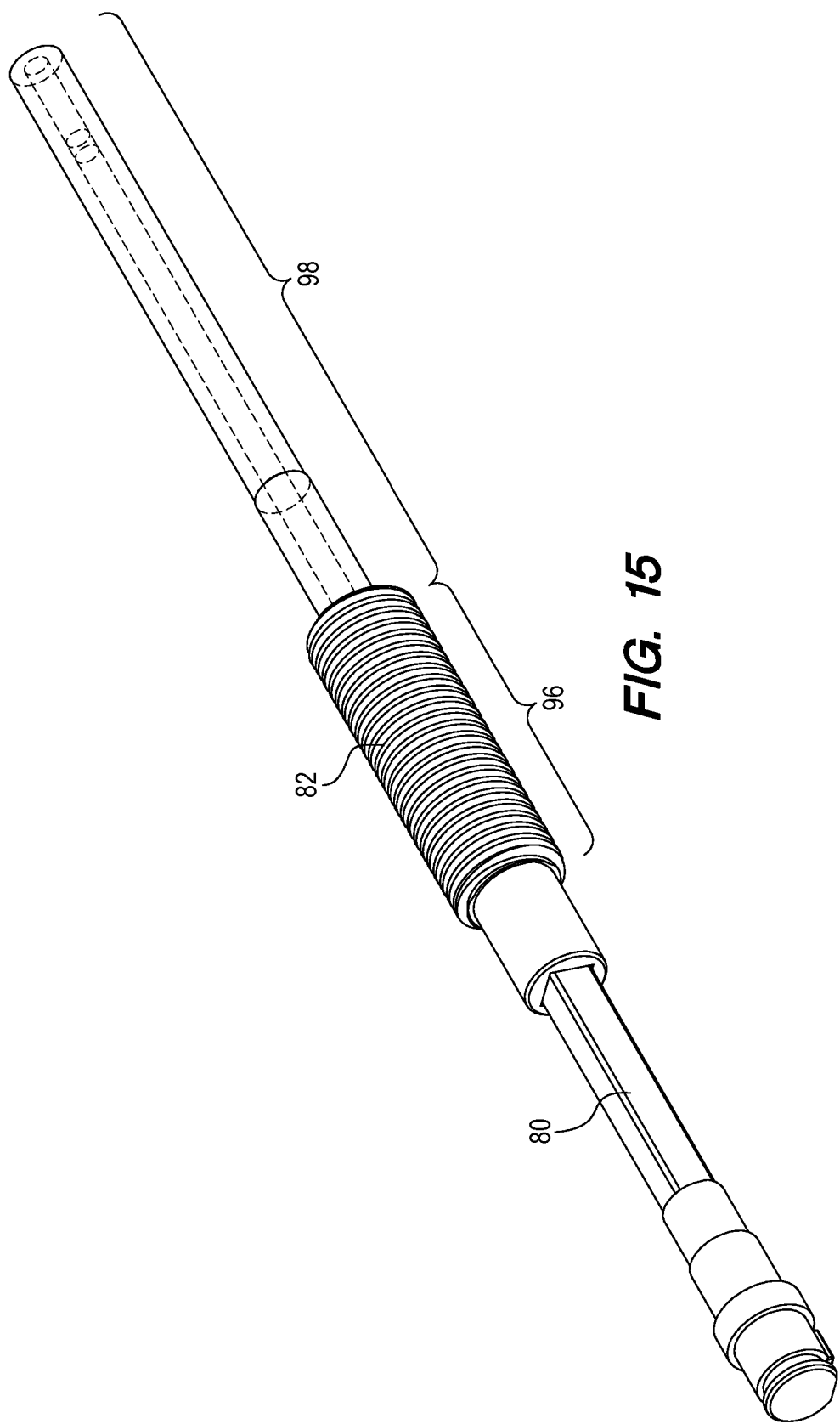
FIG. 15 is a perspective view of the lead screw and lead screw adapter of the two-part biopsy device depicted in FIGS. 1 to 7.

As shown in FIG. 15, the lead screw adapter 80 has a square cross-section, and the lead screw 82 has a lumen with a square cross-section that corresponds to the cross-section of the lead screw adapter 80. While the lead screw adapter 80 in the depicted embodiment has a square cross-section, the cross-section can have any shape that would transfer rotational motion (i.e., triangular, oval, and hexagonal). Alternatively, the lead screw adapter 80 and the lead screw 82 can include a "pin and slot" pair. A distal end of the lead screw adapter 80 is inserted into the lumen of the lead screw 82. Accordingly, the lead screw 82 "floats" (i.e., is not axially restrained) on the lead screw adapter 80, while it is operatively coupled to the lead screw adapter 80 with respect to rotation. In other words, the lead screw 82 is free to move axially relative to the lead screw adapter 80, but when the lead screw adapter 80 is rotated, the lead screw 82 also rotates. The lead screw 82 has threads on an outer surface thereof. In other embodiments, motor 70 can be disposed outside of the biopsy device 10 (including the reusable portion 32 thereof), and operatively connected to the spline 76 and lead screw 82 via a drive cable or drive shaft between the motor 70 and the biopsy device 10. The lead screw adapter 80 may be generally referred to as a drive shaft.

Figure 16:
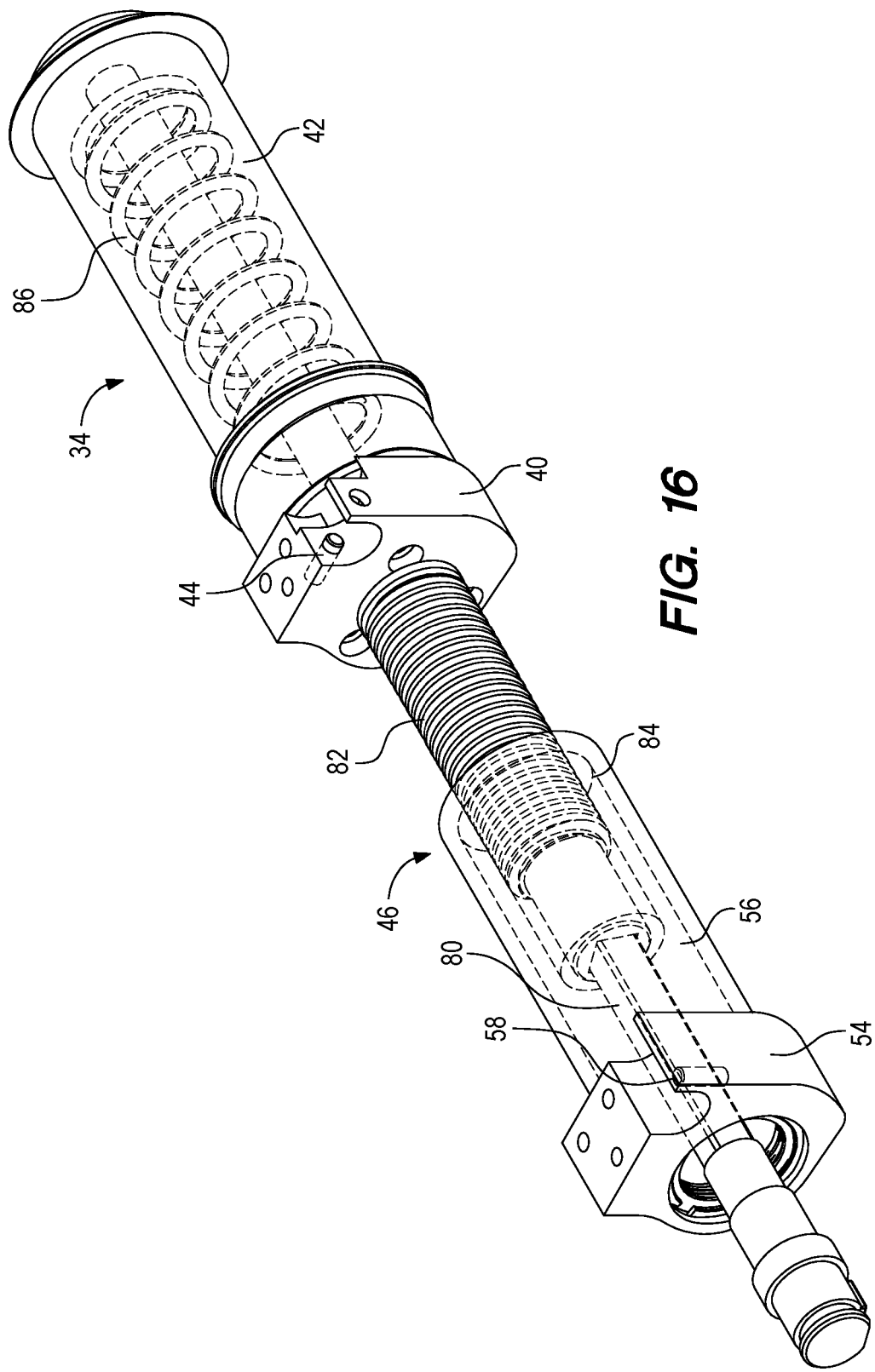
FIG. 16 is a perspective view of the outer and inner cannula drive assemblies, the lead screw and the lead screw adapter of the two-part biopsy device depicted in FIGS. 1 to 7, with various components shown in phantom for clarity.
Figure 18:
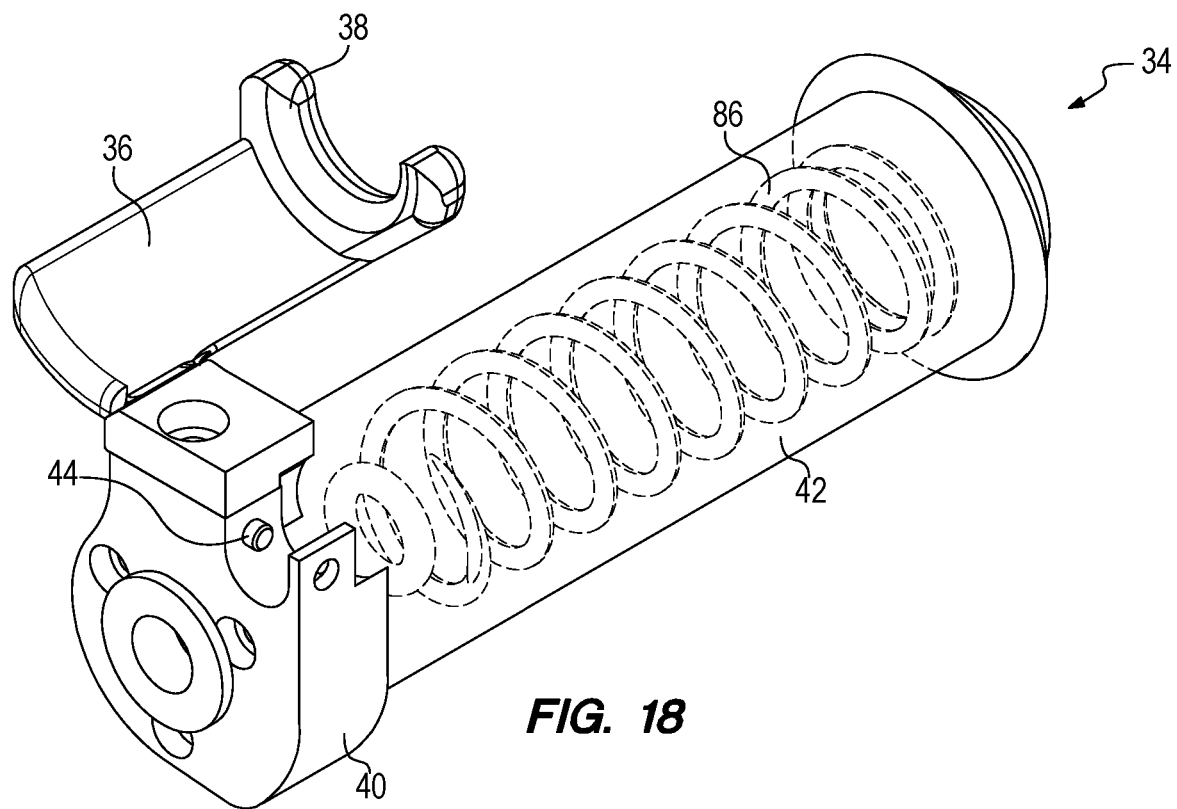
FIG. 18 is a perspective view of the outer cannula drive assembly of the two-part biopsy device depicted in FIGS. 1 to 7, with various components shown in phantom for clarity.

FIGS. 16 to 18 depict the physical and operational coupling between the lead screw adapter 80, lead screw 82, and the outer and inner cannula drive assemblies 34, 46. FIG. 16 depicts portions of the outer and inner cannula drive assemblies 34, 46 operatively coupled to the lead screw 82 the lead screw adapter 80. Other portions have been omitted and still other portions are shown in phantom for clarity. The threads on the inner surface of the inner cannula sleeve 56 mate with the threads on the outer surface of the lead screw 82. Accordingly, when axial movement of the outer cannula drive assembly 34 is restricted and the lead screw 82 is rotated, the inner cannula drive assembly 46, and therefore the inner cannula 24, is moved in an axial direction by the rotation of the lead screw 82. Further, the inner cannula drive assembly 46 and the inner cannula 24 can be reciprocated in an axial direction by reversing the direction of rotation of the motor 70 and the lead screw 82 while restricting axial movement of the outer cannula drive assembly 34. In an alternative embodiment, the inner cannula sleeve 56 is circumferentially disposed around a lead screw nut 84, and rotational and axial movement of the lead screw nut 84 is restricted in the inner cannula sleeve 56.

The lead screw 82 is temporarily axially fixed to the outer cannula drive assembly 34 by expansive force of a dwell spring 86 (described in detail below). Accordingly, when axial movement of the inner cannula drive assembly 46 is restricted, and lead screw 82 is rotated, the outer cannula drive assembly 34, and therefore the outer cannula 18, is moved in an axial direction by the rotation of the lead screw 82. As discussed above, axial movement of the inner cannula drive assembly 46 can be restricted by placing the inner cannula dowel 58 in a circumferential slot 66 of the grooved cam 60. Similarly, axial movement of the outer cannula drive assembly 34 and the lead screw 82 attached thereto can be restricted by placing the outer cannula dowel 44 in a circumferential slot 66 of the grooved cam 60.

As shown in FIGS. 25, 29 and 30, the lead screw 82 has a threaded proximal portion 96 and a non-threaded distal portion 98. The distal end of the distal portion 98 of the lead screw 82 is fixed to a thrust bearing 95. The thrust bearing 95 includes a cage with spherical bearings sandwiched between two washers. The distal-most washer is fixed to the lead screw 82 and rotates with the lead screw 82. The remainder of the thrust bearing 95 is free floating and the proximal washer does not rotate during operation of the biopsy device 10. A dwell spring 86 is disposed in a lumen of the outer cannula sleeve 42 between a proximal wall of the outer cannula sleeve 42 at the proximal end and the thrust bearing 95 at the distal end. The lead screw 82 passes through the lumen of the dwell spring 86, is not in contact therewith.

The lead screw 82 is not axially fixed with respect to the lead screw adapter 80, thereby allowing the lead screw 82 to translate axially relative to the lead screw adapter 80. The lead screw adapter 80 is rotationally fixed to the proximal portion 96 of the lead screw 80 by the square cross section of the distal portion of the lead screw adapter 82 and the square lumen in the proximal portion 96 or the lead screw 80. FIG. 25 shows the distal portion 98 of the lead screw 82 passes through a lumen in the outer cannula nut 40. The lead screw 82 can rotate freely about its axis and translate axially relative to the outer cannula nut 40.

In FIG. 29, the dwell spring 86 is preloaded with approximately 12 pounds of force and the lead screw 82 is temporarily axially fixed to the outer cannula drive assembly 34 in an "axial translation mode." The dwell spring 86 is biased to expand and will do so unless it is restrained by the lead screw 82, the thrust bearing 95 attached thereto and a proximal end of the outer cannula sleeve 42. In the axial translation mode, the dwell spring 86 applies a force on the lead screw 82 sufficient to hold the shoulder 91 of the distal portion 98 of the lead screw 82 in contact with the proximal surface of the bearing 93, which is fixed to the outer cannula nut 40. The applied force is less than the approximately 12 pounds of preload because the applied force is equal to the preload minus the force translating the outer and inner cannula drive assemblies 34, 46. Further, the bearing 93 is made of a low friction material (e.g., Teflon) to reduce the friction between the bearing 93 and the shoulder 91 of the lead screw 82. The outer cannula nut 40 and the outer cannula sleeve 42 are fixed to each other and form a portion of the outer cannula drive assembly 34. Accordingly, when the dwell spring 86 is preloaded as shown in FIG. 29, lead screw 82 is temporarily axially fixed to the outer cannula drive assembly 34 in the axial translation mode. As described above, with the lead screw 82, the outer cannula drive assembly 34 and the dwell spring 86 in the axial translation mode, rotation of the lead screw 82 causes axial movement of either the outer or inner cannula drive assemblies 34, 46.

In FIG. 30, the lead screw 82, the outer cannula drive assembly 34 and the dwell spring 86 are in a "dwell mode." In the dwell mode, the dwell spring 86 is compressed by proximal movement of the lead screw 82 and the thrust bearing 95 attached thereto relative to the outer cannula sleeve 42. The lead screw 82 and the thrust bearing 95 are moved proximally by rotation of the lead screw 82 because the outer cannula drive assembly 34 is temporarily axially locked as described above and the inner cannula 24 (and the inner cannula drive assembly 46 attached thereto) is prevented from moving distally by a "hard stop" (i.e., a shoulder) in the disposable portion 16. The hard stop absorbs the force applied to the inner cannula 24 during dwell and prevents the cutting-edge at the distal end of the inner cannula 24 from being dulled by the cutting board 11. Because the inner cannula drive assembly 46 cannot move axially in a distal direction with respect to the outer cannula drive assembly 34, continued rotation of the lead screw 82 generates an axial force that overcome the expansive force of the dwell spring 86. The lead screw 82 moves proximally away from the outer cannula sleeve 42 and the shoulder 91 of the distal portion 98 of the lead screw 82 moves away from the proximal surface of the bearing 93. The lead screw 82 and the dwell spring 86 allow the motor 70 to maintain an appropriate amount of axial cutting force to the inner cannula 24 without further advancing the inner cannula 24. Because the dwell spring 86 is preloaded with approximately 12 pounds of force and because the outer and inner cannula drive assemblies 34, 46 cannot move relative to each other in "dwell mode," the axial cutting force applied to the inner cannula 24 is approximately 12 pounds.

As shown in FIG. 26a, before the inner cannula drive assembly 46 reaches its distal-most position, the expansive force imposed on the lead screw 82 by the dwell spring 86 is sufficient to hold the shoulder 91 of the distal portion 98 of the lead screw 80 in contact with the proximal surface of the bearing 93 in outer cannula nut 40. After the inner cannula drive assembly 46 reaches its distal-most position (FIG. 26b and FIG. 29), continued rotation of the lead screw adapter 80 cannot move the inner cannula drive assembly 46 more distally. Consequently, rotational force applied to the lead screw 82 produces an axial force that overcomes the expansive force of the dwell spring 86 and moves the shoulder 91 of the lead screw 82 away from the proximal surface of the bearing 93 in outer cannula nut 40 (FIG. 26c and FIG. 30). The difference between FIGS. 26a and 26b is that the inner cannula drive assembly 46 has not reached its distal-most position in FIG. 26a, whereas it has reached its distal-most position in FIG. 26b. The difference between FIGS. 26b and 26c is that the shoulder 91 of the distal portion 98 of the lead screw 80 remains in contact with the proximal surface of the bearing 93 in the outer cannula nut 40 due to the expansive force of the dwell spring 86 in FIG. 26b. In FIG. 26c, rotation of the lead screw adapter 80 has overcome the expansive force of the dwell spring 86 and driven the shoulder 91 away from the bearing 93.

In turn, movement of the shoulder 91 away from the bearing 93 allows the lead screw 82 to continue rotating without changing the axial positions of the outer and inner cannula drive assemblies 34, 46, which have both reached their distal-most positions. Continued rotation of the lead screw 82 allows the motor 70 to continue rotating the spline 76, which results in continued rotation of the inner cannula 24. As the lead screw 82 continues to rotate after the inner cannula drive assembly 46 has reached its distal-most position, the shoulder 91 of the lead screw 80 moves away from the proximal surface of the bearing 93 in outer cannula nut 40. When the lead screw 82 (by reversing motor 70) is rotated in an opposite direction the lead screw 82 moves distally and the dwell spring 86 relaxes and elongates. In an alternative embodiment, the biopsy device 10 can include a tension spring to pull the lead screw 82 in the distal direction. The lead screw 82 continues to rotate after the inner cannula drive assembly 46 has reached its distal-most position for a period of time called the "dwell period." In one embodiment, the dwell period is 0.9 seconds. The dwell period can be adjusted by modifying the pitch and rotation rate of the lead screw 82. In one embodiment, the pitch of the lead screw 82 is 20 threads per inch. The dwell portion of the cutting cycle can be adjusted to provide a desired dwell time. The distance the lead screw 82 moves during the dwell period is a function of the lead screw 82 pitch and rotation speed.

The lead screw 82 pitch (and belt/pulley ratios of the motor and spline pulley-drive belt assemblies 74, 78) can also be adjusted to provide the desired relationship between the inner cannula 24 rotation speed and advancement speed. In one embodiment, the inner cannula 24 rotates at about 2,500 RPM and advances at about 23.01 mm/s (taking approximately 1.09 seconds to advance to the cutting board 11). In that embodiment, the lead screw 82 pitch is about 0.050" (20 turns per inch) to allow the desired rotation and advancement rates to be achieved while keeping the motor speed and current within limits that would allow continuous cycling. The motor 70 can be changed while maintaining the desired rotation and advancement rates by modifying the pitch of the lead screw 82. While this embodiments is described with reference to specific pitch, rate of rotation (RPM), and rate of advancement (mm/s), biopsy devices according to various embodiments can have a variety of pitches, rates of rotation and rates of advancement. For instance, the rate of rotation is 1,800 RPM and the rate of advancement is 16.7 mm/s in another embodiment.

At the end of the dwell period, the lead screw adapter 80 is rotated in the opposite direction (by reversing motor 70), thereby allowing the dwell spring 86 to expand. The lead screw 82 moves toward the proximal surface of the outer cannula nut until the shoulder 91 of the lead screw 82 contacts the bearing 93 in outer cannula nut 40. At that point, the shoulder 91 of the lead screw 80 remains in contact with the bearing 93 in outer cannula nut 40 as the lead screw 82 continues to rotate and the inner cannula drive assembly 46 is driven in a proximal direction. The lead screw adapter 80 is able to rotationally drive the lead screw 82 and its various parts during this process because the lead screw adapter 80 is axially movable within the proximal portion 96 of the lead screw 82.

While the dwell spring 86 depicted in this application is a coil spring, the dwell spring 86 may be any type and shape of suitable spring, such as leaf springs, linear springs, and oval springs. While the biopsy device 10 described herein achieves a dwell period using a dwell spring 86, other biopsy devices may achieve a dwell period using a clutch system.

FIGS. 23 to 25, 26a to 26c, 29 and 30 depict the biopsy device 10 in side view (FIG. 23) and side cross-sectional view (FIGS. 24, 25, 26a to 26c, 29 and 30). These figures depict the interaction of the lead screw adapter 80, the lead screw 82, including the proximal and distal portions thereof 96, 98, and the dwell spring 86. The dwell spring 86 allows the lead screw 82 to rotate without axially moving either the inner cannula drive assembly 46 or the outer cannula drive assembly 34.

The dwell spring 86 maintains a minimum cutting force while allowing biopsy device 10 to operate as described above. In one embodiment, the dwell spring 86 is configured to have approximately 12 pounds of preload, to ensure that the biopsy device 10 can apply approximately 12 pounds of cutting force in a distal axial direction during dwell.

In an alternative embodiment, the lead screw nut 84 can be configured to be axially moveable and rotationally fixed within the inner cannula sleeve 56. The dwell spring 86 is then positioned within the inner cannula sleeve 56 with the distal end of the dwell spring 86 coupled to the inner cannula sleeve 54 and the proximal end coupled to the lead screw nut 84 to apply force in the proximal direction. The lead screw would be axially fixed and rotationally movable in the outer cannula nut 40. In this alternate embodiment, when the inner cannula drive assembly 46 and the outer cannula drive assembly 34 are in their respective distal-most positions, continued rotation of the lead screw 82 would move the lead screw nut 84 in the distal direction compressing the dwell spring 86. When the lead screw 82 is rotated in an opposite direction (by reversing motor 70) the lead screw nut 84 moves proximally and the dwell spring 86 relaxes and elongates.

A firing spring 88 is disposed around an outer surface of the outer cannula sleeve 42 as shown in FIGS. 9 and 14, which is compressed during arming to power firing of the outer and inner cannulas 18, 24 (described below). In an alternative embodiment, the biopsy device 10 includes a tension spring to pull the inner and outer cannulas 24, 18 forward during firing. A proximal end 90 of the firing spring 88 is fixedly coupled to the frame 31. A distal end 92 of the firing spring 88 is fixedly coupled to outer cannula sleeve 42 at a position distal of the point where the proximal end 90 is attached to the frame 31 (see FIG. 1). Accordingly, when the outer cannula sleeve 42 moves proximally relative to the frame 31 and the housing 12 attached thereto, the firing spring 88 is compressed and stores potential energy for moving the outer cannula sleeve 42 in a distal direction. The biopsy device 10 also includes a PC board 94, which includes a microprocessor programmed to control rotation of the motor 70 and movement of the various components of the biopsy device 10.

Figure 19:
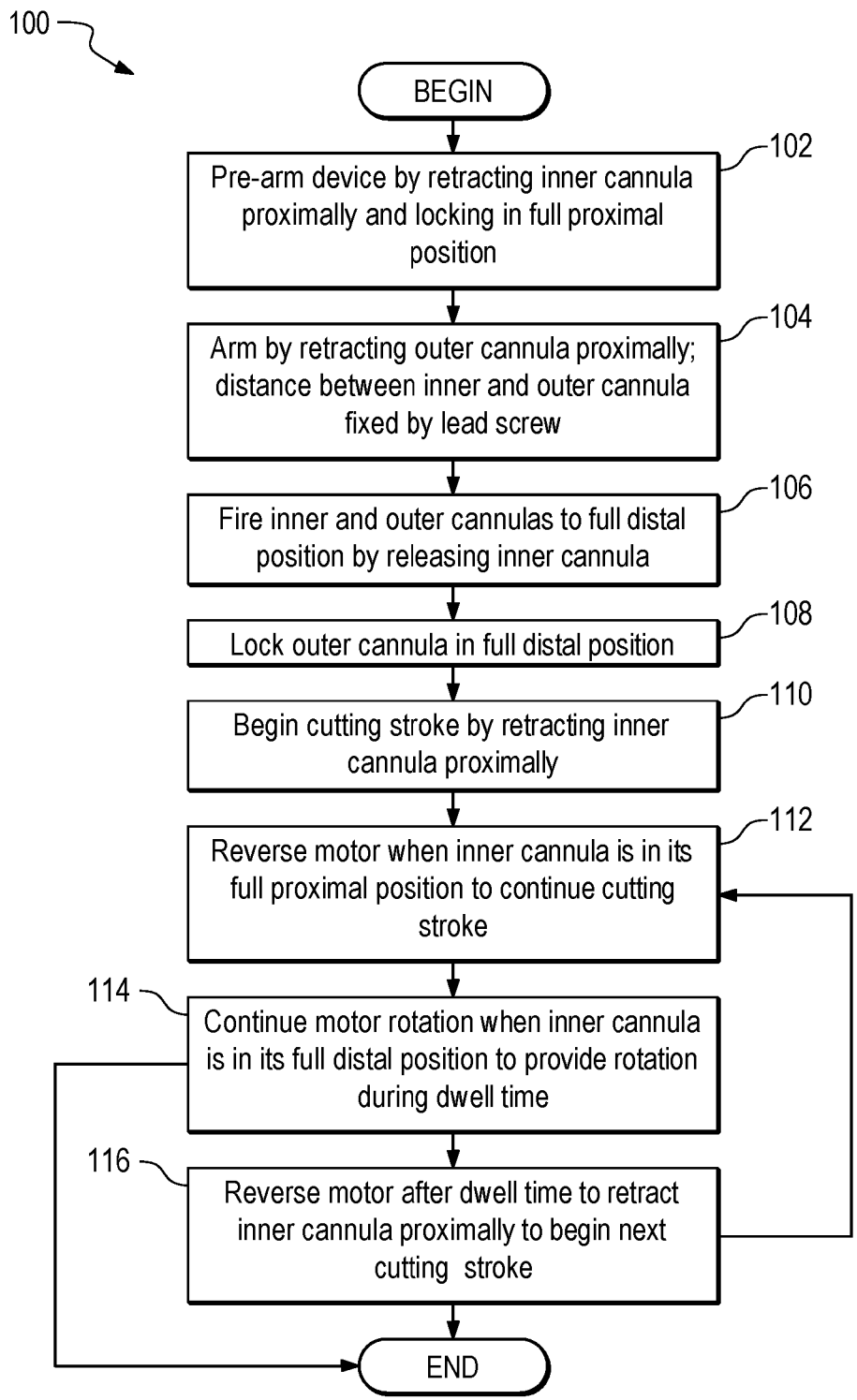
FIG. 19 is a flow-chart depicting a biopsy procedure, according to one embodiment.

Having described the structure of various components of the biopsy device 10, a biopsy procedure 100 using the biopsy device 10 will now be described. FIG. 19 depicts the steps of a biopsy procedure 100 according to one embodiment. The table in FIG. 20 summarizes the positions of various components of the biopsy device 10 during the biopsy procedure 100. FIGS. 21a to 21m depict the positions of the various components of the biopsy device 10 during the procedure 100. FIGS. 22a to 22m depict the rotational position of the grooved cam 60 and its interactions with the outer and inner cannula dowels 44, 58 to lock and unlock axial movement of the outer and inner cannulas 18, 24.

The disposable portion 16 of the biopsy device 10 is provided in its shipping or home position. For the first biopsy of the day, the reusable portion 32 of the biopsy device 10 is set to its shipping or home position by a computer controller prior to attaching to the disposable portion 16, as follows. The inner cannula drive assembly 46 is driven proximally (with the outer cannula drive assembly 34 locked in its standard distal position) until the inner cannula drive assembly 46 triggers a limit sensor, thereby resetting or "homing" the inner cannula drive assembly 46 at its proximal-most location. Next, the outer cannula drive assembly 34 is driven proximally (with the inner cannula drive assembly 46 locked in its proximal-most position) until the outer cannula drive assembly 34 abuts the inner cannula drive assembly 46 (detected by increased load on the motor 70), thereby resetting or "homing" the outer cannula drive assembly 34 at its proximal-most location. Then the outer and inner cannula drive assemblies 34, 46 are moved to their respective distal-most positions (determined by the amount of lead screw rotation). For subsequent biopsies during the remainder of the day (or the appropriate time period), the reusable portion 32 of the biopsy device 10 is set to its home position at the end of the previous biopsy. However, the biopsy device 10 may use the limit sensor to confirm the proximal-most locations of the outer and inner cannula drive assemblies 34, 46.

Figure 21A:
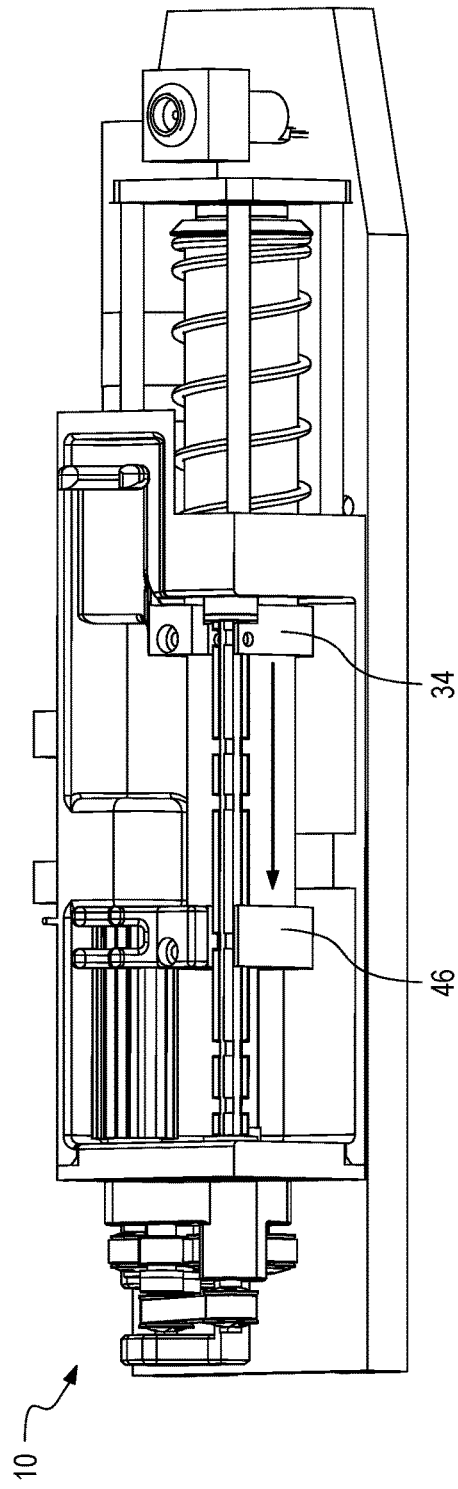
Figure 22A:
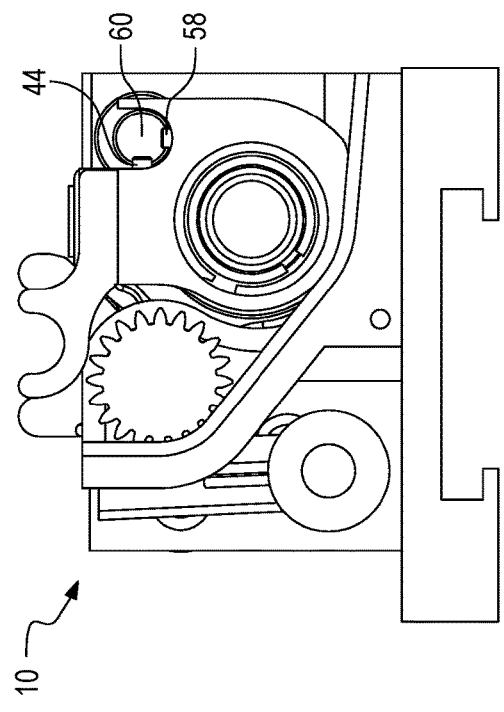
Figure 21B:
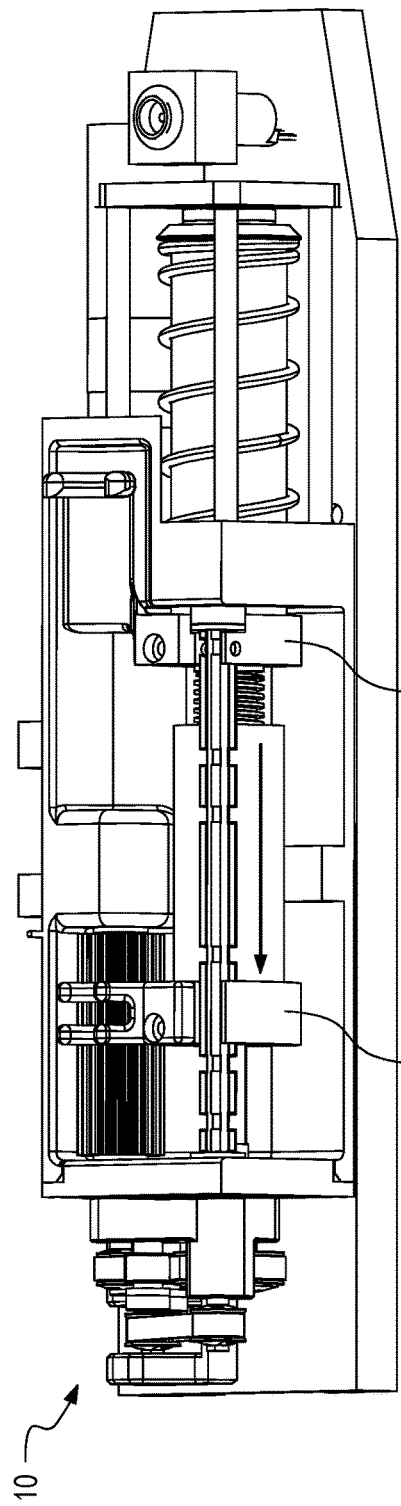

The disposable and reusable portions 16, 32 of the biopsy device 10 are attached to each other while they are in their respective shipping or home positions. In the respective shipping or home positions of the disposable and reusable portions 16, 32 the cam 60 is rotated such that both the outer and inner cannula drive assemblies 34, 46 are unlocked, and both the outer and inner cannulas 18, 24 are in their respective distal-most positions. This position is depicted in FIGS. 21a and 22a, and summarized in FIG. 20. An introducer (not shown) is attached to the biopsy device 10, and the biopsy device is mounted to a stabilized surface (not shown) using the base plate 14.

Figure 36:
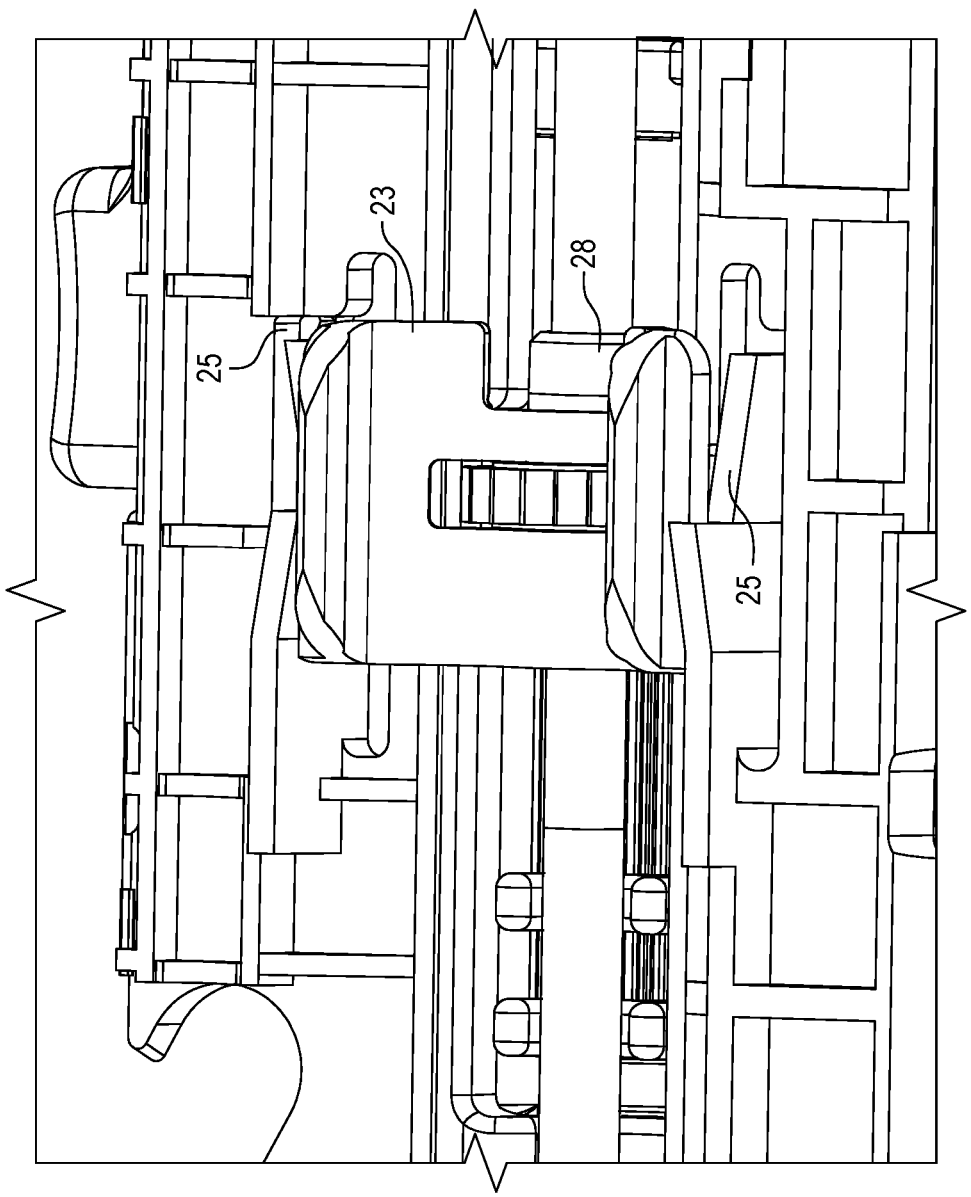
FIGS. 36 and 37 are detailed top perspective views of the disposable portion of the biopsy device depicted in FIGS. 1 to 7, with various components omitted for clarity.
Figure 37:
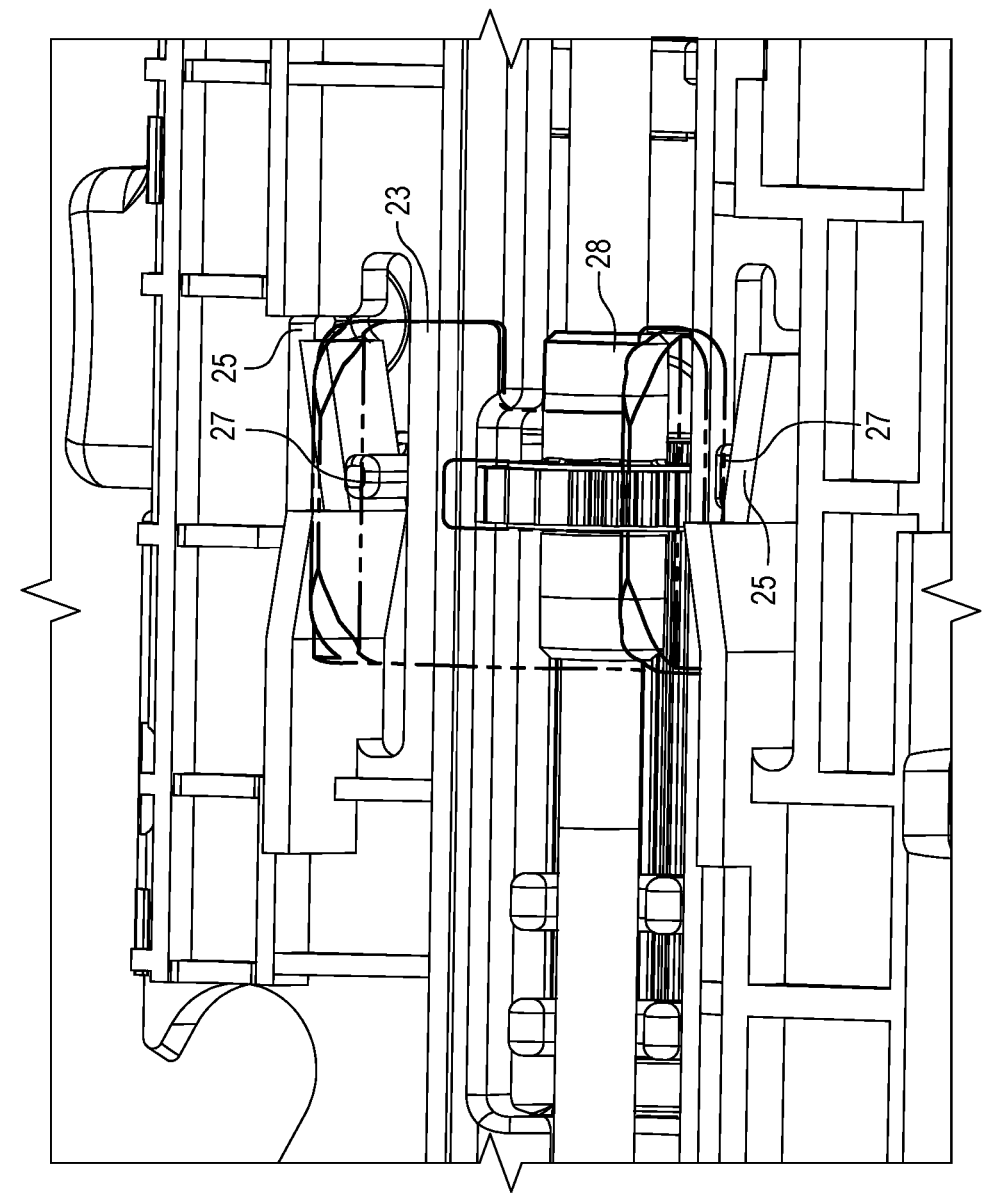
Figure 38:
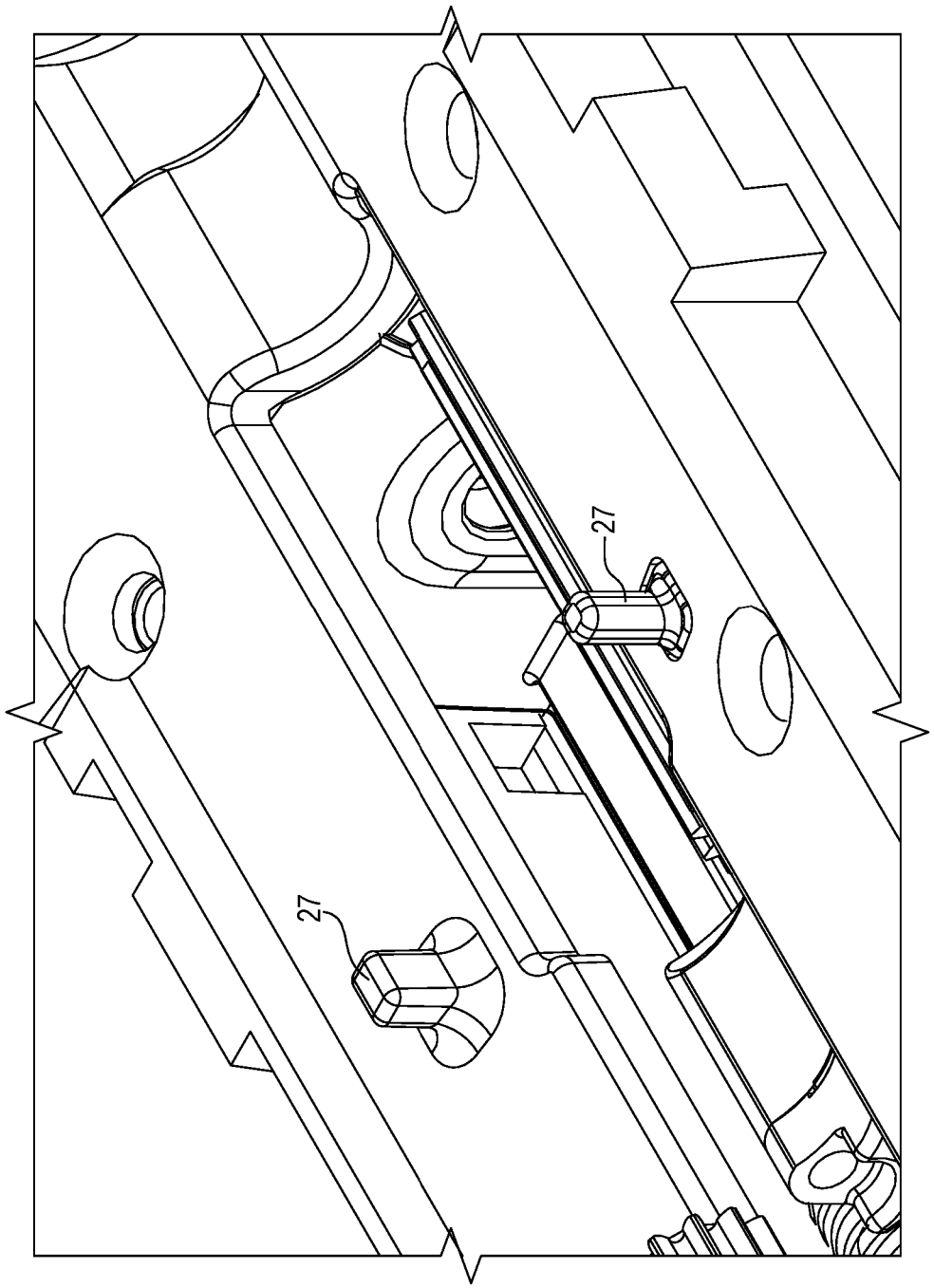
FIG. 38 is a detailed top perspective view of the reusable portion of the biopsy device depicted in FIGS. 1 to 7, with various components omitted for clarity.
Figure 39:
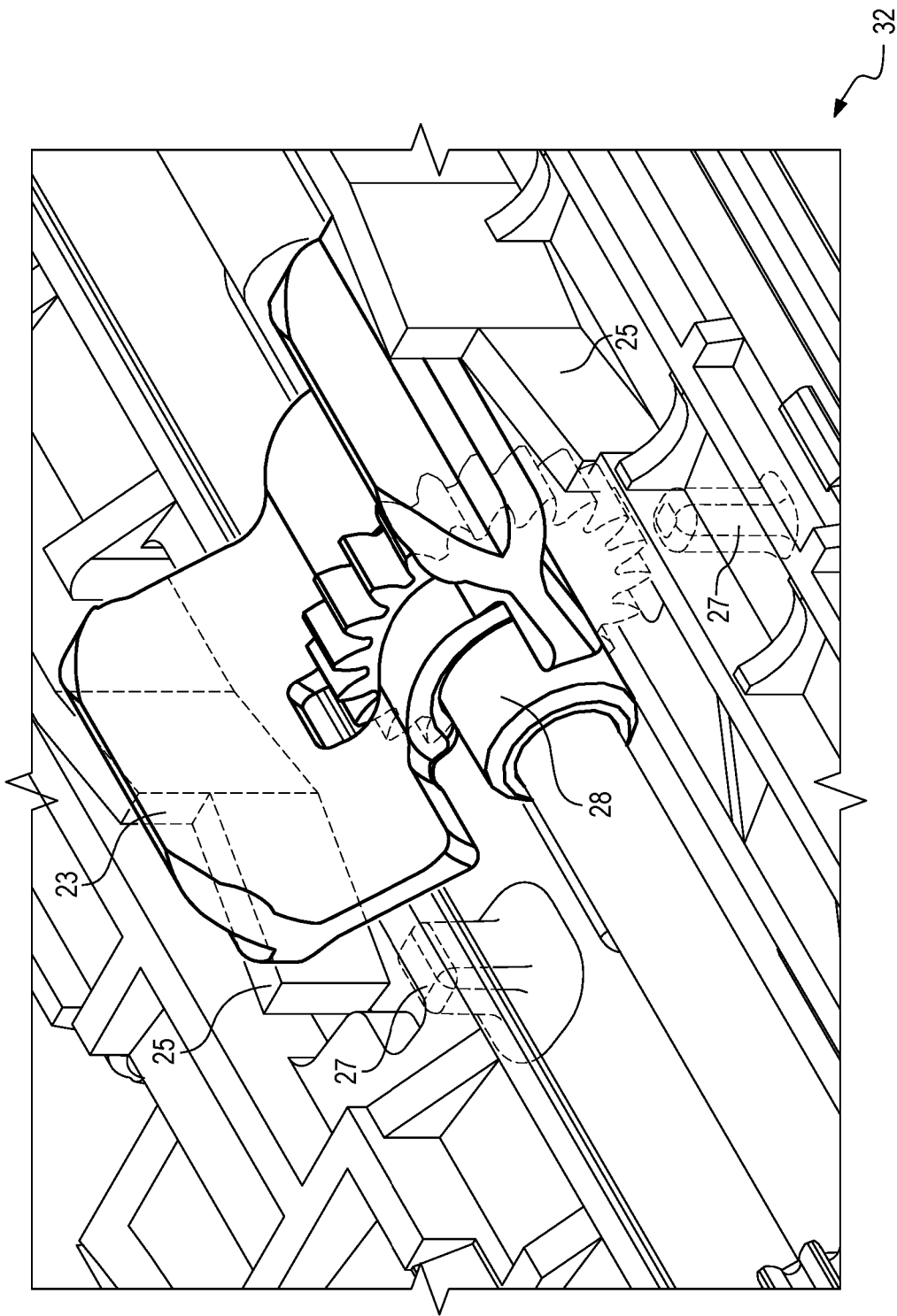
FIG. 39 is a detailed top perspective view of the biopsy device depicted in FIGS. 1 to 7, with various components omitted and others shown in phantom for clarity.

In order to maintain the disposable portion 16 of the biopsy device 10 in its shipping or home position during shipping, the disposable portion 16 includes a pair of transport tabs 25, which lock the outer and inner cannula hubs 26, 28 in their shipping or home positions, as shown in FIGS. 36 and 37. The tabs 25 prevent axial movement of the inner cannula hub 28 via an interference fit with the sliding support member 23 attached thereto. The reusable portion 32 of the biopsy device 10 includes a pair of pins 27 corresponding to the tabs 25 on the disposable portion 16, as shown in FIG. 38. The pins 27 are configured to move the tabs 25 away from the outer and inner cannula hubs 26, 28 when the disposable and reusable portions 16, 32 of the biopsy device 10 are attached to each other, as shown in FIG. 39. After the tabs 25 are moved away from the outer and inner cannula hubs 26, 28 by the pins 27, the outer and inner cannula hubs 26, 28 are free to travel axially.

Figure 22B:
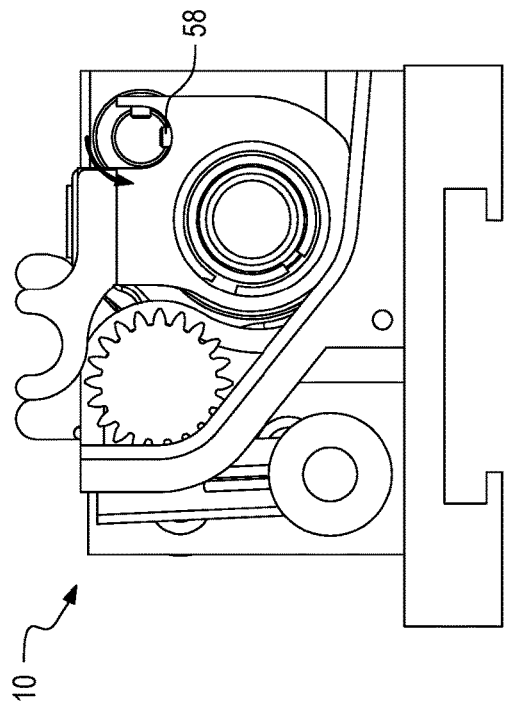

In step 102, the biopsy device 10 is pre-armed by rotating the cam 60 to lock the outer cannula drive assembly 34, and rotating the lead screw 82 to retract the unlocked inner cannula drive assembly 46 in the proximal direction. Retraction of the inner cannula drive assembly 46 can be seen by comparing FIG. 21a to FIGS. 21b and 21c. Rotation of the cam 60 to lock the outer cannula drive assembly 34 is shown in FIG. 22b.

After the disposable and reusable portions 16, 32 of the biopsy device 10 are attached to each other, and the biopsy device 10 is armed (described below), but before the biopsy device 10 is fired (also described below), the biopsy device 10 is secured to a stereotactic table and the tissue piercing tip 20 is inserted through the skin of the patient before the biopsy device 10 is armed and fired. Inserting the tissue piercing tip 20 through the skin before firing prevents tenting of the skin during firing, which may decrease the accuracy with which the tissue receiving opening 22 is positioned adjacent target tissue. Firing through skin also increases patient discomfort and tissue damage.

In step 104, the biopsy device 10 the arming step continues by rotating the cam 60 to lock the fully retracted inner cannula drive assembly 46 and to unlock the outer cannula drive assembly 34. The arming step is continued by rotating the lead screw 82 to retract the unlocked outer cannula drive assembly 34 in the proximal direction. As the outer cannula drive assembly 34 is retracted proximally, the firing spring 88 is compressed as described above. However, the firing spring 88 is prevented from firing because the lead screw 82 links the outer cannula drive assembly 34 to the inner cannula drive assembly 46, which is locked in its axial position by the cam 60. Retraction of the outer cannula drive assembly 34 to arm the biopsy device can be seen by comparing FIG. 21c to FIGS. 21d and 21e. Rotation of the cam 60 to lock the inner cannula drive assembly 46 and unlock the outer cannula drive assembly 34 is shown in FIG. 22d.

In step 106, the biopsy device 10 is fired by rotating the cam 60 to unlock the inner cannula drive assembly 46 while the outer cannula drive assembly 34 remains unlocked. Unlocking the inner cannula drive assembly 46 allows the firing spring 88 to expand to its relaxed condition, thereby propelling the outer cannula drive assembly 34, and the inner cannula drive assembly 46 linked thereto by the lead screw 82, in a distal direction relative to the cam 60, the frame 31 and the housing 12. A firing stop can be used to control the deceleration of the linked components when they are fired. The material (durometer) from which the firing stop is constructed and the dimensions (thickness and area) thereof contribute to stopping the outer and inner cannulas 18, 24 at a precise location with the desired accuracy and without excessive movement (e.g., rebound, overshoot, bouncing and vibration). The material and dimensions of the firing stop also affect the noise associated with firing. During a procedure according to this embodiment, the outer and inner cannulas 18, 24 are fired into tissue with the inner cannula 24 closing the tissue receiving opening 22 in the outer cannula 18. Firing of the linked outer and inner cannula drive assemblies 34, 46 can be seen by comparing FIG. 21e to FIGS. 21f and 21g. Rotation of the cam 60 to unlock the inner cannula drive assembly 46 is shown in FIG. 22f.

Figure 22C:
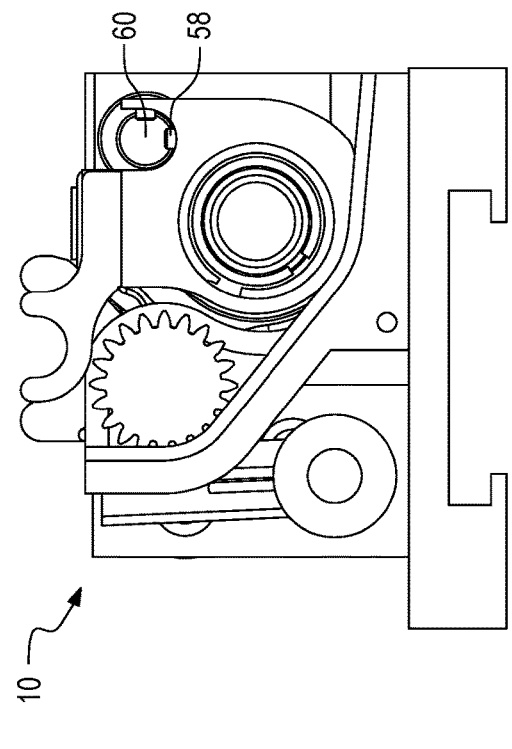
Figure 22D:
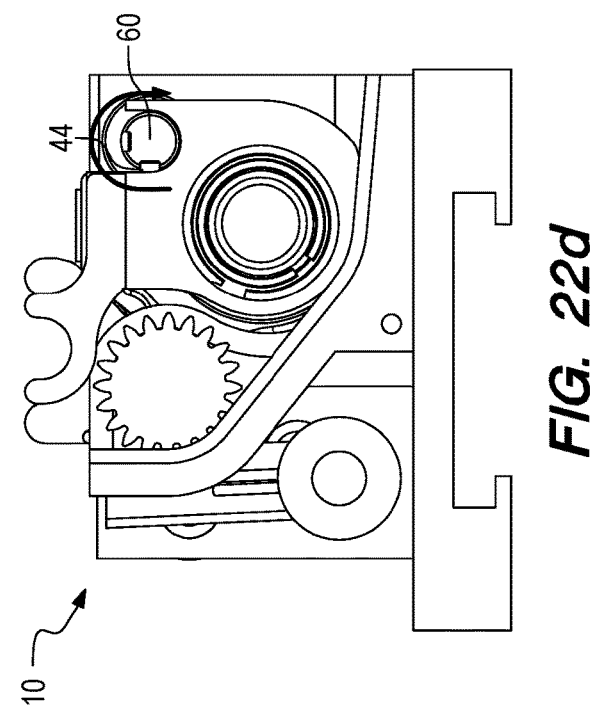
Figure 22H:
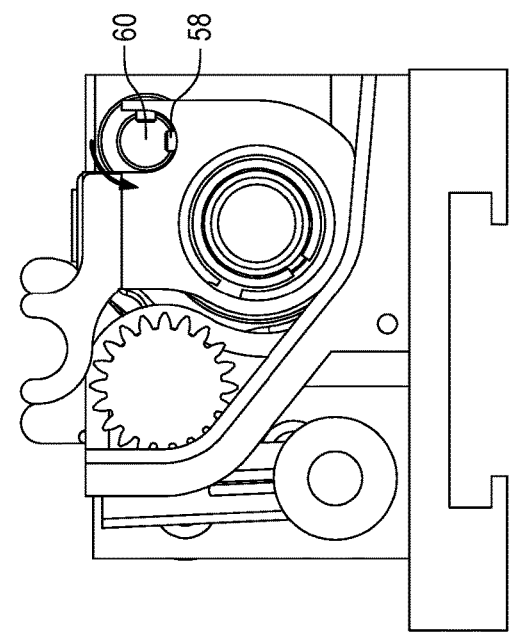
Figure 22I:
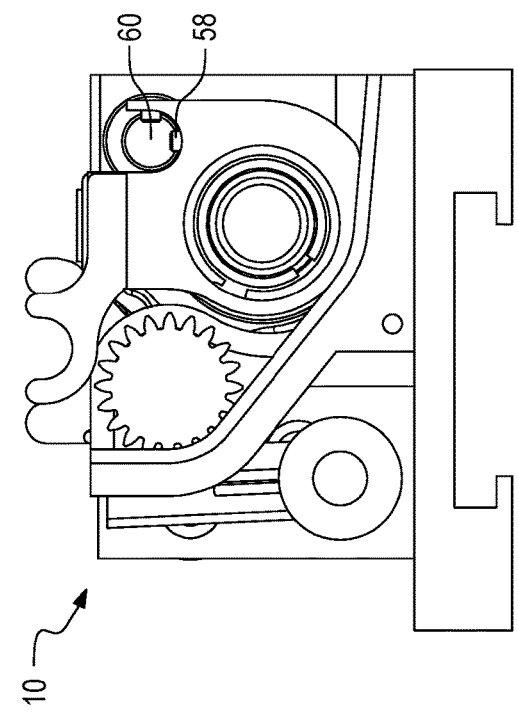
Figure 22J:
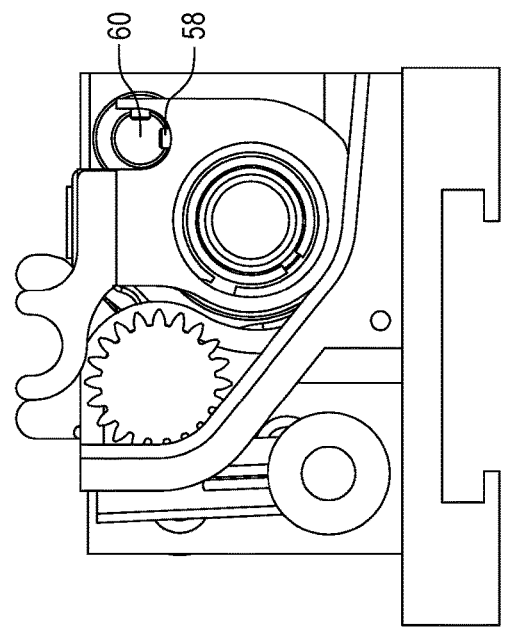

In step 108, the cam 60 is rotated to lock the outer cannula drive assembly 34 in its full distal fired position while the inner cannula drive assembly 46 remains unlocked. Rotation of the cam 60 to lock the outer cannula drive assembly 34 is shown in FIG. 22h. After the outer cannula 18 has been fired into tissue, the outer cannula drive assembly 34 remains locked in its full distal fired position for the remainder of the procedure 100. Consequently, the cam 60 is no longer rotated after the rotation depicted in FIG. 22h.

In step 110, the cutting cycle is initiated by rotating the lead screw 82 to retract the unlocked inner cannula drive assembly 46 in the proximal direction. Retraction of the inner cannula drive assembly 46 can be seen by comparing FIG. 21g to FIGS. 21h and 21i.

In step 112, the cutting cycle is continued by reversing the rotational direction of the motor and the lead screw 82 to advance the inner cannula drive assembly 46 and the distal direction. Advancement of the inner cannula drive assembly 46 can be seen by comparing FIG. 21i to FIGS. 21j and 21k.

In step 114, the cutting cycle is continued by continuing to rotate the lead screw 82 after the inner cannula drive assembly 46 has reached its full distal position. The continued rotation of the lead screw 82 compresses the dwell spring 86 in the outer cannula sleeve 42. Further, continued rotation of the lead screw 82 allows continued rotation of the inner cannula 24, via the inner cannula gear 30 and the spline 76, while the inner cannula 24 is forced against the cutting board 11 by the dwell spring 86. Continued rotation of the lead screw is depicted in FIG. 21k.

In step 116 cutting cycle is continued by again reversing the rotational direction of the motor 70 and the lead screw 82 to retract the inner cannula drive assembly 46 in the proximal direction. Retraction of the inner cannula drive assembly 46 can be seen by comparing FIG. 21k to FIGS. 21l and 21m. After the inner cannula drive assembly 46 is fully retracted, the biopsy procedure 100 can be continued with another stroke by repeating steps 112, 114 and 116. Alternatively, the biopsy procedure 100 can be terminated after either step 114 (tissue receiving opening 22 closed) or step 116 (tissue receiving opening 22 open).

The biopsy device 10 depicted in FIGS. 1 to 18 and 23 to 25 uses a single motor 70 to power the following functions during the biopsy procedure 100: (1) arming the outer and inner cannulas 18, 24 for firing; (2) retraction and advancement of the inner cannula 24 during the cutting cycle; (3) rotation of the inner cannula 24 during the cutting cycle; and (4) rotation of the inner cannula 24 during the dwell period. The following features facilitate the above listed functions: (1) the floating lead screw 82 supported by the lead screw adapter 80 and the outer cannula nut 40; (2) the lead screw adapter 80 allows the lead screw 82 to move axially while being rotated by the motor 70; and (3) the interaction between the cam 60 and the outer and inner cannula drive assemblies 34, 46 allows the lead screw 82 to selectively move the outer and inner cannulas 18, 24. Use of a single motor 70 reduces the size of the reusable portion 32, thereby reducing obstruction of the view for stereotactic images and potential interference with stereotactic tables.

Further, the lead screw 82 is connected to, and therefore maintains a distance between, the outer and inner cannula drive assemblies 34, 46. This feature ensures that the inner cannula 24 closes the tissue receiving opening 22 in the outer cannula 18 during firing of the outer and inner cannulas 18, 24 into tissue. In other words, this feature closes the tissue receiving opening 22 and maintains the closed state during firing.

Other embodiments of biopsy devices 10 can include belt, pulley and gear structures that allow the single motor 70 to power rotation of the inner cannula 18. The outer cannula 18 is manually rotated (via gears and an offset shaft connected to an outer cannula rotation control) to orient the tissue receiving opening 22 adjacent target tissue. In alternative embodiments that do not require the ability to fire the outer and inner cannulas 18, 24, the motor for the cam 60 (or the cam 60 itself) could drive the gear that is attached to the outer cannula 18 to rotate the tissue receiving opening 22. The controller can be configured to allow a user to select automated rotation patterns for or manual rotation of the outer cannula 18. For automated rotation of the outer cannula 18, an intermittent motion mechanism (e.g., the Geneva intermittent drive mechanism) can allow rotation of the lead screw 82 to rotate the outer cannula 18 a fixed amount every time the lead screw 82 rotates the fixed number of times. A ratchet or cam/ramp mechanism (e.g., a clock wheel or motorcycle shifter mechanism) can allow cycling of the inner cannula 24 to rotate the outer cannula 18 a fixed amount each time the inner cannula 24 moves through a cycle. Linking rotation of the outer cannula 18 to either rotation of the lead screw 82 or cycling of the inner cannula 24 would result in automatic rotation of the outer cannula 18 linked to the cutting cycle without additional electronics.

Alternatively or additionally, the processor on the PC board 94 can be programmed to vary the retracting/firing distance by changing the proximal most distance of the inner cannula drive assembly 46. In such embodiments, there are two or more different retracting/firing distances. For a standard firing distance, the inner cannula drive assembly 46 is fully retracted (e.g., 25 mm). For a second distance, in "petite" applications, a second circumferential slot (not shown) for locking the inner cannula drive assembly 46 is located 8 mm distal of the first circumferential slot 66 (for standard distance) on the grooved cam 60. For instance, in "petite" applications, the inner cannula drive assembly 46 is retracted 17 mm. Retracting and firing the inner cannula drive assembly 46 a shorter distance in "petite" applications results in retracting and firing the outer cannula drive assembly 34 a shorter distance because retraction of the outer cannula drive assembly 34 is halted by contact with the inner cannula drive assembly 46. Retracting and firing the outer cannula drive assembly 34 a shorter distance allows the user to insert the tissue piercing tip 20 of the armed outer cannula 18 a short distance through the skin and into a petite breast while minimizing the possibility that the tissue piercing tip 20 of the outer cannula 18 will be fired through the breast tissue into which it was pre-inserted before firing. In other embodiments, there are more than two retracting/firing distances determined by the number of circumferential locking slots.

FIGS. 40 to 47 depict the outer and inner cannula drive assemblies 34, 46 and elongated cam 200 of a reusable portion 32 of a two-part biopsy device 10 according to another embodiment. The drive assemblies 34, 46 and elongated cam 200 depicted in FIGS. 40 to 47 are similar to those depicted in FIGS. 10 to 18. However, among other differences, instead of the grooved cam 60 depicted in FIGS. 10 to 18, the elongated cam 200 has raised lobes 202-1, 202-2, 204, 206. The first and second lobes 202-1, 202-2 are configured to selectively interact with an inner cannula strike plate 208 coupled to a distal surface of the inner cannula nut 54, as described below. The third lobe 204 is configured to selectively interact with an outer cannula strike plate 210 coupled to a proximal surface of the outer cannula nut 40, as described below. The fourth lobe 206 is configured to selectively interact with a vertical cam follower 212. The vertical cam follower 212 is configured to selectively open an aspirate valve of an aspiration vent as described in U.S. Provisional Patent Application Ser. No. 62/055,338, filed Sep. 25, 2014, and PCT Patent Application PCT/US2015/052017, filed Sep. 24, 2015. Both of these applications are assigned to the same assignee as the instant application, and the full contents thereof are hereby incorporated by reference as though fully set forth herein. The elongated cam 200 also includes first and second encoding discs 17-1, 17-2, which are described in detail in the description of FIGS. 48-52 below.

Figure 40:
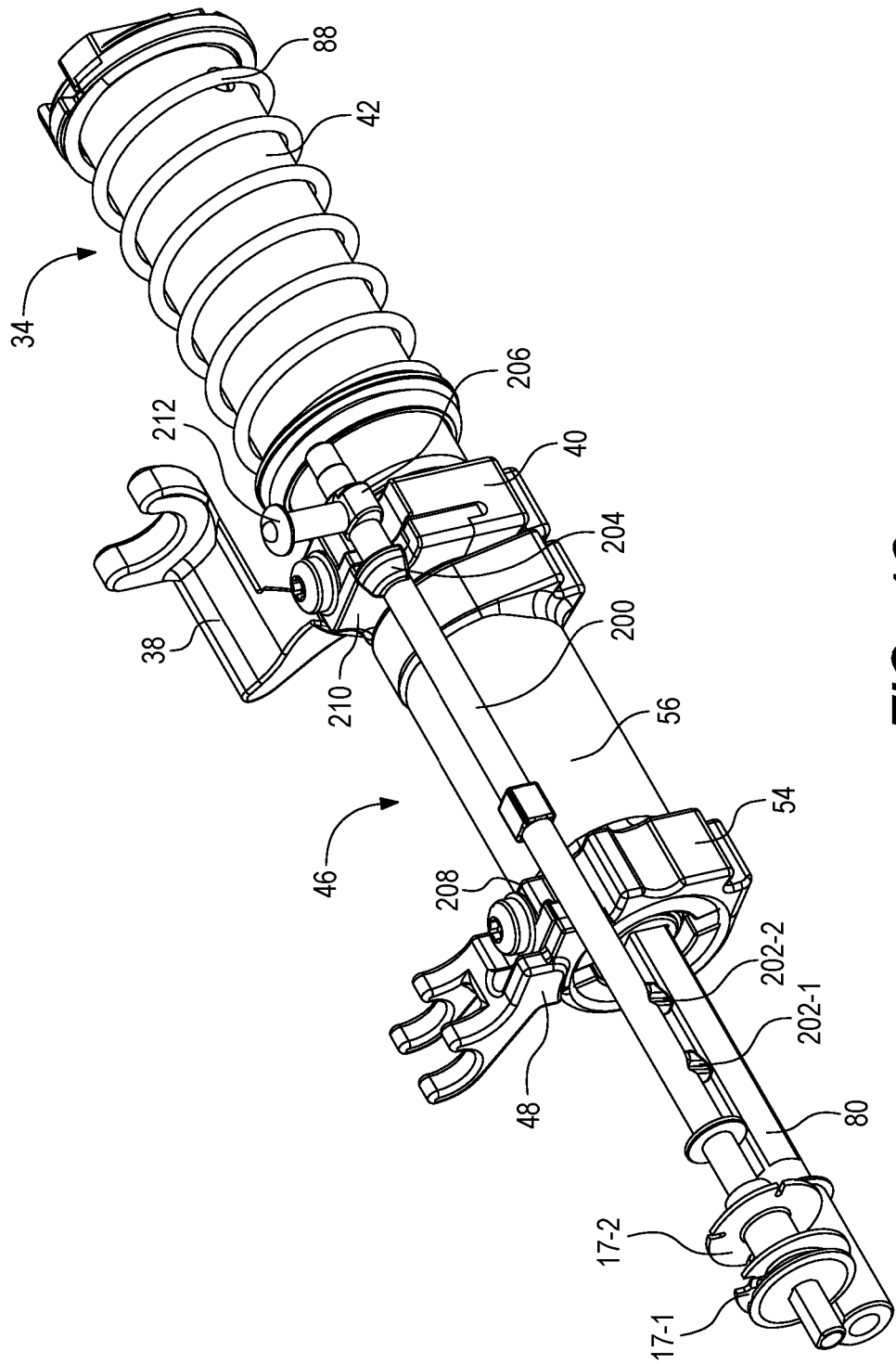
FIGS. 40 to 47 are perspective views of the outer and inner cannula assemblies and elongate cam of a reusable portion of a two-part biopsy device according to another embodiment.

FIG. 40 depicts the outer and inner cannula drive assemblies 34, 46 and elongated cam 200 in the "shipping" or "home" position previously depicted in FIG. 21a for a similar embodiment. In this position, both the outer and inner cannula drive assemblies 34, 46 are in their respective distal-most positions. The cam 200 is rotated such that the first and second lobes 202-1, 202-2 do not interact with the inner cannula strike plate 208, and the third lobe 204 does not interact with the outer cannula strike plate 210. Accordingly, the first and second lobes 202-1, 202-2 and the third lobe 204 do not prevent axial movement of the respective inner and outer cannula drive assemblies 46, 34. However, transport tabs prevent axial movement of the outer and inner cannula drive assemblies 34, 46, as described above. The fourth lobe 206 is rotated such that the vertical cam follower 212 is in a lowered position.

Figure 21C:
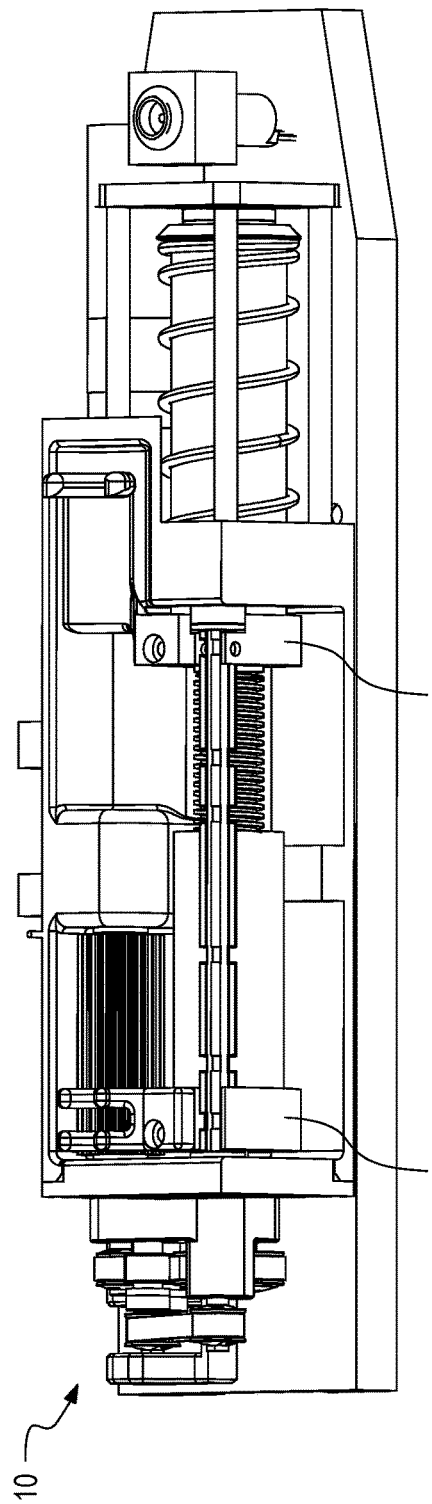
Figure 21D:
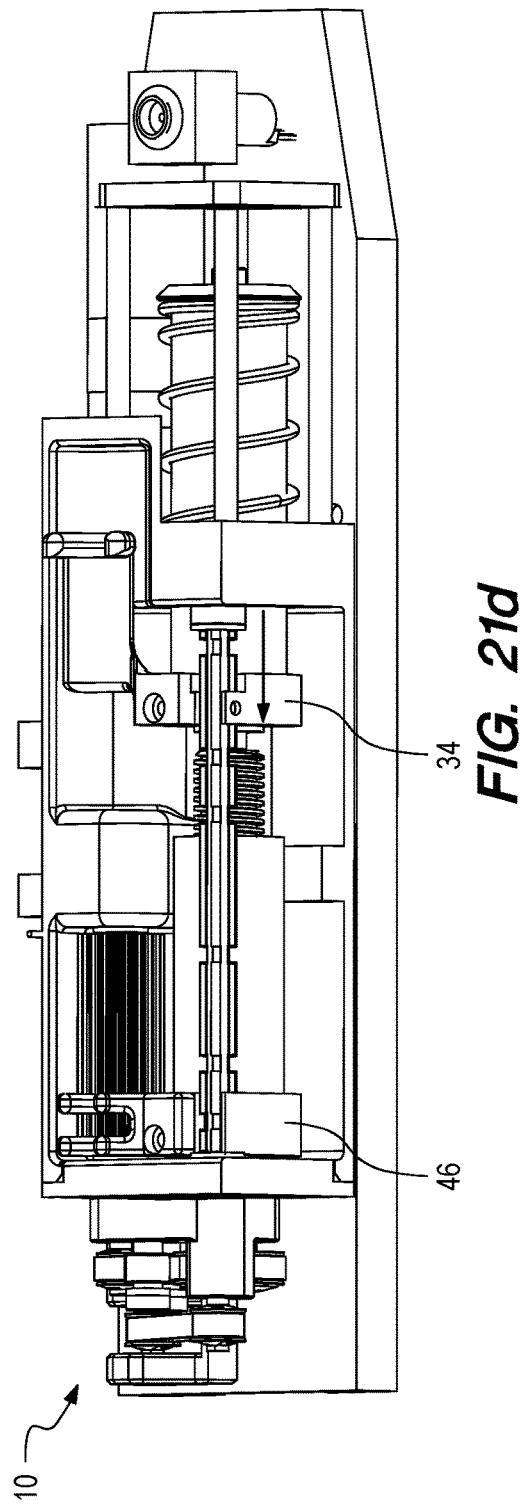
Figure 41:
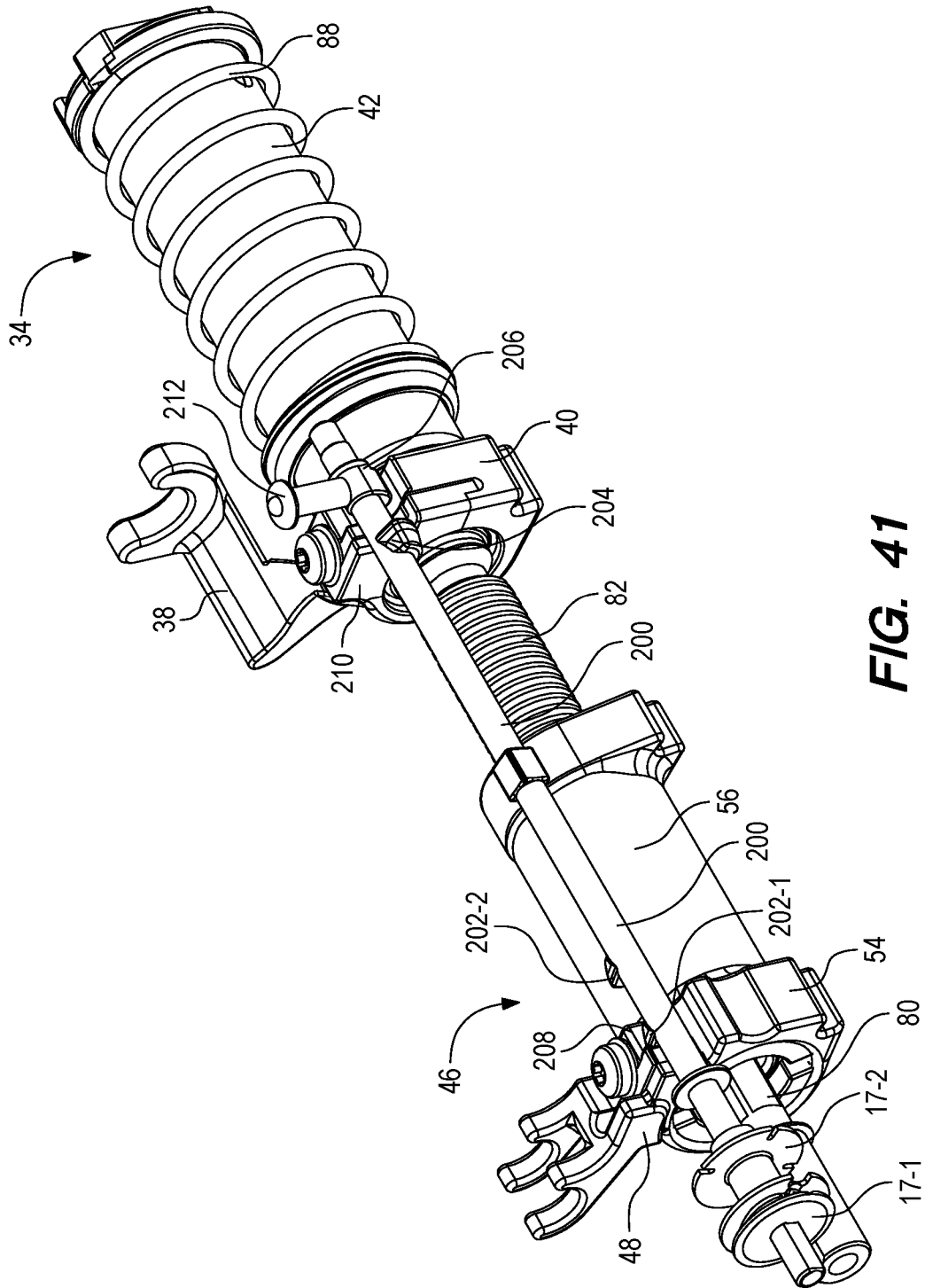

FIG. 41 depicts the outer and inner cannula drive assemblies 34, 46 and elongated cam 200 in the "pre-armed" position as previously depicted in FIG. 21c for a similar embodiment. In this position, the outer cannula drive assembly 34 remains in its distal-most (i.e., fired) position, while the inner cannula drive assembly 46 has been moved to its proximal-most position by the motor, as described above. Before the motor is rotated to move the inner cannula drive assembly 46, the cam 200 is rotated such that the first and second lobes 202-1, 202-2 do not interact with the inner cannula strike plate 208, but the third lobe 204 interacts with the outer cannula strike plate 210 (not shown, but see FIG. 44), preventing proximal axial movement of the outer cannula drive assembly 34. Accordingly, when the motor rotates, the inner cannula drive assembly 46 moves proximally, while the outer cannula drive assembly 34 remains substantially immobile. The fourth lobe 206 is rotated to another position in which the vertical cam follower 212 is in a lowered position. In the "pre-armed" position, the cam 200 is rotated such that the third lobe 204 does not interact with the outer cannula strike plate 210, but the first lobe 202-1 interacts with the inner cannula strike plate 208, preventing distal axial movement of the inner cannula drive assembly 46.

Figure 21E:
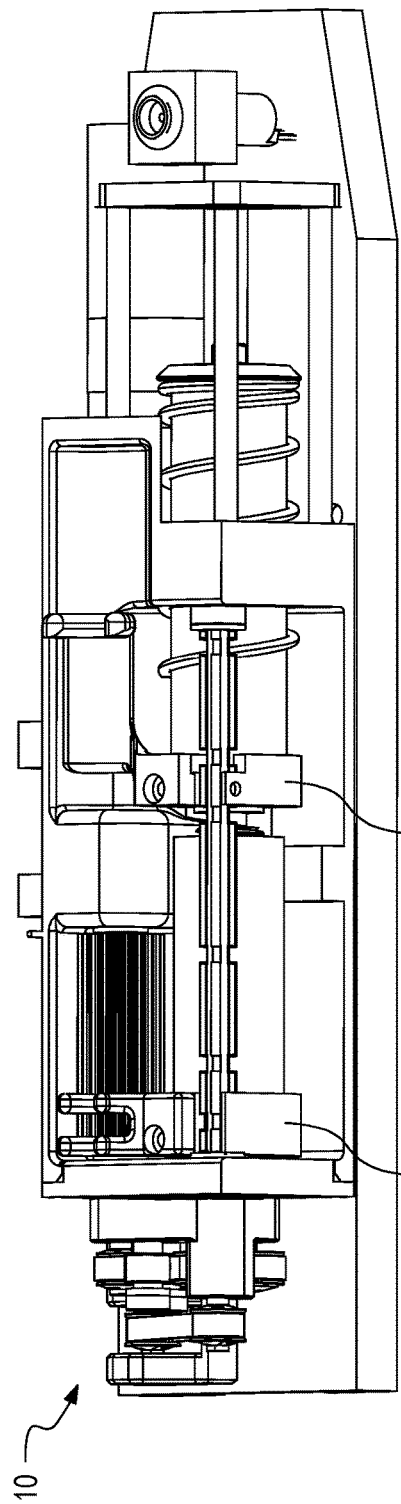
Figure 22E:
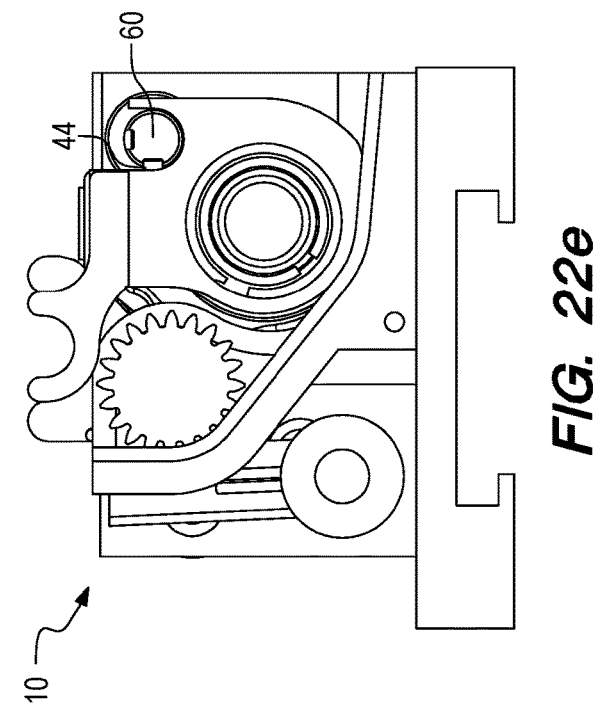
Figure 42:
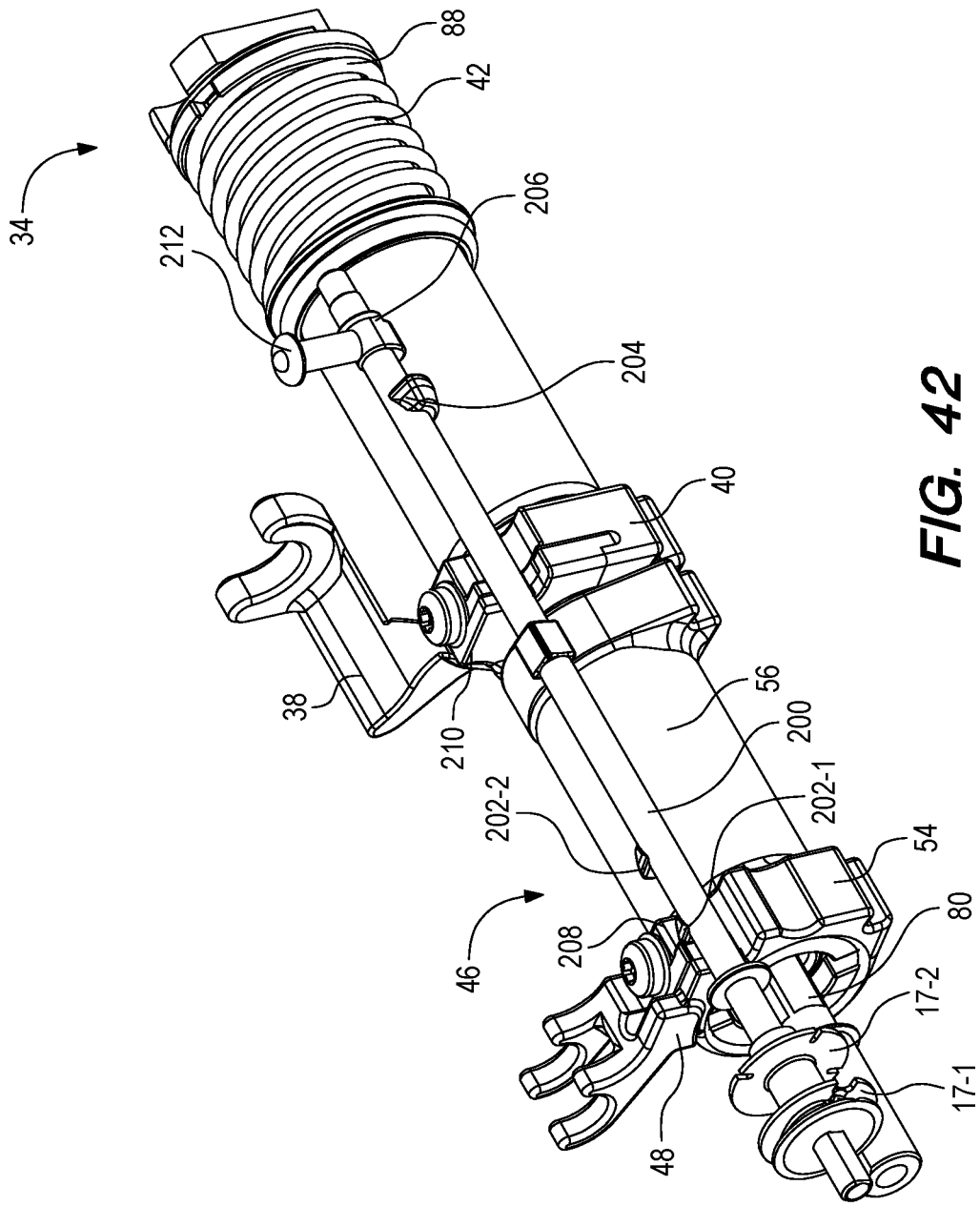

FIG. 42 depicts the outer and inner cannula drive assemblies 34, 46 and elongated cam 200 in their respective proximal-most positions as previously depicted in FIG. 21e for a similar embodiment. The outer cannula drive assembly 34 has been moved there by the motor, as described above. Because the cam 200 is rotated such that the third lobe 204 does not interact with the outer cannula strike plate 210, but the first lobe 202-1 interacts with the inner cannula strike plate 208, when the motor rotates, the outer cannula drive assembly 34 moves proximally, while the inner cannula drive assembly 46 remains substantially immobile. The fourth lobe 206 is rotated to still another position in which the vertical cam follower 212 is in a lowered position. When the outer cannula drive assembly 34 moves to its proximal-most armed position, it compresses the firing spring 88, thereby arming the device 10, as described above. The first lobe 202-1 holds the outer and inner cannula drive assemblies 34, 46 in their respective proximal-most positions, and the firing spring 88 in its compressed condition. The outer and inner cannula drive assemblies 34, 46 are axially coupled by the lead screw, as described above.

Figure 21G:
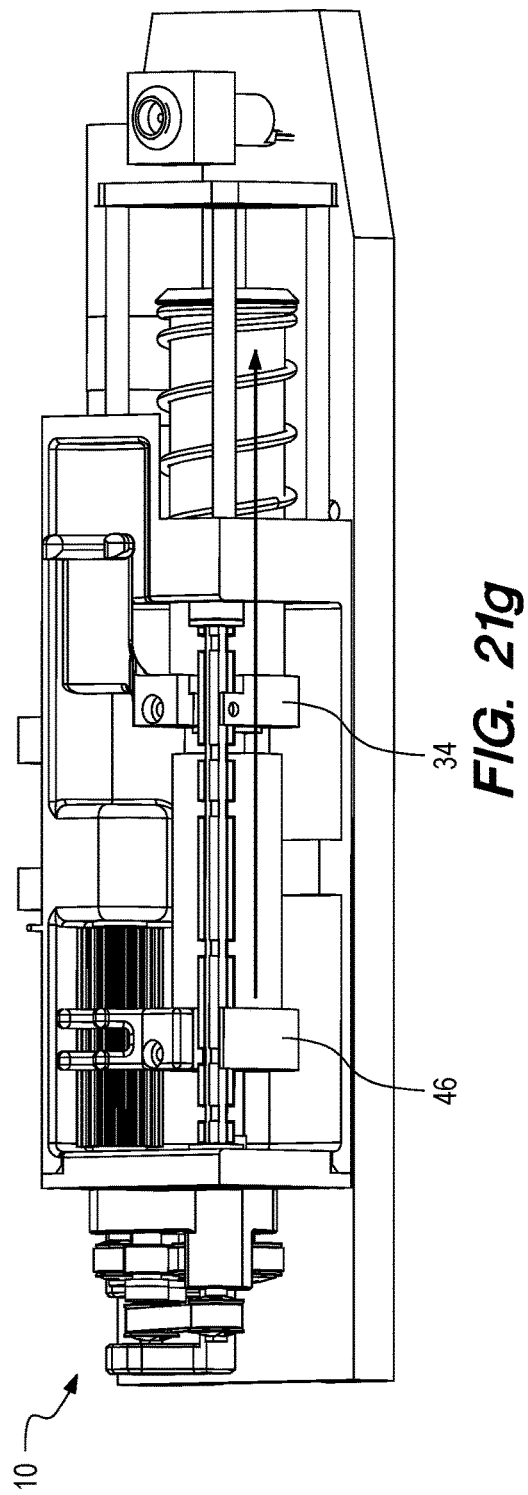
Figure 22G:
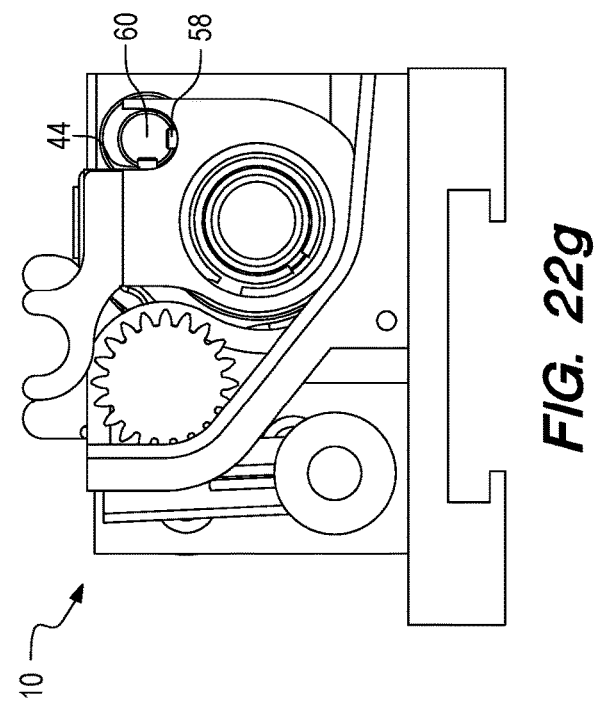
Figure 43:
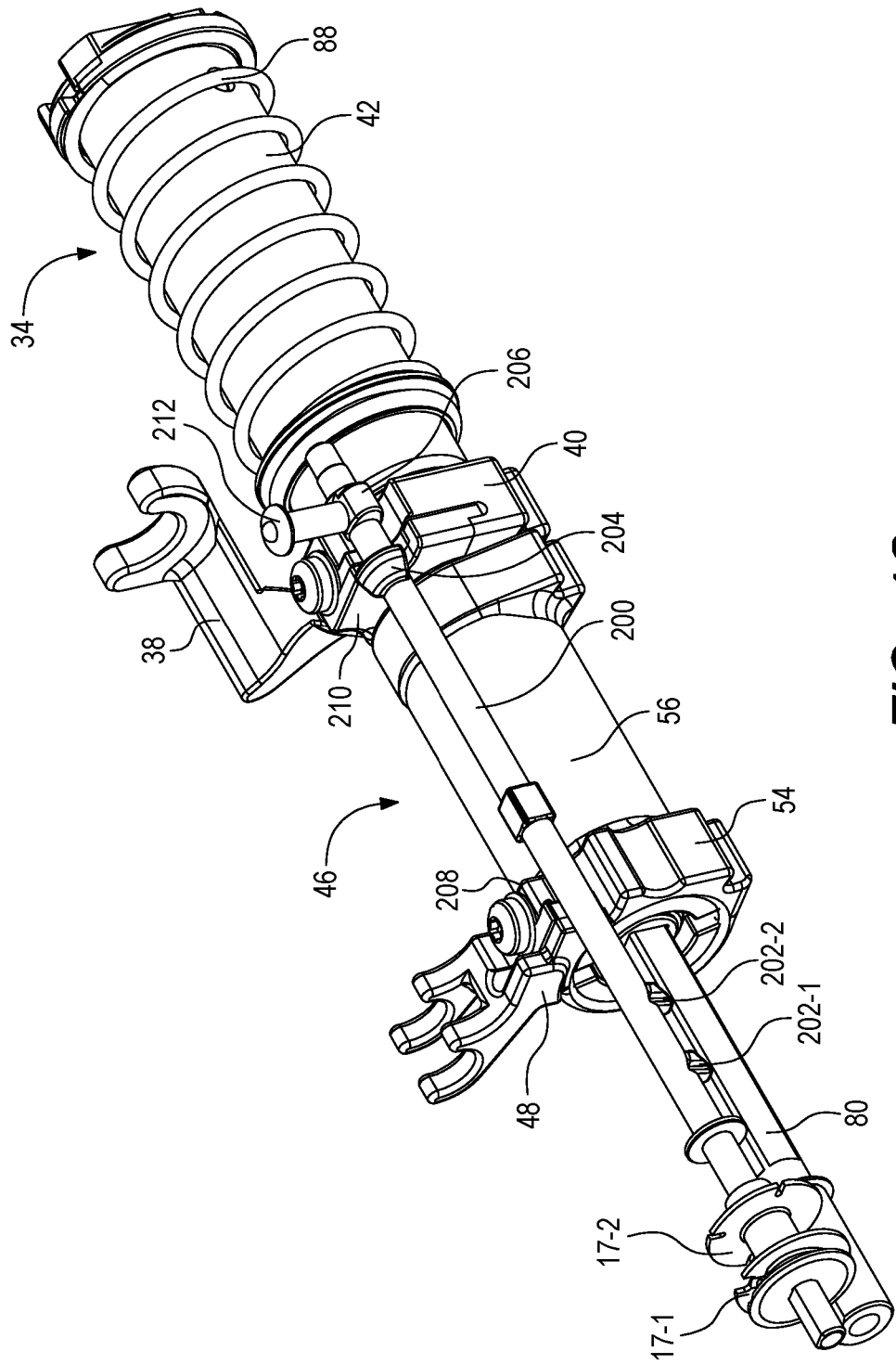

FIG. 43 depicts the outer and inner cannula drive assemblies 34, 46 and elongated cam 200 in distal-most positions as previously depicted in FIG. 21g for a similar embodiment. The outer and inner cannula drive assemblies 34, 46 have been moved there by expansion of the firing spring, as described above. Expansion of the firing spring is triggered by rotation of the cam 200 to a position such that the first and second lobes 202-1, 202-2 do not interact with the inner cannula strike plate 208, and the third lobe 204 does not interact with the outer cannula strike plate 210. When the cam 200 is rotated such that the first lobe 202-1 no longer holds the firing spring 88 in its compressed condition, the firing spring 88 elongates, translating both the outer and inner cannula drive assemblies 34, 46 distally. The fourth lobe 206 is rotated to yet another position in which the vertical cam follower 212 is in a lowered position.

Figure 21H:
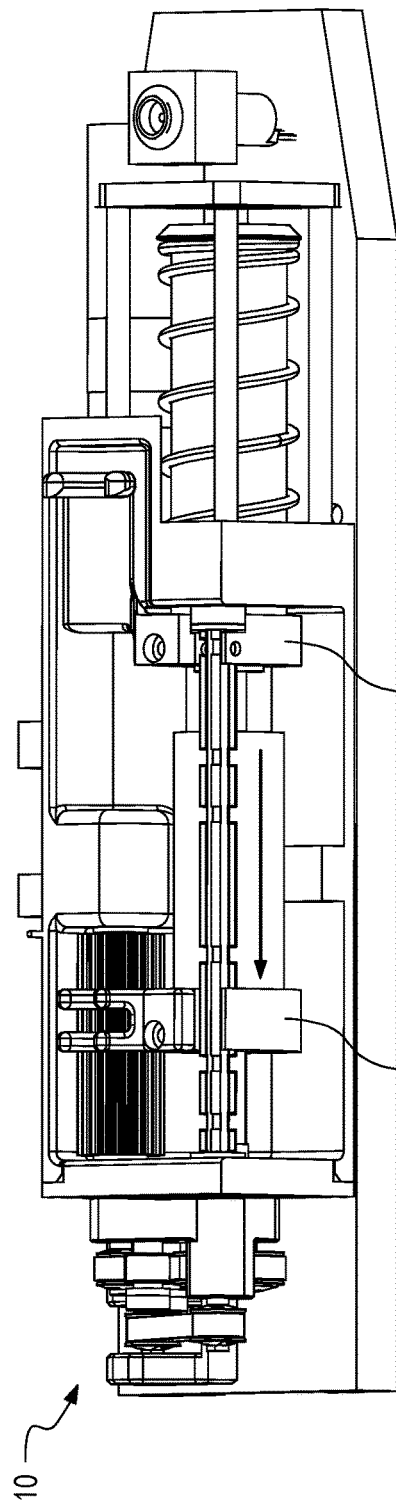
Figure 21I:
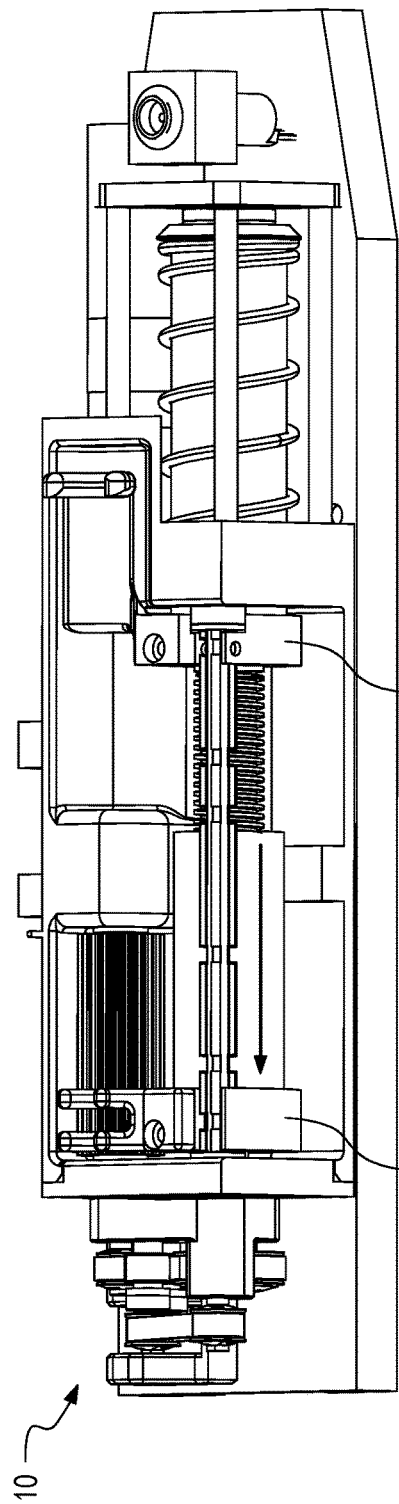
Figure 21J:
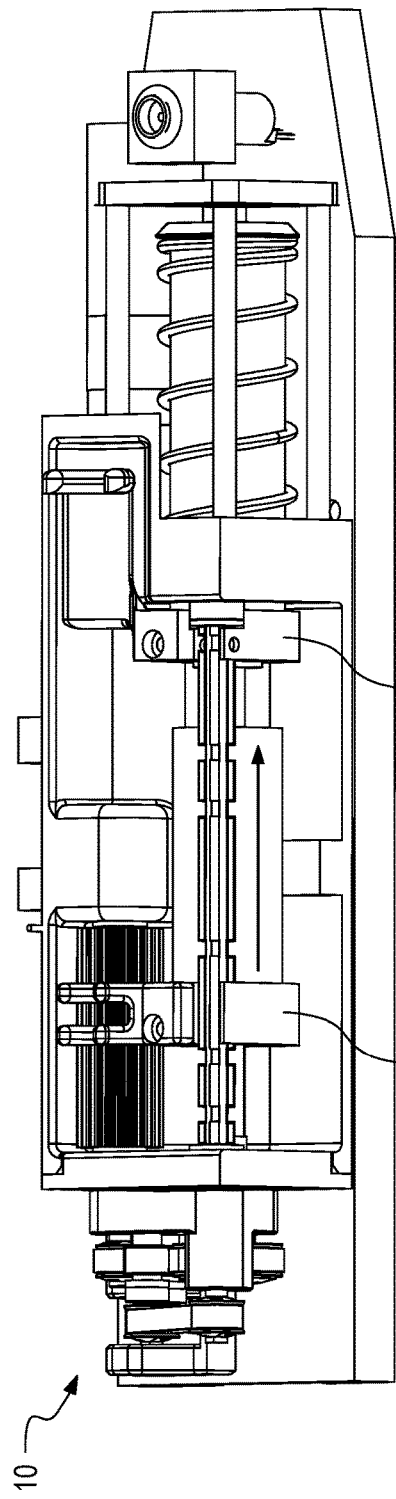
Figure 21K:
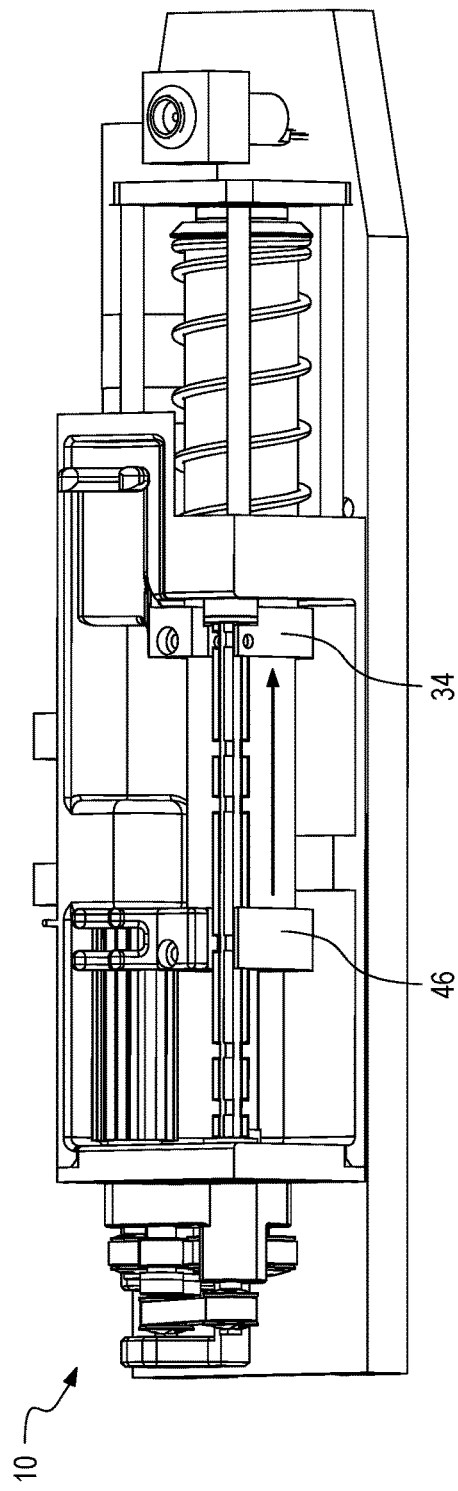
Figure 22K:
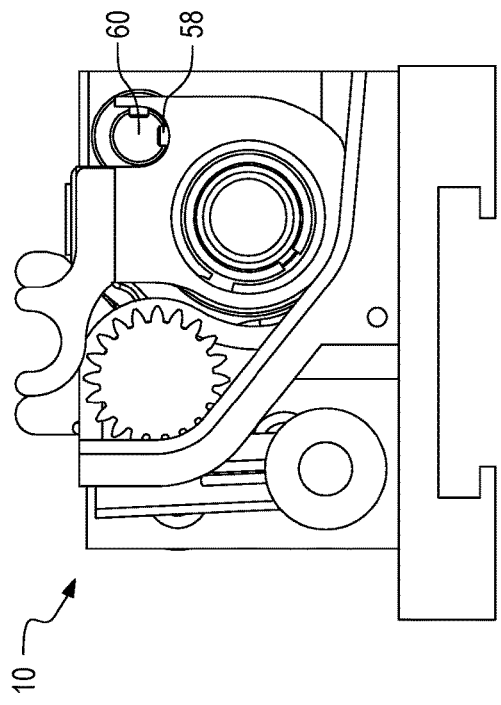
Figure 21I:
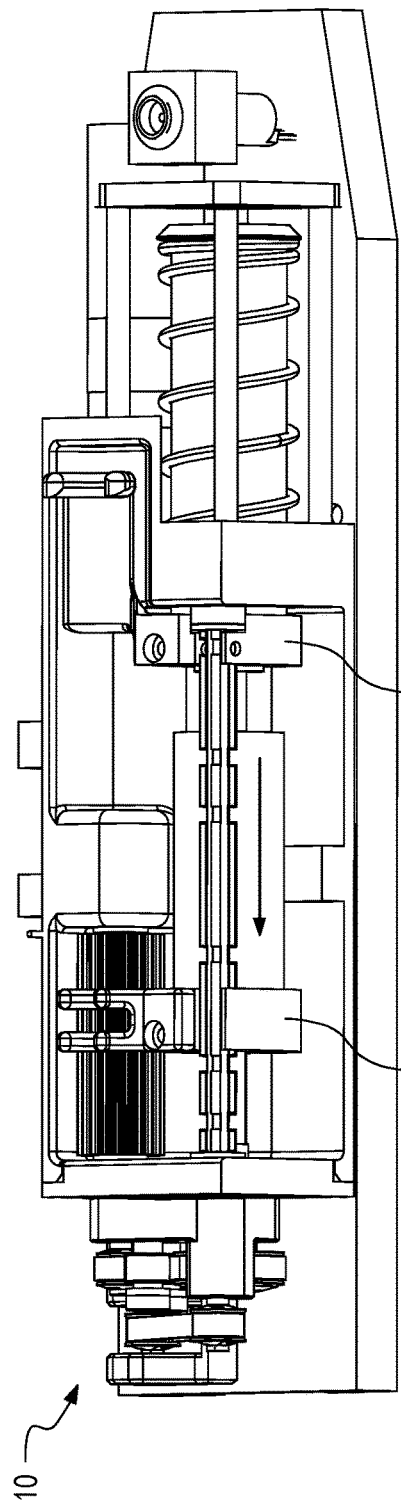
Figure 22I:
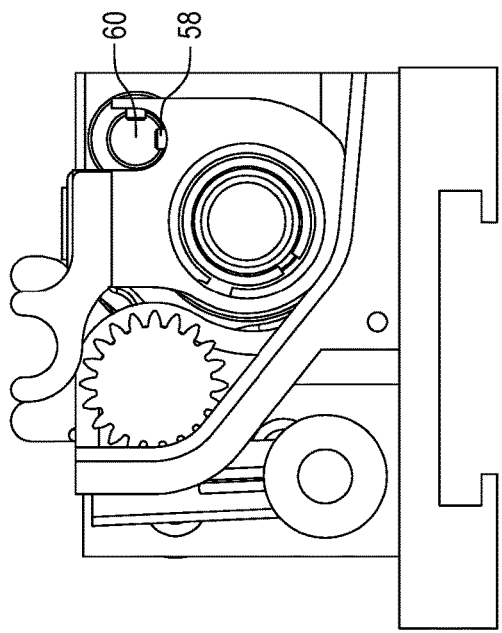
Figure 44:
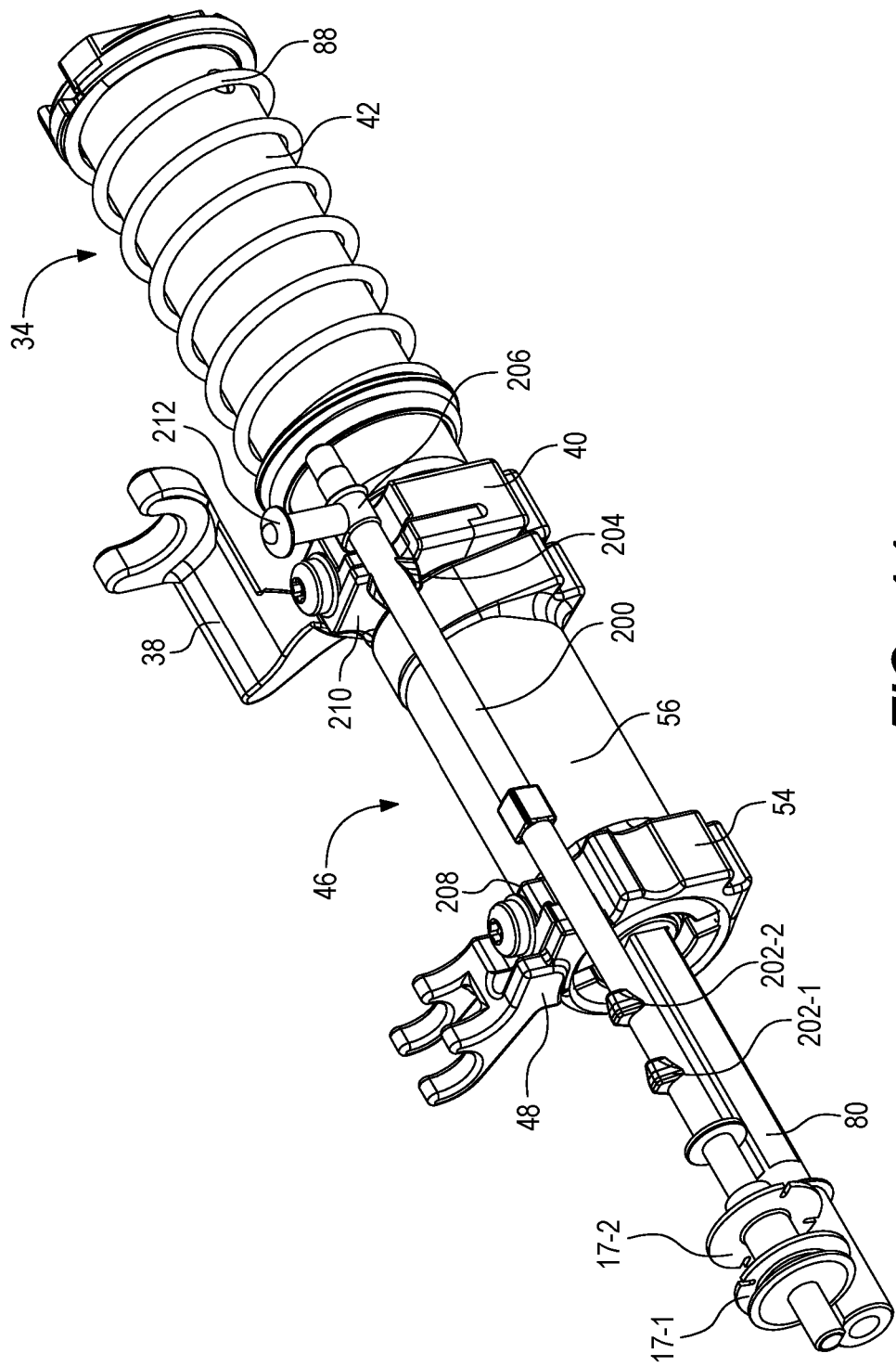

FIG. 44 depicts the outer and inner cannula drive assemblies 34, 46 and elongated cam 200 in the "begin cutting cycle" position as previously depicted in FIG. 21h for a similar embodiment. In this position, both the outer and inner cannula drive assemblies 34, 46 remain in their respective distal-most positions. This position is similar to the one depicted in FIG. 43, however, the cam 200 has been rotated such that the first and second lobes 202-1, 202-2 do not interact with the inner cannula strike plate 208, but the third lobe 204 interacts with the outer cannula strike plate 210, preventing proximal axial movement of the outer cannula drive assembly 34. Accordingly, rotation of the motor results in axial movement of the inner cannula drive assembly 46, powering the cutting cycle described above. The fourth lobe 206 is rotated to another position in which the vertical cam follower 212 is in a lowered position.

Figure 45:
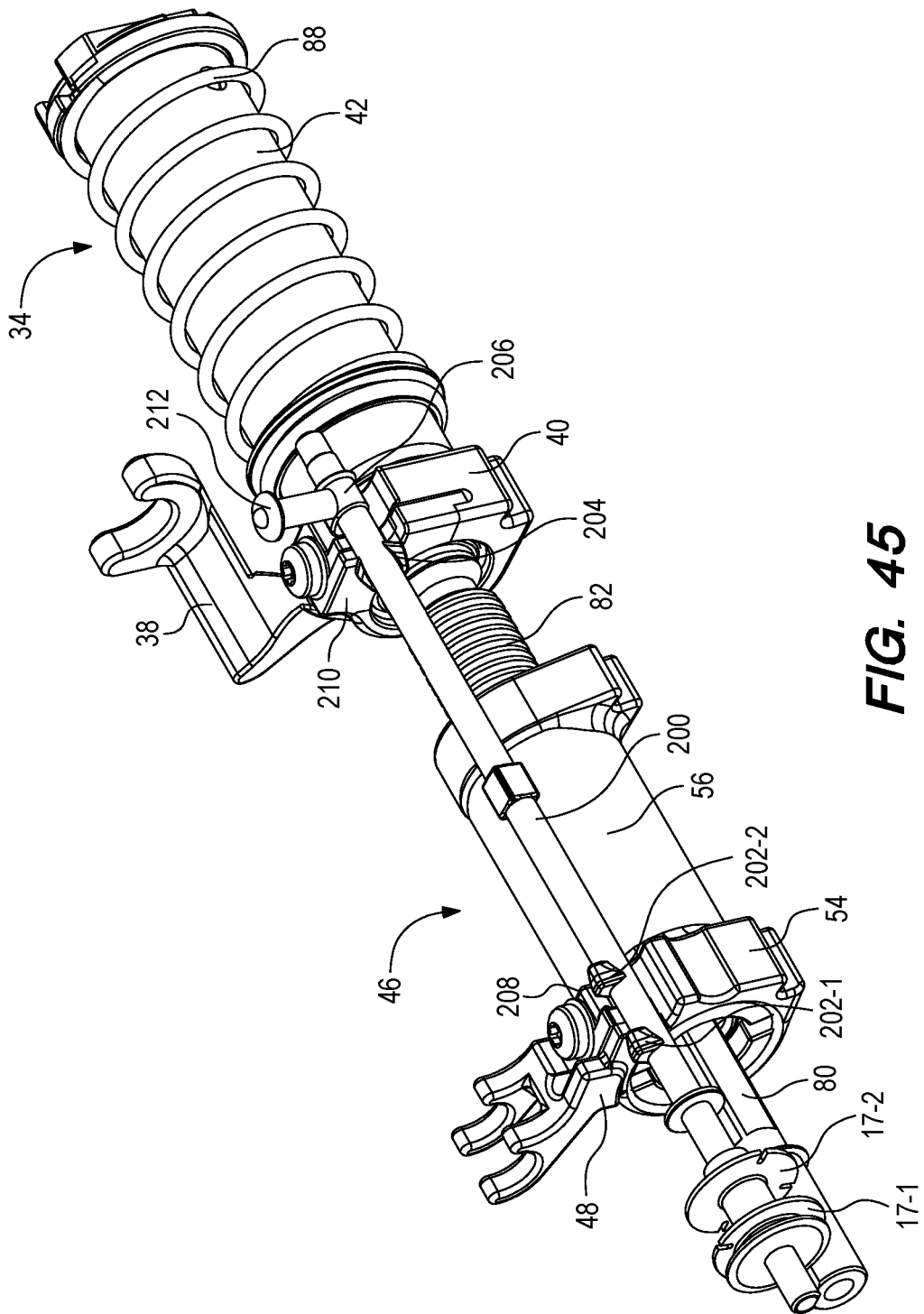

FIG. 45 depicts the outer and inner cannula drive assemblies 34, 46 and elongated cam 200 in the "cutting cycle-IC retracting" position as previously depicted in FIG. 21h for a similar embodiment. In this position, the outer cannula drive assembly 34 is locked in its distal-most (i.e., fired) position, while the inner cannula drive assembly 46 is being moved proximally by the motor, as described above. The fourth lobe 206 is rotated to another position in which the vertical cam follower 212 is in a lowered position.

The proximal motion of the inner cannula corresponding to the proximal motion of the inner cannula drive assembly 46 opens the tissue receiving opening to prepare for a cutting cycle. The cutting cycle begins when the inner cannula drive assembly 46 reaches its proximal-most position (driven by motor) as shown in FIG. 41, and as previously depicted in FIG. 21i for a similar embodiment, and begins moving distally from its proximal-most position. However, the outer cannula drive assembly is not locked in FIG. 41. The cutting cycle continues when the inner cannula drive assembly 46 begins moving distally (driven by motor) as shown in FIG. 45, and as previously depicted in FIG. 21j for a similar embodiment. The cutting cycle is completed when the inner cannula drive assembly 46 reaches its distal-most position (driven by motor) as shown in FIG. 444, and as previously depicted in FIG. 21k for a similar embodiment.

Figure 46:
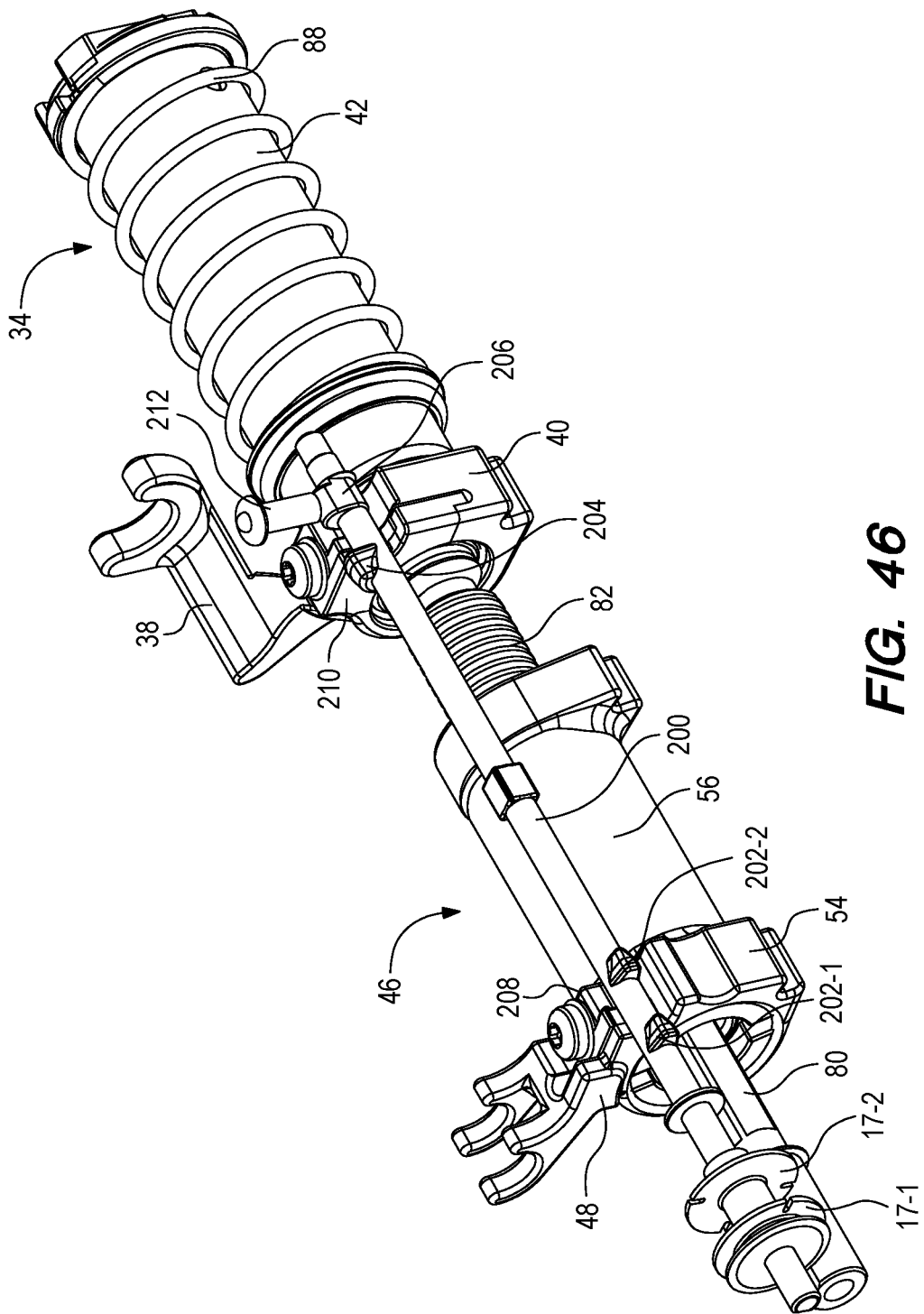

FIG. 46 depicts the outer and inner cannula drive assemblies 34, 46 and elongated cam 200 in the "cutting cycle-IC retracting" position as previously depicted in FIG. 21*l* for a similar embodiment. In this position, the outer cannula drive assembly 34 is locked in its distal-most (i.e., fired) position, while the inner cannula drive assembly 46 is being moved proximally by the motor, as described above. The fourth lobe 206 is rotated to another position in which the vertical cam follower 212 is in a lowered position. In the position depicted in FIG. 46, the cam 200 has been rotated during a retraction portion of the cutting cycle such that the fourth lobe 206 lifts the vertical cam follower 212 to aspirate a vacuum distal of excised tissue in the lumen of the inner cannula, as described in U.S. Provisional Patent Application Ser. No. 62/055,338, which has been previously incorporated by reference. While FIG. 46 depicts a timing of aspiration during the cutting cycle, aspiration may take place during any portion of the cutting cycle (especially ones where excised tissue is in the lumen of the inner cannula).

Figure 47:
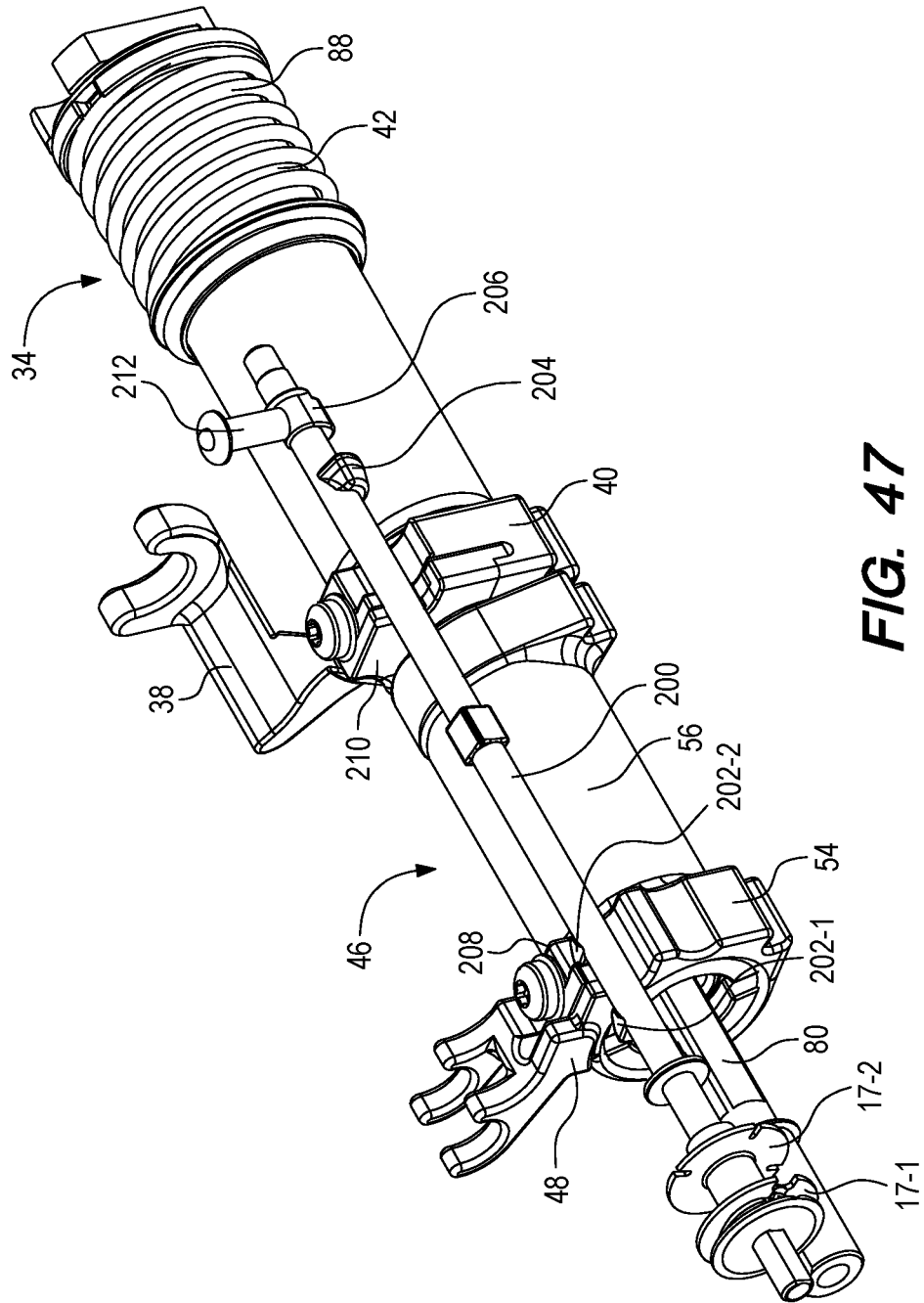

FIG. 47 depicts the outer and inner cannula drive assemblies 34, 46 and elongated cam 200 in the "petite armed" position. In this position, both the outer and inner cannula drive assemblies 34, 46 are in their respective petite proximal-most positions. The cam 200 is rotated such that the third lobe 204 does not interact with the outer cannula strike plate 210, but the second lobe 202-2 interacts with the inner cannula strike plate 208. The fourth lobe 206 is rotated to still another position in which the vertical cam follower 212 is in a lowered position. When the outer cannula drive assembly 34 moves to its proximal-most armed position, it compresses the firing spring 88, thereby arming the device 10, as described above. The second lobe 202-2 holds the outer and inner cannula drive assemblies 34, 46 in their respective petite proximal-most positions, and the firing spring 88 in its compressed condition. The outer and inner cannula drive assemblies 34, 46 are axially coupled by the lead screw, as described above. While only two armed positions are shown in FIGS. 40 to 47, the device may have any number of armed positions. Lobe and strike plate cam systems such as the one depicted in FIGS. 40-47 have greater tolerance than the groove and dowel cam systems described above.

Figure 48:
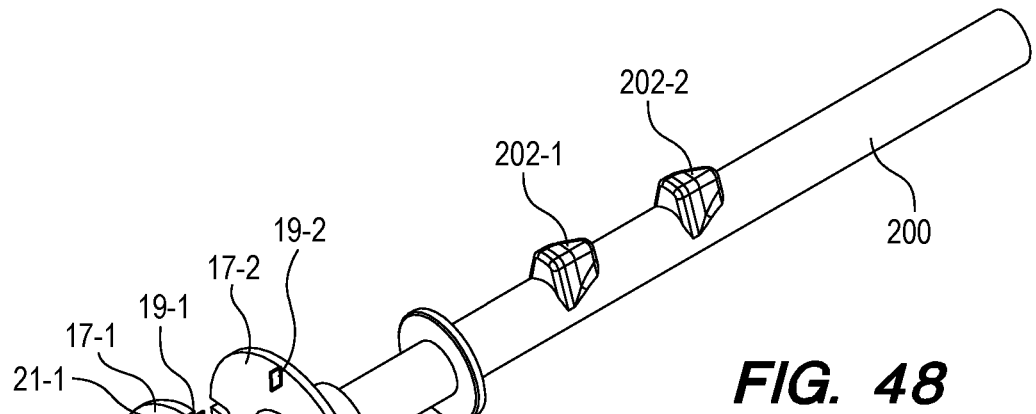
FIGS. 48 to 52 are perspective views of two encoding discs and a cam of the biopsy device depicted in FIGS. 40 to 47.
Figure 49:
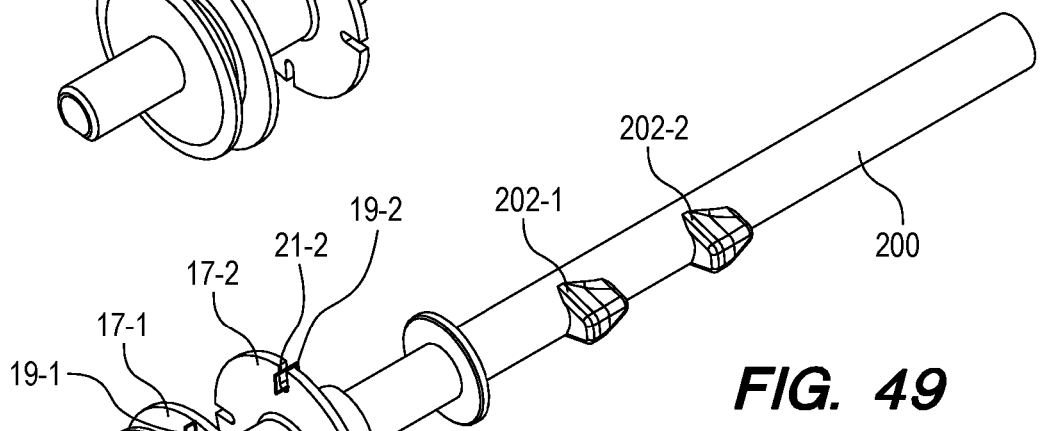

FIGS. 48-52 depict the cam 200 and first and second encoding discs 17-1, 17-2 coupled thereto. Various other components have been removed from these figures for clarity, including first and second sensors, similar to sensor 15 shown in FIG. 33. FIGS. 48-52 do show, however, first and second beams 19-1, 19-2 from each respective sensor. In FIG. 48 the cam 200 is rotated such that a first window 21-1 in the first encoding disc 17-1 allows the first beam 19-1 to pass, but the second encoding disc 17-2 blocks the second beam 19-2. In FIG. 49 the cam 200 is rotated such that a second window 21-2 in the second encoding disc 17-2 allows the second beam 19-2 to pass, but the first encoding disc 17-1 blocks the first beam 19-1.

Figure 50:
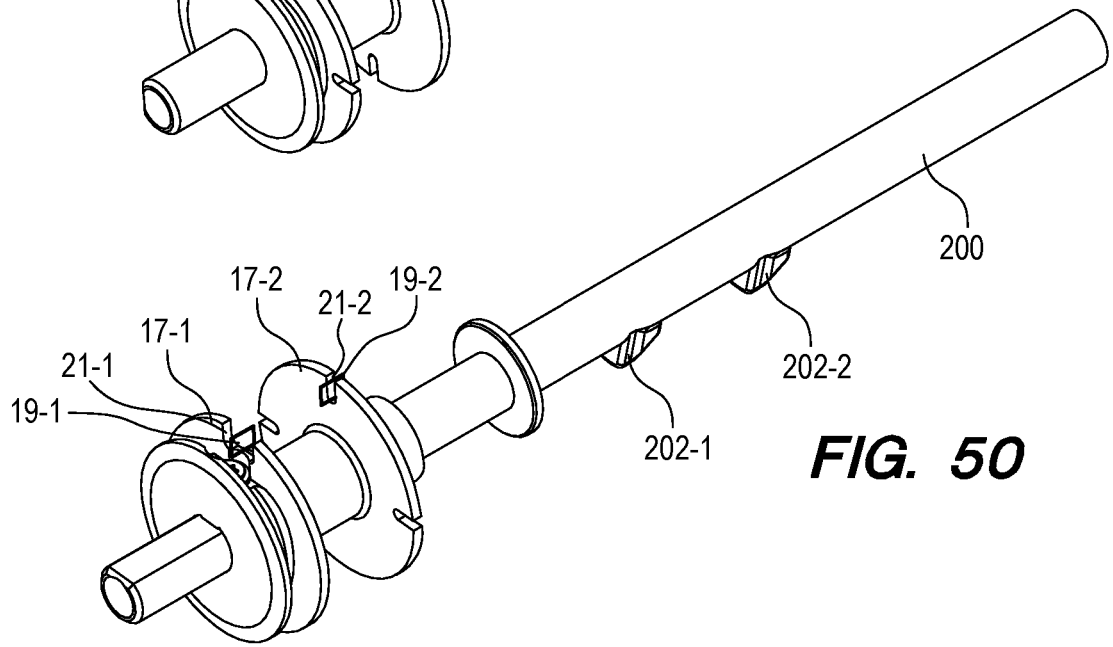
Figure 51:
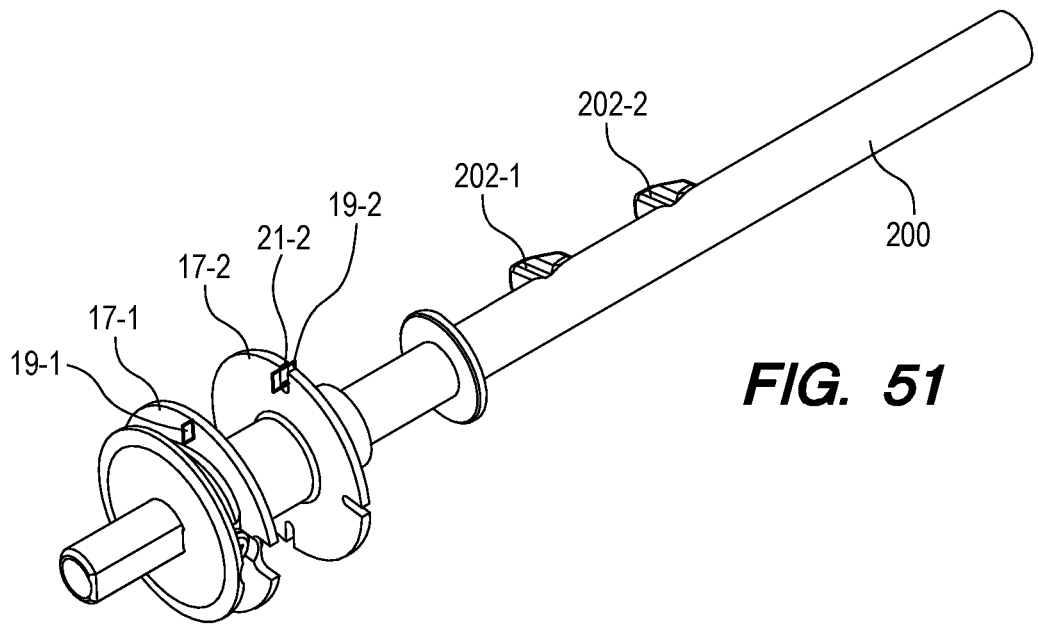
Figure 52:
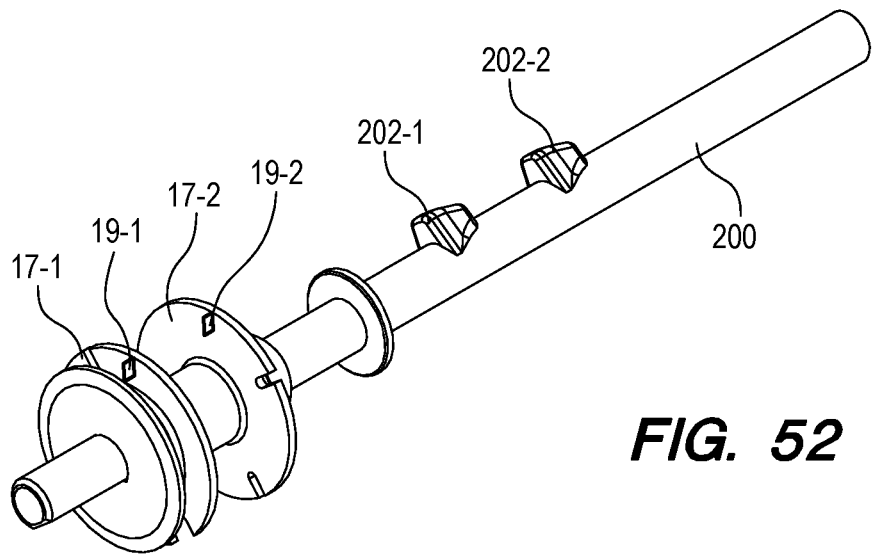

In FIG. 50 the cam 200 is rotated such that both first and second windows 21-1, 21-2 in respective first and second encoding discs 17-1, 17-2 allow respective first and second beams 19-1, 19-2 to pass. However, the first window 21-1 through which the first beam 19-1 passes in FIG. 50 is larger (circumferentially) than that first window 21-1 in FIG. 48. In FIG. 51 the cam 200 is rotated such that a second window 21-2 in the second encoding disc 17-2 allows the second beam 19-2 to pass, but the first encoding disc 17-1 blocks the first beam 19-1. However, the second window 21-2 through which the second beam 19-2 passes in FIG. 51 has a different rotational relationship to the large first window 21-1 than that second window 21-2 in FIG. 49. In FIG. 52 the cam 200 is rotated such that both the first and second encoding discs 17-1, 17-2 block respective first and second beams 19-1, 19-2.

The pair of encoding discs 17-1, 17-2 and their respective sensors provide more cam rotational information to the device controller than the single disc design described above. Accordingly, the duo encoding disc design depicted in FIGS. 48-52 provide more accurate and precise tracking of cam rotational position. While encoding discs 17-1, 17-2 are shown with the cam 200 depicted in FIGS. 40 to 47, the duo encoding disc design can be used to track rotation of any component.

Other aspects of exemplary biopsy devices are described in U.S. patent application Ser. No. 14/497,046, filed Sep. 25, 2014, and in U.S. Provisional Patent Application Ser. No. 62/055,338, filed Sep. 25, 2014. U.S. patent application Ser. No. 14/497,046 is assigned to the same assignee as the instant application, and the full contents thereof are hereby incorporated by reference as though fully set forth herein. U.S. Provisional Patent Application Ser. No. 62/055,338, has been previously incorporated by reference.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A biopsy system driver, comprising:
   a support structure;
   a motor secured to the support structure and comprising a rotatable motor output shaft;
   a spline rotatably coupled to the support structure and operatively connected to the motor output shaft, wherein activation of the motor rotates the spline;
   a drive shaft rotatably coupled to the support structure, wherein the drive shaft is operatively coupled to the spline, wherein rotation of the spline rotates the drive shaft;
   an elongate lead screw axially-translatably coupled to the drive shaft, wherein rotation of the drive shaft rotates the lead screw about an axis of the lead screw, wherein the lead screw is axially translatable relative to the drive shaft between a proximal position and a distal position; and
   a biopsy instrument drive member comprising a biopsy needle engagement element to operatively couple the biopsy instrument drive member to at least a portion of a biopsy needle, wherein the biopsy instrument drive member is movably coupled to the lead screw between a first position and a second position,
      wherein when the lead screw is in the distal position and the biopsy instrument drive member is in the first position, rotation of the lead screw in a first lead screw rotational direction causes axial translation of the biopsy instrument drive member towards the second position, and wherein when the lead screw is in the distal position and the biopsy instrument drive member is in the second position, rotation of the lead screw in the first lead screw rotational direction causes axial translation of the lead screw towards the proximal position.

2. The biopsy system driver of claim 1, wherein rotation of the lead screw in the first lead screw rotational direction causes rotation of the spline in a first spline rotational direction.

3. The biopsy system driver of claim 1, wherein rotation of the lead screw in a second lead screw rotational direction causes rotation of the spline in a second spline rotational direction.

4. The biopsy system driver of claim 1, wherein the biopsy needle engagement element comprises a fork for receiving at least a portion of the biopsy needle.

5. The biopsy system driver of claim 4, wherein the spline is operatively engaged with the at least the portion of the biopsy needle received by the fork.

6. The biopsy system driver of claim 4, wherein the fork comprises a distal lip and a proximal lip for receiving the at least the portion of the biopsy needle.

7. The biopsy system driver of claim 1, wherein a longitudinal axis of the spline is parallel to the axis of the lead screw.

8. The biopsy system driver of claim 1, wherein the spline comprises an elongate pinion.

9. The biopsy system driver of claim 1, further comprising a drive assembly operatively connected to a distal end of the spline, wherein a rotation of the spline causes a rotation of the drive assembly.

10. The biopsy system driver of claim 9, wherein the drive assembly comprises a belt drive assembly comprising a pully-drive belt.

11. The biopsy system driver of claim 9, wherein the drive assembly comprises a gear drive assembly comprising at least one gear.

12. The biopsy system driver of claim 1, wherein the drive shaft and the lead screw are keyed.

13. The biopsy system driver of claim 1, further comprising a dwell spring assembly coupled to the lead screw, wherein the dwell spring assembly comprises a dwell spring and the lead screw is configured to pass through a lumen of the dwell spring.

14. The biopsy system driver of claim 13, wherein when the biopsy instrument drive member is in the second position and the lead screw moves towards the proximal position the dwell spring is further compressed relative to an original compressed position of the dwell spring.

15. The biopsy system driver of claim 13, wherein when the biopsy instrument drive member is in the second position and the lead screw moves towards the distal position the dwell spring is uncompressed relative to an original compressed position of the dwell spring.

16. The biopsy system driver of claim 1, wherein reversing a rotational direction of the motor rotates the lead screw in a second lead screw rotational direction and causes axial translation of the biopsy instrument drive member from the second position towards the first position.

17. The biopsy system driver of claim 1, wherein a pitch of the lead screw is consistent over a length of the lead screw.

18. The biopsy system driver of claim 17, wherein a time of lead screw movement between the distal position and the proximal position is based at least in part on the pitch of the lead screw and a rotational speed of the motor.

19. The biopsy system driver of claim 1, wherein a distance between the first position and the second position is fixed.

20. The biopsy system driver of claim 1, wherein the biopsy instrument drive member is threadedly coupled to the lead screw.

* * * * *